United States Patent [19]

Takano et al.

[11] Patent Number: 4,954,518
[45] Date of Patent: Sep. 4, 1990

[54] 4H-1-BENZOPYRAN-4-ONE DERIVATIVE OR ITS SALT, PROCESS FOR PRODUCING THE SAME AND PHARMACEUTICAL COMPOSITION COMPRISING THE SAME AS ACTIVE INGREDIENT

[75] Inventors: Shuntaro Takano, Toyama; Chosaku Yoshida, Tokaoka; Takihiro Inaba, Namerikawa; Keiichi Tanaka, Toyama; Ryuko Takeno, Toyama; Hideyoshi Nagaki, Toyama; Tomoya Shimotori, Toyama; Shinji Makino, Kurobe, all of Japan

[73] Assignee: Toyama Chemical Company, Ltd., Tokyo, Japan

[21] Appl. No.: 255,121

[22] Filed: Oct. 7, 1988

[30] Foreign Application Priority Data

Oct. 8, 1987 [JP] Japan .................. 62-254251
May 17, 1988 [JP] Japan .................. 63-119990
Oct. 6, 1988 [JP] Japan .................. 63-250811

[51] Int. Cl.⁵ .................. C07D 311/22; A61K 31/35
[52] U.S. Cl. .................. 514/456; 549/403; 549/402; 549/401; 549/400; 549/60; 548/953; 548/950; 548/525; 548/336; 548/327; 548/266.4; 548/262.2; 548/256; 548/253; 548/251; 548/248; 548/245; 548/244; 548/243; 548/236; 548/234; 548/230; 548/228; 548/225; 548/214; 548/213; 548/195; 548/194; 548/188; 548/187; 548/184; 548/159; 548/143; 548/136; 548/129; 548/128; 548/127; 546/269; 546/196; 546/167; 546/164; 546/159; 546/148; 546/143; 546/133; 544/405; 544/376; 544/333; 544/322; 544/238; 544/212; 544/180; 544/179; 544/151; 514/444; 514/422; 514/397; 514/383; 514/382; 514/375; 514/374; 514/372; 514/365; 514/364; 514/363; 514/361; 514/359; 514/352; 514/345; 514/337; 514/320; 514/314; 514/308; 514/305; 514/256; 514/255; 514/233.5; 514/210

[58] Field of Search .............. 549/401, 400, 402, 403, 549/60; 546/269, 167, 143, 164, 196, 159, 148, 133; 548/525, 127, 136, 143, 159, 214, 194, 195, 265.4, 230, 225, 236, 244, 248, 184, 188, 327, 256, 266.4, 253, 953, 228, 234, 243, 245, 213, 187, 336, 129, 262.2, 251, 950, 266.8; 544/322, 376, 238, 180, 179, 333, 405, 212, 151; 514/456, 422, 320, 305, 314, 361, 365, 444, 397, 337, 308, 363, 364, 372, 374, 383, 359, 365, 255, 210, 375, 382, 352, 233.5, 256

[56] References Cited

U.S. PATENT DOCUMENTS 3,661,990  5/1972  Harrington .
3,689,523  9/1972  Trancik et al. .
3,840,597 10/1974  Moore et al. .
4,057,641 11/1977  Appleton et al. .
4,244,960  1/1981  Schröeder et al. .
4,411,910 10/1983  Schroeder et al. .
4,600,788  7/1986  Creuzet et al. .
4,696,948  9/1987  Petzoldt .

FOREIGN PATENT DOCUMENTS 0059884  2/1982  European Pat. Off. .
0125195  3/1984  European Pat. Off. .
0088282 12/1985  European Pat. Off. .
0273369  7/1988  European Pat. Off. .
2537204  4/1976  Fed. Rep. of Germany .
51-61692  5/1976  Japan .

*Primary Examiner*—Nicky Chan
*Attorney, Agent, or Firm*—Oblon, Spivak, McClelland, Maier & Neustadt

[57] ABSTRACT

This invention relates to a 4H-1-benzopyran-4-one derivative represented by the formula:

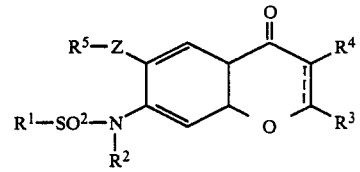

or a salt thereof, a process for producing the same and a pharmaceutical composition comprising the same as active ingredient.

27 Claims, No Drawings

4H-1-BENZOPYRAN-4-ONE DERIVATIVE OR ITS SALT, PROCESS FOR PRODUCING THE SAME AND PHARMACEUTICAL COMPOSITION COMPRISING THE SAME AS ACTIVE INGREDIENT

This invention relates to a novel 4H-1-benzopyran-4-one derivative or a salt thereof, a process for producing the same, a pharmaceutical composition comprising the derivative or a salt thereof as active ingredient and a method of curing inflammation by applying the composition.

Substituted sulfonamide compounds are stated in, for example, Japanese Patent Application Kokai Nos. 4,820/71, 27,961/72, 20,777/80, 136,560/82, 140,712/82, 203,079/82, 170,748/83, 31,755/84, 199,394/85 and 190,869/88, Japanese Patent Publication Nos. 50,984/83 and 44,311/84, etc. and are known to have antiphlogistic and analgesic activities. However, no information has been obtained of substituted sulfonamides having a 4H-1-benzopyran-4-one skeleton.

Many acidic non-steroidal antiinflammatory agents which are now used have a not so great difference between the dose necessary for curing and the dose at which side effect, particularly ulcerogenic effect appears, namely have a small therapeutic index. Therefore, development of antiinflammatory agents having higher safety has been desired.

Under such circumstances, the present inventors have conducted extensive research to find that novel 4H-1-benzopyran-4-one derivatives having specific chemical structure and salts thereof can exhibit an excellent therapeutic effect on inflammation and have substantially no ulcerogenic effect and hence have high safety.

An object of this invention is to provide a novel 4H-1-benzopyran-4-one derivative or a salt thereof, which has an antiinflammatory, antipyretic, analgesic, antirheumatic and antiallergic activity.

Another object of this invention is to provide a process for producing a novel 4H-1-benzopyran-4-one derivative or a salt thereof.

A further object of this invention is to provide a pharmaceutical composition comprising the above derivative or a salt thereof as active ingredient.

A still further object of this invention is to provide a method of curing inflammation, pyrexia, pain, rheumatism and allergy by applying the above derivative or a salt thereof.

Other objects and advantages will become apparent from the following description.

In the present specification, unless otherwise specified, the term "alkyl" means an alkyl group having 1 to 8 carbon atoms such as methyl, ethyl, n-propyl, isopropyl, n-butyl, isobutyl, tert-butyl, pentyl, hexyl, heptyl, octyl and the like; the term "cycloalkyl" means a cycloalkyl group having 3 to 8 carbon atoms such as cyclopropyl, cyclobutyl, cyclopentyl, cyclohexyl, cycloheptyl and the like; the term "lower alkyl" means an alkyl group having 1 to 5 carbon atoms such as methyl, ethyl, n-propyl, isopropyl, n-butyl, isobutyl, tert-butyl, pentyl and the like; the term "lower alkenyl" means an alkenyl group having 2 to 5 carbon atoms such as vinyl, allyl, 1-propenyl, 1-butenyl and the like; the term "alkoxy" means an -O-alkyl group in which the alkyl is the above-mentioned $C_{1-8}$alkyl; the term "acyl" means an alkanoyl group having 1 to 8 carbon atoms such as formyl, acetyl, propionyl, butyryl or the like, an alkoxyalkyl group such as methoxalkyl, ethoxyalkyl or the like, a $C_{3-8}$cycloalkylcarbonyl group such as cyclohexylcarbonyl or the like or an aroyl group such as benzoyl or the like; the term "alkoxycarbonyl" means a —COO—alkyl group in which the alkyl is the above-mentioned $C_{1-8}$alkyl; the term "halogen" means fluorine, chlorine, bromine or iodine; the term "alkylthio" means an —S—alkyl group in which the alkyl is the above-mentioned $C_{1-8}$alkyl group; the term "alkylsulfinyl" means an alkylsulfinyl group having 1 to 4 carbon atoms such as methylsulfinyl, ethylsulfinyl or the like; the term "alkylsulfonyl" means an alkylsulfonyl group having 1 to 4 carbon atoms such as methylsulfonyl, ethylsulfonyl or the like; the term "aryl" means a phenyl or naphthyl group; the term "acylamino" means an —NH—acyl group in which the acyl is the above-mentioned acyl group; the term "alkylamino" means an —NH—alkyl group in which the alkyl is the above-mentioned $C_{1-8}$alkyl group; the term "dialkylamino" means an

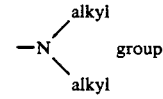

in which the alkyl is the above-mentioned $C_{1-8}$alkyl group; the term "haloalkyl" means a halo-$C_{1-8}$alkyl group such as chloromethyl, fluoromethyl, dichloromethyl, trifluoromethyl, dichloroethyl, trichloroethyl or the like; the term "alkylsulfonyloxy" means an alkylsulfonyl-O- group in which the alkylsulfonyl is the above-mentioned $C_{1-4}$alkylsulfonyl group; the term "arylsulfonyloxy" means a phenylsulfonyloxy or p-toluenesulfonyloxy group; the term "lower alkinyl" means an alkinyl group having 2 to 5 carbon atoms such as ethinyl, 2-propinyl or the like; and the term "heterocyclic group" means a 4-, 5- or 6-membered or fused heterocyclic group containing at least one hetero atom selected from the group consisting of oxygen, nitrogen and sulfur atoms such as thienyl, furyl, pyrrolyl, oxazolyl, isoxazolyl, thiazolyl, isothiazolyl, imidazolyl, benzimidazolyl, benzthiazolyl, 1,2,3-thiadiazolyl, 1,2,4-thiadiazolyl, 1,3,4-thiadiazolyl, 1,3,4-oxadiazolyl, 1,2,3-triazolyl, 1,2,4-triazolyl, tetrazolyl, pyridyl, quinolyl, isoquinolyl, pyrimidinyl, piperazinyl, pyrazinyl, pyridazinyl, 1,2,3,4-tetrahydroquinoyl, 1,2,4-triazinyl, imidazo[1,2-b][1,2,4]triazinyl, pyrrolidinyl, morpholinyl, quinuclidinyl or the like.

According to this invention, there is provided a 4H-1-benzopyran-4-one derivative represented by the following formula or a salt thereof

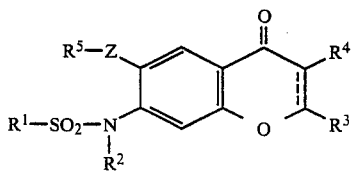

wherein $R^1$ represents an unsubstituted or halogen-substituted lower alkyl, lower alkenyl or aryl group; $R^2$ represents a hydrogen atom or an alkyl or acyl group; $R^3$ represents a hydrogen or halogen atom, a cyano, azido, formyl, carboxyl, hydroxyl or alkoxycarbonyl group, or a substituted or unsubstituted alkyl, alkoxy, phenoxy, cycloalkyl, carbamoyl, amino or phenyl group; $R^4$ represents a hydrogen or halogen atom, a nitro, cyano, carboxyl, acyl, hydroxyl or alkoxycarbonyl group, a substituted or unsubstituted alkyl, alkoxy, alkylthio, phenylthio, lower alkenyl, lower alkinyl, sulfamoyl, alkylsulfinyl, alkylsulfonyl, amidino phenyl or heterocyclic group or a group of the formula,

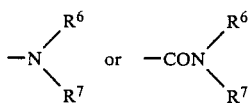

($R^6$ is a hydrogen atom, a hydroxy:, cyano or alkoxycarbonyl group or a substituted or unsubstituted alkyl, cycloalkyl, phenyl, amino, acyl, carbamoyl, alkylsulfonyl, iminomethyl or amidino group, $R^7$ is a hydrogen atom or a substituted or unsubstituted alkyl, alkoxy, phenyl, cycloalkyl or heterocyclic group, and $R^6$ and $R^7$, when taken with the nitrogen atom to which the two are bonded, form a 3- to 7-membered, substituted or unsubstituted heterocyclic group); $R^5$ represents a substituted or unsubstituted phenyl, thienyl, furyl or pyridyl group; Z represents an oxygen or sulfur atom or an imino group; and the broken line means a single or double bond.

This invention further provides a process for producing the above compound, a pharmaceutical composition comprising the compound as active ingredient and a method of curing inflammation, pyrexia, pain, rheumatism and allergy by applying the above compound.

In the formula [I], when $R^6$ and $R^7$ form a 3- to 7-membered heterocyclic group with the nitrogen atom to which the two are bonded, the heterocyclic group includes azetidin-1-yl, pyrrolidin-1-yl, piperidin-1-yl, pyrrol-1-yl and the like.

The alkyl, alkoxy, cycloalkyl, phenoxy, amino, carbamoyl and phenyl groups for $R^3$, the alkyl, alkoxy, alkylthio, phenylthio, amidino, lower alkenyl, lower alkinyl, sulfamoyl, alkylsulfinyl, alkylsulfonyl, phenyl and heterocyclic groups for $R^4$, the alkyl, cycloalkyl, phenyl, amino, acyl, carbamoyl, alkylsulfonyl, iminomethyl and amidino groups for $R^6$, the alkyl, alkoxy, cycloalkyl, phenyl and heterocyclic groups for $R^7$, the 3- to 7-membered heterocyclic groups which $R^6$ and $R^7$ form with the nitrogen atom to which the two are bonded and the phenyl, thienyl, furyl and pyridyl groups for $R^5$ may each be substituted by at least one substituent selected from the group consisting of halogen atoms and alkoxy, alkylthio, phenoxy, carboxyl, acyl, alkoxycarbonyl, carbamoyl, sulfamoyl, cyano, alkylsulfonyl, hydroxyl, mercapto, acylamino, alkylamino, dialkylamino, alkyl, cycloalkyl, oxo, nitro, haloalkyl, amino, phenyl, alkoxycarbonylamino, hydroxyimino and heterocyclic groups.

The salt of the 4H-1-benzopyran-4-one derivative of the formula [I] includes pharmacologically acceptable salts, for example, salts with alkali metals, such as sodium, potassium, and the like; salts with alkaline earth metals such as calcium, magnesium and the like; ammonium salt; salts with organic amine such as triethylamine, pyridine, and the like; salts with amino acids such as lysine, arginine, ornithine, and the like; salts with mineral acids such as hydrochloric acid, hydrobromic acid, sulfuric acid and the like; salts with organic carboxylic acids such as fumaric acid, maleic acid, malic acid, citric acid, and the like; and salts with sulfonic acids such as methanesulfonic acid, p-toluenesulfonic acid, naphthalenedisulfonic acid, and the like.

The compound of this invention includes further all isomers (including geometrical isomers and optical isomers), hydrates, solvates and crystal forms.

The 4H-1-benzopyran-4-one derivative of the formula [I] or a salt thereof can be produced by, for example, the following processes:

Production Process 1

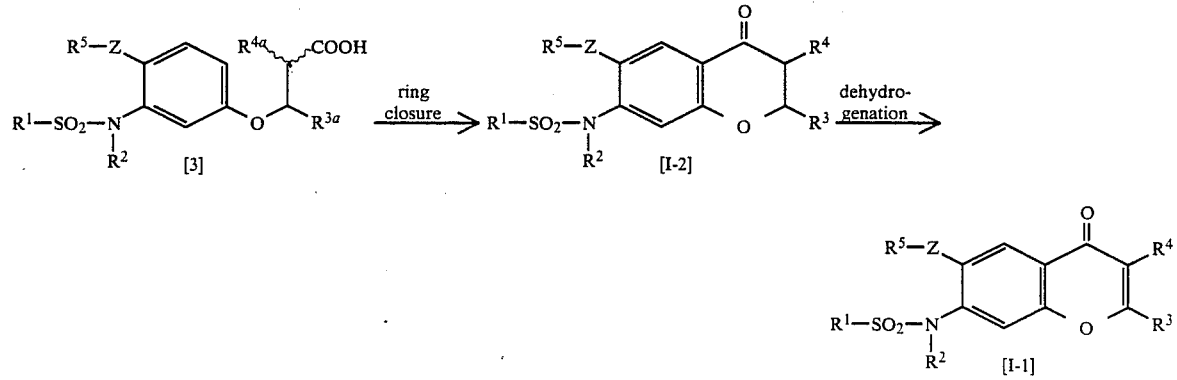

Production Process 2

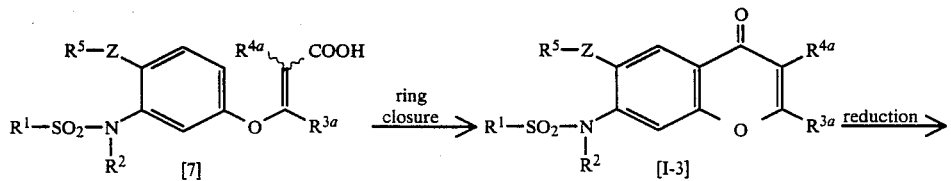
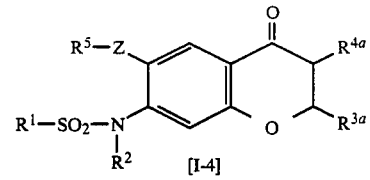
Production Process 3
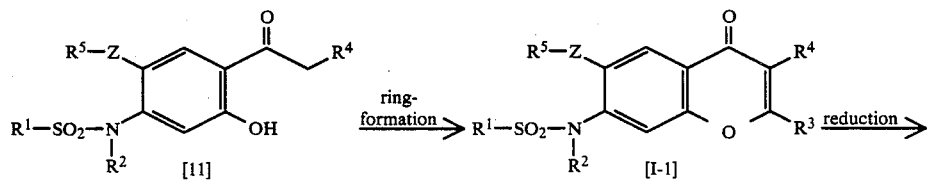
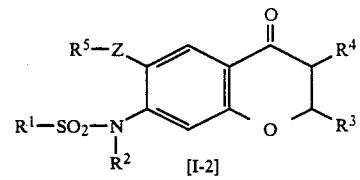
Production Process 4
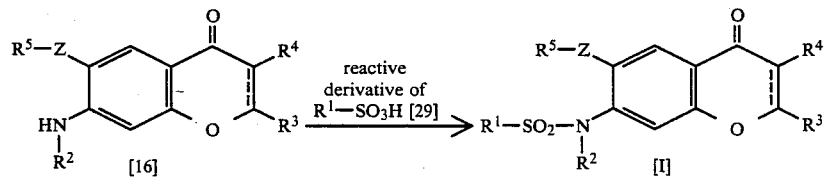
Production Process 5
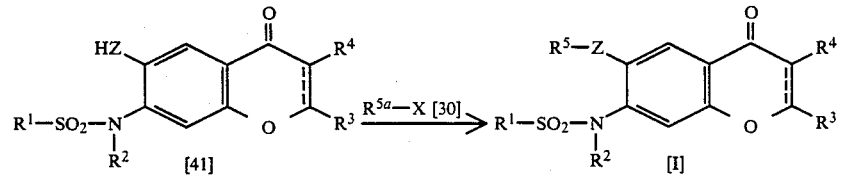
Production Process 6
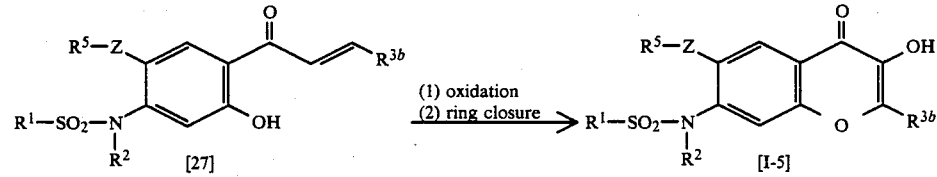
Production Process 7
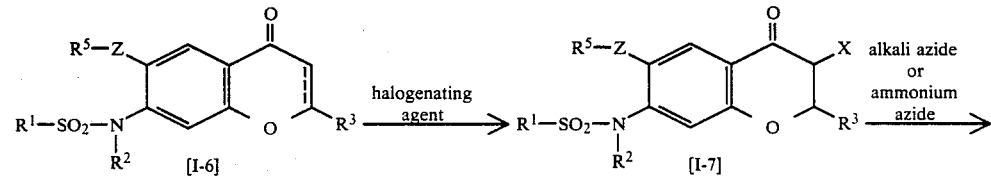

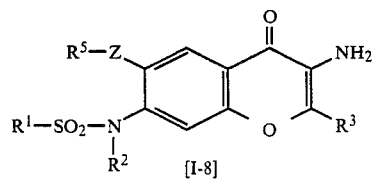
Production Process 8
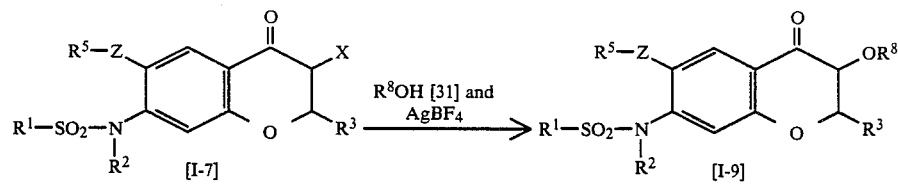
Production Process 9
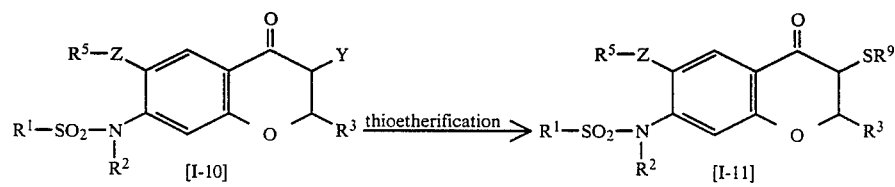
Production Process 10
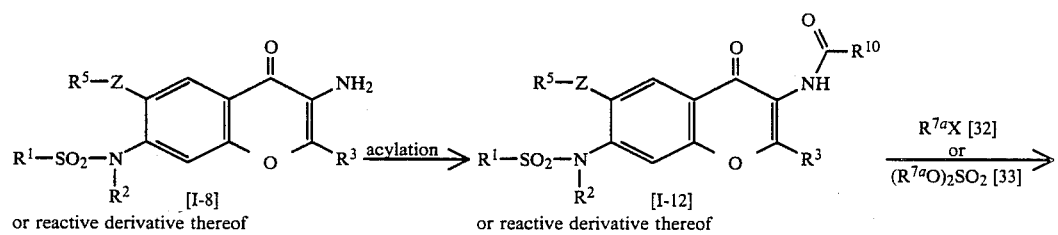
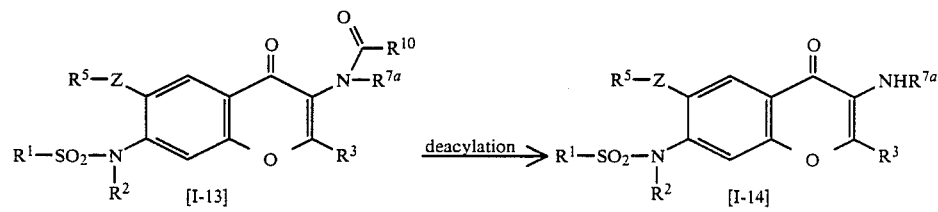
Production Process 11
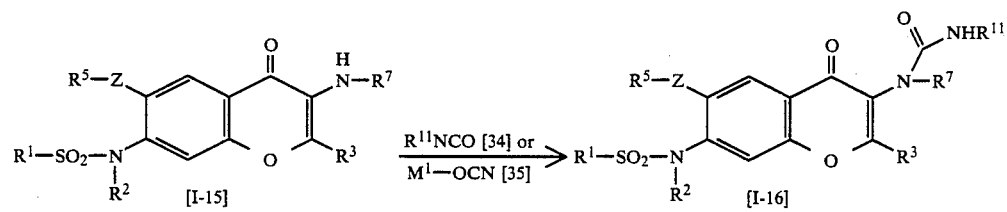
Production Process 12
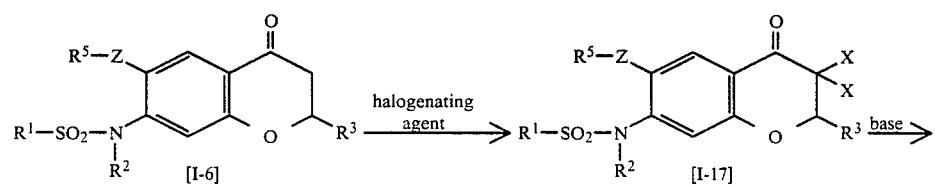

-continued
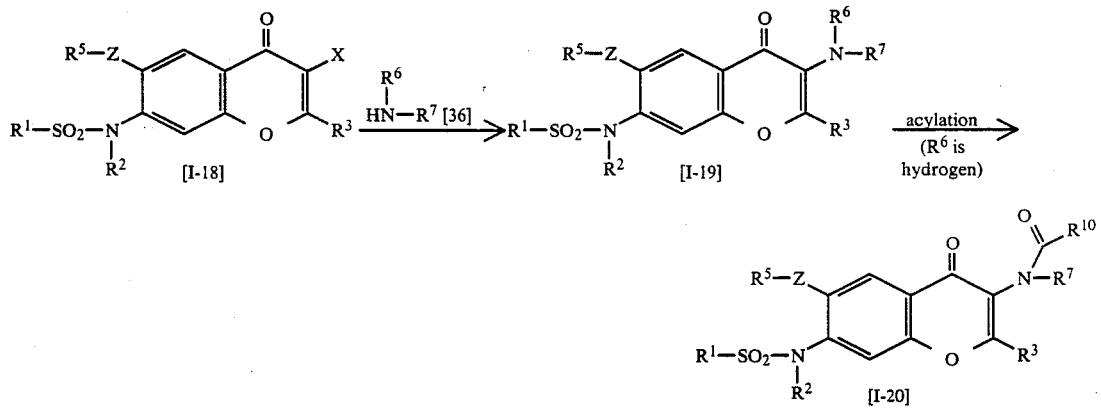
Production Process 13
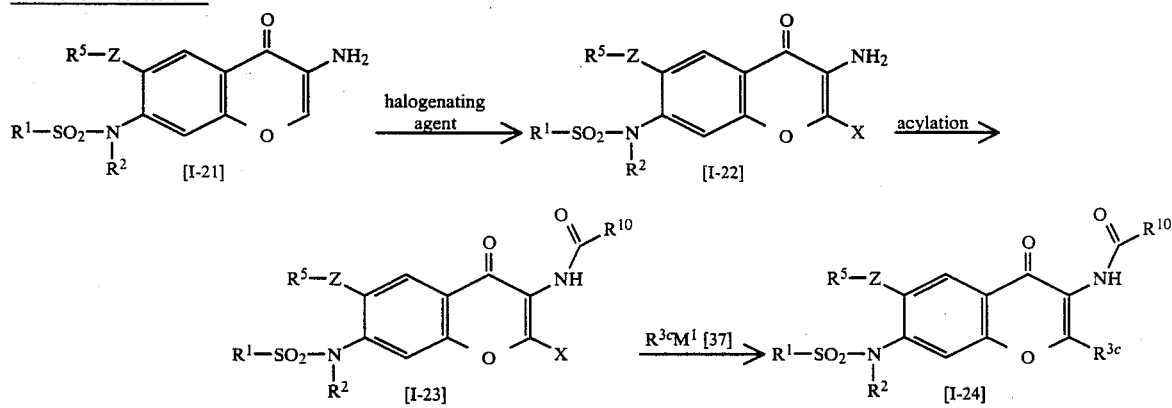
Production Process 14
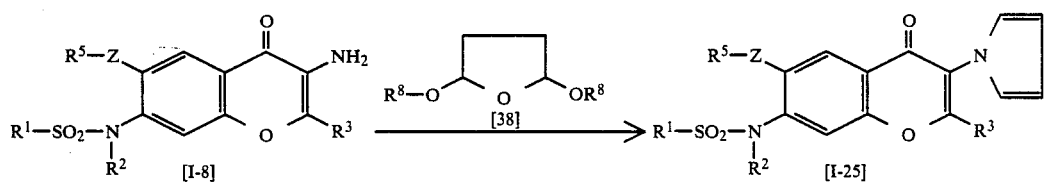
Production Process 15
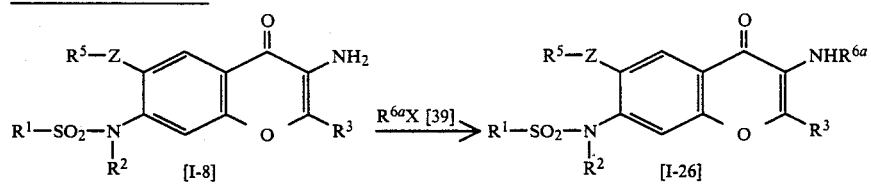
Production Process 16
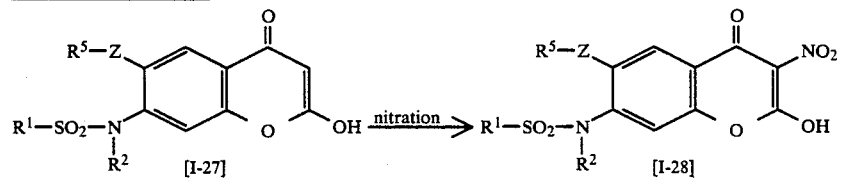
Production Process 17
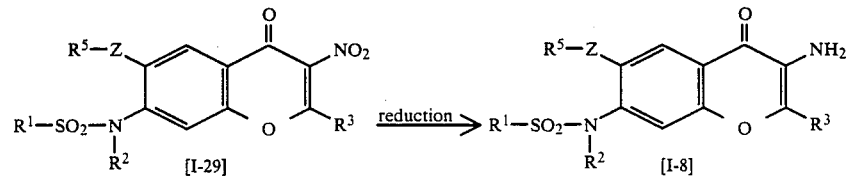

Production Process 18

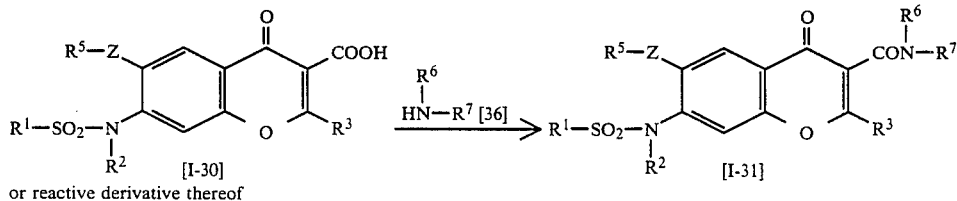

or reactive derivative thereof

Production Process 19

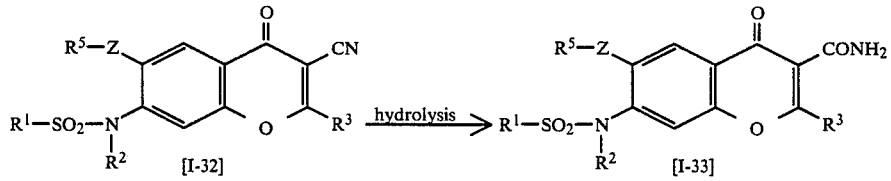

In the above formulas, Z, $R^1$, $R^2$, $R^3$, $R^4$, $R^5$, $R^6$, $R^7$ and the broken line have the same meanings as defined above; $R^8$ means a lower alkyl group; $R^9$ means a substituted or unsubstituted alkyl or phenyl group; $R^{10}$ means a hydrogen atom, an alkoxy group or a substituted or unsubstituted alkyl, cycloalkyl, phenyl, acyl or alkoxycarbonyl group; $R^{11}$ means a hydrogen atom or a chlorosulfonyl or alkyl group; $R^{3a}$ means a hydrogen atom or a substituted or unsubstituted alkyl, cycloalkyl or phenyl group as defined as to $R^3$; $R^{3b}$ means a substituted or unsubstituted phenyl as defined as to $R^3$; $R^{3c}$ means a hydroxyl, cyano or azido group or a substituted or unsubstituted alkoxy or amino group as defined as to $R^3$; $R^{4a}$ means a hydrogen atom, a cyano, acyl or alkoxycarbonyl group, a substituted or unsubstituted alkyl or phenyl group or a group of the formula,

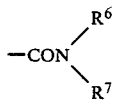

($R^6$ and $R^7$ have the same meanings as defined above) as defined as to $R^4$; $R^{6a}$ means a cyano group or a substituted or unsubstituted alkyl, cycloalkyl or phenyl group as defined as to $R^6$; $R^{7a}$ means a substituted or unsubstituted alkyl, cycloalkyl, alkoxy, phenyl or heterocyclic group as defined as to $R^7$; $R^{5a}$ means a substituted or unsubstituted phenyl, thienyl, furyl, pyridyl, diphenyliodonium or 4-pyridylpyridinium group; $M^1$ means a hydrogen atom, an alkali metal such as sodium, potassium or the like, an alkaline earth metal such as magnesium or the like or a transition metal such as copper(monovalent) or the like; X means a halogen atom; Y means a halogen or hydrogen atom and $\sim$ means a (E)isomer, a (Z)isomer or a mixture thereof.

The compounds represented by the formulas [I-1] to [I-33] may also be obtained in the form of salts, and the definition of the salts of the compound of the formula [I] mentioned above can be applied to these salts.

Each production process is explained in detail below.

Production Process 1

(1) The compound of the formula [I-2] can be obtained by subjecting a compound of the formula [3] to ring closure reaction.

In this reaction, a solvent may be used, which may be any solvent as far as it dose not adversely affect the reaction, and includes, for example, benzene, xylene and the like; however, this reaction may be conducted in the absence of a solvent.

In this ring closure reaction, a condensing agent is used, which includes phosphorus pentoxide, polyphosphoric acid, zinc chloride, conc. sulfuric acid, halogenosulfonic acids, sulfuric anhydride, conc. sulfuric acid-acetyl chloride and the like. The condensing agent is used in an amount of 1 to 50 moles per mole of the compound of the formula [3].

The ring closure reaction may be carried out at a temperature of 0° to 120° C. for a period of 30 minutes to 24 hours.

Also, the ring closure may be conducted by treating the compound of the formula [3] with an acid-halogenating agent such as thionyl chloride, phosphorus pentachloride or the like and then subjecting the product to the Friedel-Crafts reaction with a Lewis acid such as aluminum chloride.

(2) The compound of the formula [I-1] can be obtained by subjecting the compound of the formula [I-2] to dehydrogenation reaction.

The dehydrogenation reaction may be conducted by, for example, the following methods:

(i) The compound of the formula [I-1] can be obtained by reacting the compound of the formula [I-2] with a dehydrogenating agent.

In this reaction, a solvent may be used, which may be any solvent as far as it does not adversely affect the reaction. It includes, for example, water; acetic acid; acetic anhydride; aromatic hydrocarbons such as benzene, toluene, xylene and the like; ethers such as dioxane and the like; etc.

The dehydrogenating agent includes, for example, 2,3-dichloro-5,6-dicyano-1,4-benzoquinone (DDQ), chloranil, trityl perchlorate, trityl fluoroborate, selenium dioxide, paradium-carbon and the like.

In the above reaction, the amount of the dehydrating agent used is 0.5 to 5 moles per mole of the compound of the formula [I-2].

The above reaction may be carried out at a temperature of 0° to 150° C. for a period of 30 minutes to 72 hours.

(ii) The compound of the formula [I-1] can also be obtained by reacting the compound of the formula [I-2] with a halogenating agent and then treating the halogenated product thus obtained with a base.

A solvent may be used in the halogenation reaction, which may be any solvent as far as it does not adversely affect the reaction. It includes, for example, halogenated hydrocarbons such as methylene chloride, 1,2-dichloroethane, chloroform and the like; alcohols such as methanol, ethanol and the like; esters such as ethyl acetate and the like; organic carboxylic acids such as acetic acid, formic acid and the like; etc. These solvents may be used alone or in admixture of two or more.

The halogenating agent used in the above reaction includes, for example, chlorine, bromine, sulfuryl chloride and the like The amount of the halogenating agent used is 0.9 to 1.1 moles per mole of the compound of the formula [I-2].

The halogenation reaction may usually be carried out at a temperature of 0° to 100° C., preferably 10° to 40° C., for a period of 30 minutes to 3 hours.

The halogenated product thus obtained may be reacted with a base in a solvent which may be any solvent as far as it does not adversely affect the reaction. The solvent includes, for example, halogenated hydrocarbons such as methylene chloride, 1,2-dichloroethane, chloroform and the like; alcohols such as methanol, ethanol and the like; amides such as N,N-dimethylformamide and the like; pyridine; etc. These solvents may be used alone or in admixture of two or more.

The base used in the above reaction includes organic bases such as triethylamine, 1,8-diazabicyclo-[5,4,0]undec-7-ene (DBU), pyridine and the like and alkali metal carbonates such as sodium carbonate, potassium carbonate and the like. The amount of the base used is 1 to 10 moles per mole of the compound of the formula [I-2].

The above reaction may be carried out at a temperature of 0° to 100° C. for a period of 30 minutes to 24 hours.

Production Process 2

(1) (i) The compound of the formula [I-3] can be obtained by subjecting a compound of the formula [7] to ring closure reaction In this reaction, a solvent may be used, which may be any solvent as far as it does not adversely affect the reaction, and includes, for example, aromatic hydrocarbons such as benzene, toluene, xylene and the like and halogenated aromatic hydrocarbons such as chlorobenzene and the like. These solvents may be used alone or in admixture of two or more.

A condensing agent is used in this reaction, which includes, for example, halogenosulfonic acids, sulfuric anhydride, phosphorus pentoxide, polyphosphoric acid, zinc chloride, conc. sulfuric acid, conc. sulfuric acid-acetyl chloride and the like. The amount of the condensing agent used is 1 to 50 moles per mole of the compound of the formula [7].

The above reaction may usually be carried out at a temperature of 0° to 120° C. for a period of 30 minutes to 24 hours (ii) The ring closure reaction may also be achieved by reacting the compound of the formula [7] with an acid-halogenating agent such as thionyl chloride, phosphorus pentachloride or the like to form a carboxylic acid halide and then subjecting the carboxylic acid halide to the Friedel-Crafts reaction with a Lewis acid such as aluminum chloride or the like.

(2) The compound of the formula [I-4] can be obtained by catalytic hydrogenation of a compound of the formula [I-3].

In this reaction, a solvent may be used, which may be any solvent as far as it does not adversely affect the reaction, and includes, for example, alcohols such as methanol, ethanol and the like; organic carboxylic acids such as acetic acid and the like; esters such as ethyl acetate and the like; ethers such as dioxane and the like; aqueous sodium hydroxide solution; etc. These solvents may be used alone or in admixture of two or more.

The catalyst used in this reaction includes, for example, palladium, palladium-carbon, platinum and Raney nickel and the like. The amount of the catalyst used is 0.01 to 0.5 mole per mole of the compound of the formula [I-3].

The above reaction may usually be carried out at a temperature of 0° to 100° C., preferably 20° to 60° C., for a period of 30 minutes to 24 hours Production Process 3

(1) The compound of the formula [I-1] can be obtained by subjecting the compound of the formula [11] to ring-formation reaction The ring-formation reaction may be conducted by, for example, the following methods (i) The compound of the formula [11] is reacted with a compound of the formula, $R^3COOR^{12}$ [a] in which $R^3$ has the same meaning as defined above and $R^{12}$ means a hydrogen atom or the ester residue in the carboxyl group, for example, a lower alkyl group or the like, in the presence of a base to obtain a β-diketone, which is then subjected to ring closure reaction, thereby obtaining the compound of the formula [I-1].

In this reaction, a solvent may be used, which may be any solvent as far as it does not adversely affect the reaction, and includes, for example, aromatic hydrocarbons such as benzene, toluene, xylene and the like and alcohols such as methanol, ethanol and the like. These solvents may be used alone or in admixture of two or more. The compound of the formula [a] may also be used as the solvent The base used in this reaction includes, for example, metallic alkalis such as metallic sodium, metallic potassium and the like; alkali metal hydrides such as sodium hydride, potassium hydride and the like; and alkali metal amides such as sodium amide, potassium amide and the like.

The amounts of the base and the compound of the formula [a] used are each 1 to 100 moles per mole of the compound of the formula [11].

The above reaction may usually be carried out at a temperature of −20° to 150° C. for a period of 30 minutes to 48 hours.

Also, in the subsequent ring closure reaction, a catalyst may be used, which includes, for example, hydrogen halides such as hydrogen chloride, hydrogen bromide and the like; mineral acids such as hydrochloric acid, hydrobromic acid, sulfuric acid and the like; alkali metal acetates such as sodium acetate, potassium acetate and the like; and alkali metal carbonates such as sodium carbonate, potassium carbonate and the like In this reaction, a solvent may be used, which may be any solvent as far as it does not adversely affect the reaction, and includes, for example, alcohols such as methanol, ethanol and the like; organic carboxylic acids such as acetic acid and the like; and water. These solvents may be used alone or in admixture of two or more.

The amount of the catalyst used is 0.1 to 5 moles per mole of the compound of the formula [11].

The above reaction may usually be carried out at a temperature of 20° to 100° C. for a period of 5 minutes to 2 hours.

If necessary, α-acyl form or ketoester form obtained by the Claisen condensation may be isolated as intermediate. In this case, the objective compound of the formula [I-1] can be obtained by treating the intermediate with a base or an acid.

(ii) The compound of the formula [11] is reacted with a compound of the formula [b], $(R^{3d}CO)_2O$ ($R^{3d}$ means a substituted or unsubstituted alkyl or phenyl group as defined as to $R^3$) and a compound of the formula [c], $R^{3d}COOM^2$ ($R^{3d}$ has the same meaning as defined above and $M^2$ means an alkali metal such as sodium, potassium or the like) to obtain a compound of the formula [I-1] in which $R^3$ is $R^{3d}$.

This reaction may be effected according to the Allan-Robinson condensation stated in J. Chem Soc., vol. 125, p. 2192 (1924) or the like.

The amounts of the compounds of the formulas [b] and [c] used are 1 to 50 moles and 1 to 5 moles, respectively, per mole of the compound of the formula [11].

This reaction may usually be effected at a temperature of 0° to 200° C. for a period of 30 minutes to 24 hours.

If necessary, α-acyl form obtained by the Claisen condensation may be isolated as intermediate, and in this case, the objective compound of the formula [I-1] can be obtained by treating the intermediate with a base or an acid.

(iii) The compound of the formula [11] is reacted with a compound of the formula [d], $HXO_4$ (X has the same meaning as defined above), and a compound of the formula [e], $HC(OR^{17})_3$ ($R^{17}$ means a lower alkyl group), and the reaction product is then subjected to hydrolysis to obtain a compound of the formula [I-1] in which $R^3$ is a hydrogen atom.

This reaction can be effected according to the method stated in the Journal of Chemical Research (M), pp. 864–872 (1978).

(a) In this reaction, the compound of the formula [e] may also be used as a solvent.

The amounts of the compounds of the formulas [d] and [e] used are 1 to 5 moles and 5 to 100 moles, respectively, per mole of the compound of the formula [11].

The above reaction may usually be carried out at a temperature of 0° to 50° C. for a period of 10 minutes to 12 hours.

(b) Subsequently, the compound thus obtained is hydrolyzed to obtain a compound of the formula [I-1] in which $R^3$ is a hydrogen atom.

(iv) A compound of the formula [11] in which $R^4$ is —$COR^{4b}$ ($R^{4b}$ means a hydrogen atom or a substituted or unsubstituted alkyl, cycloalkyl, phenyl, alkoxy or heterocyclic group as defined as to $R^4$) or a nitro group is reacted with a compound of the formula [f], $(CH_3)_2NCH(OR^{17})_2$ ($R^{17}$ has the same meaning as defined above), to obtain a compound of the formula [I-1] in which $R^4$ is —$COR^{4b}$ ($R^{4b}$ has the same meaning as defined above) or a nitro group and $R^3$ is a hydrogen atom.

In this reaction, a solvent may be used, which may be any solvent as far as it does not adversely affect the reaction, and includes, for example, amides such as N,N-dimethylformamide and the like; sulfoxides such as dimethylsulfoxide and the like; aromatic hydrocarbons such as benzene, toluene, xylene and the like; ethers such as diethyl ether, dioxane, tetrahydrofuran and the like; etc. These solvents may be used alone or in admixture of two or more.

The amount of the compound of the formula [f] used is 1 to 5 moles per mole of the compound of the formula [11].

The above reaction may usually be carried out at a temperature of 0° to 100° C. for a period of 30 minutes to 24 hours.

Also, the compound of the formula [I-1] in which $R^4$ is —$COR^{4b}$ ($R^{4b}$ has the same meaning as defined above) or a nitro group and $R^3$ is a hydrogen atom can be obtained by reacting the compound of the formula [11] in which $R^4$ is —$COR^{4b}$ ($R^{4b}$ has the same meaning as defined above) or a nitro group with the compound of the formula [e] and the compound of the formula [b].

This reaction can be effected according to the method stated in Chem. Pharm. Bull., 22, 331–336 (1974).

The amounts of the compounds of the formulas [e] and [b] used are 1 to 5 moles and 1 to 50 moles, respectively, per mole of the compound of the formula [11].

The above reaction may usually be carried out at a temperature of 20° to 150° C. for a period of 30 minutes to 24 hours Further, the compound of the formula [11] in which $R^4$ is —$COR^{4b}$ ($R^{4b}$ has the same meaning as defined above) or a nitro group can be reacted with a compound of the formula [g],

($R^{17}$ is the same as defined above) and a compound of the formula [h], $HCOOM^2$ ($M^2$ is an alkali metal such as sodium, potassium or the like), to obtain the compound of the formula [I-1] in which $R^4$ is —$COR^{4b}$ ($R^{4b}$ has the same meaning as defined above) or a nitro group and $R^3$ is a hydrogen atom.

This reaction can be effected according to the method stated in Chem. Pharm Bull , 22, 331–336 (1974).

The amounts of the compounds of the formulas [g] and [h] used are 1 to 100 moles and 1 to 50 moles, respectively, per mole of the compound of the formula 11].

The above reaction may usually be carried out at a temperature of 0° to 100° C. for a period of 30 minutes to 24 hours.

(v) A compound of the formula [I-1] in which $R^3$ is a hydroxyl group can be obtained by reacting the compound of the formula [11] with a compound of the formula [i], $(R^{17}O)_2CO$ ($R^{17}$ has the same meaning as defined above) in the presence of a base.

In this reaction, a solvent may be used, which may be any solvent as far as it does not adversely affect the reaction, and includes, for example, aromatic hydrocarbons such as benzene, toluene, xylene and the like; amides such as N,N-dimethylformamide and the like; ethers such as tetrahydrofuran, dioxane and the like; etc. However, the above reaction may also be effected in the absence of a solvent.

The base used in this reaction includes, for example, metallic alkalis such as metallic sodium, metallic potassium and the like; alkali metal amides such as sodium amide, potassium amide and the like; alkali metal alkoxides such as sodium methoxide, sodium ethoxide, potassium tert-butoxide and the like; alkali metal hydrides such as sodium hydride, potassium hydride and the like; etc.

The amounts of the base and the compound of the formula [i] used are 1 to 10 moles and 1 to 100 moles, respectively, per mole of the compound of the formula [11].

The above reaction may usually be carried out at a temperature of 20° to 150° C. for a period of 30 minutes to 24 hours.

(2) The compound of the formula [I-2] can be obtained by subjecting the compound of the formula [I-1] to reduction reaction.

This reaction can be conducted according to the method stated in Production Process 2(2).

Production Process 4

The compound of the formula [I] can be obtained by reacting a compound of the formula [16] with a reactive derivative of a compound of the formula [29].

In this reaction, a solvent may be used, which may be any solvent as far as it does not adversely affect the reaction, and includes, for example, halogenated hydrocarbons such as methylene chloride, chloroform, 1,2-dichloroethane and the like; amides such as N,N-dimethylformadmide, N,N-dimethylacetamide and the like; sulfoxides such as dimethylsulfoxide and the like; etc. Also, an organic amine such as pyridine or the like may be used as the solvent.

This reaction may be effected in the presence of a base, which includes alkali metal hydrides such as sodium hydride, potassium hydride and the like; alkali metal alkoxides such as sodium methoxide, sodium ethoxide, potassium tert-butoxide and the like; organic amines such as triethylamine, pyridine and the like; alkali metal carbonates such as potassium carbonate, sodium carbonate and the like; etc.

The reactive derivative of the compound of the formula [29] includes, for example, acid halides, acid anhydrides and the like.

The amounts of the base and the reactive derivative of the compound of the formula [29] used are each 1 to 1.5 moles per mole of the compound of the formula [16].

The above reaction may be carried out at a temperature of −30 ° to 150° C. for a period of 30 minutes to 24 hours.

Production Process 5

The compound of the formula [I] can be obtained by reacting the compound of the formula [41] with a compound of the formula [30].

In this reaction, a solvent may be used, which may be any solvent as far as it does not adversely affect the reaction, and includes, for example, amides such as N,N-dimethylformamide and the like; sulfoxides such as dimethylsulfoxide and the like; ketones such as acetone and the like; alcohols such as methanol, ethanol and the like; collidine; etc. These solvents may be used alone or in admixture of two or more.

In this reaction, a base may be used, which includes, for example, alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; etc.

The amounts of the compound of the formula [30] and the base used are 1 to 5 moles and 1 to 3 moles, respectively, per mole of the compound of the formula [41].

The above reaction can also be carried out using as a catalyst, copper powder, cuprous oxide, cuprous chloride, cuprous chloride-8-hydroxyquinoline or the like in a proportion of 0.01 to 2 moles per mole of the compound of the formula [41].

A compound of the formula [I] in which $R^5$ is pyridyl or phenyl can be obtained by reacting a 4-pyridylpyridium chloride hydrochloride or diphenyliodonium bromide with the compound of the formula [41].

The above reaction may usually be carried out at a temperature of −20° to 160° C. for a period of 30 minutes to 24 hours.

Production Process 6

The compound of the formula [I-5] can be obtained by reacting the compound of the formula [27] with alkaline hydrogen peroxide.

Incidentally, this reaction can be effected according to the method stated in the Journal of the Pharmaceutical Society of Japan, 71, 1178–1183 (1951).

Production Process 7

(1) The compound of the formula [I-7] can be obtained by reacting a compound of the formula [I-6] with a halogenating agent.

In this reaction, a solvent may be used, which may be any solvent as far as it does not adversely affect the reaction, and includes, for example, halogenated hydrocarbons such as methylene chloride, 1,2-dichloroethane, chloroform and the like; alcohols such as methanol, ethanol and the like; esters such as ethyl acetate and the like; organic carboxylic acids such as acetic acid, formic acid and the like; etc. These solvents may be used alone or in admixture of two or more.

The halogenating agent used in the above reaction includes, for example, chlorine, bromine, sulfuryl chloride and the like.

The amount of the halogenating agent used is 0.9 to 1.1 moles per mole of the compound of the formula [I-6].

The above reaction may usually be carried out at a temperature of 0° to 100° C., preferably 10° to 40° C., for a period of 30 minutes to 3 hours.

(2) The compound of the formula [I-8] can be obtained by reacting the compound of the formula [I-7] with an alkali metal azide such as sodium azide, potassium azide or the like or ammonium azide.

This reaction can be effected according to the method stated in Chemical Abstracts, vol 89:43022p.

In this reaction, a solvent may be used, which may be any solvent as far as it does not adversely affect the reaction, and includes, for example, water; amides such as N,N-dimethylformamide, N,N-dimethylacetamide and the like; sulfolane; nitriles such as acetonitrile and the like; ketones such as acetone and the like; sulfoxides such as dimethylsulfoxide and the like; alcohols such as methanol, ethanol and the like; ethers such as tetrahydrofuran, dioxane and the like; etc. These solvents may be used alone or in admixture of two or more.

The amount of the alkali or ammonium azide used is 1 to 5 moles per mole of the compound of the formula [I-7].

The above reaction may usually be carried out at a temperature of room temperature to 100° C. for a period of 30 minutes to 12 hours.

Production Process 8

The compound of the formula [I-9] can be obtained by reacting the compound of the formula [I-7] with a compound of the formula [31] in the presence of silver tetrafluoroborate.

In this reaction, the compound of the formula [31] may be used as a solvent.

The amount of the silver tetrafluoroborate and the compound of the formula [31] used in this reaction are 1 to 5 moles and 10 to 100 moles, respectively, per mole of the compound of the formula [I-7].

The above reaction may usually be carried out at a temperature of 20° to 100° C. for a period of 30 minutes to 24 hours.

Production Process 9

The compound of the formula [I-11] can be obtained by subjecting a compound of the formula [I-10] to thioetherification in the presence of a base.

(i) The compound of the formula [I-11] can be obtained by reacting a compound of the formula [I-10] in which Y is a halogen atom with a compound of the formula [j], $R^9SH$ ($R^9$ has the same meaning as defined above) in the presence of a base.

In this reaction, a solvent may be used, which may be any solvent as far as it does not adversely affect the reaction, and includes, for example, halogenated hydrocarbons such as methylene chloride, 1,2-dichloroethane, chloroform and the like; alcohols such as methanol, ethanol, and the like; amides such as N,N-dimethylformamide and the like; ketones such as acetone and the like; ethers such as dioxane, tetrahydrofuran and the like; etc. These solvents may be used alone or in admixture of two or more.

The base used in the above reaction includes, for example, organic bases such as triethylamine, pyridine and the like; metallic alkalis such as metallic sodium, metallic potassium and the like; alkali carbonates such as sodium carbonate, potassium carbonate and the like; alkali alkoxides such as sodium methoxide, sodium ethoxide, potassium t-butoxide and the like; etc.

The amounts of the base and the compound of the formula [j] used are 1 to 10 moles and 1 to 5 moles, respectively, per mole of the compound of the formula [I-10].

The above reaction may usually be carried out at a temperature of 0° to 150° C. for a period of 30 minutes to 24 hours.

(ii) The compound of the formula [I-11] can be obtained by reacting a compound of the formula [I-10] in which Y is a hydrogen atom with a base, and then reacting the product with a thioetherifying agent.

In this reaction, a solvent may be used, which may be any solvent as far as it does not adversely affect the reaction, and includes, for example, ethers such as diethyl ether, tetrahydrofuran, dioxane and the like; aromatic hydrocarbons such as benzene, toluene and the like; hexamethylphosphoric triamide(HMPA); and the like. These solvents may be used alone or in admixture of two or more.

The base used in the above reaction includes organolithium compounds such as butyllithium, phenyllithium, lithiumdiisopropylamine, lithiumhexamethyldisilazane and the like; etc.

Also, the thioetherifying agent includes disulfides such as dimethyl sulfide, diphenyl sulfide and the like; thiolsulfonates such as methyl benzenethiolsulfonate, methyl methanethiolsulfonate, and the like; sulfenyl halides such as phenylsulfenyl chloride, methylsulphenyl chloride; etc.

The amounts of the base and the thioetherifying agent used are each 1 to 10 moles per mole of the compound of the formula [I-10].

The above reaction may be usually carried out at a temperature of −78° to 0° C. for a period of 1 to 24 hours.

Production Process 10

(1) The compound of the formula [I-12] can be obtained by reacting a compound of the formula [I-8] or a reactive derivative thereof with an acylating agent.

This acylation can be conducted by reacting, for example, a compound of the formula [I-8] or a reactive derivative thereof with a compound of the formula [k], $R^{10}COOH$ ($R^{10}$ has the same meaning as defined above) or a reactive derivative thereof.

In this reaction, a solvent may be used, which may be any solvent as far as it does not adversely affect the reaction, and includes, for example, halogenated hydrocarbons such as methylene chloride, 1,2-dichloroethane, chloroform and the like; alcohols such as methanol, ethanol and the like; esters such as ethyl acetate and the like; amides such as N,N-dimethylformamide, N,N-dimethylacetamide and the like; nitriles such as acetonitrile and the like; organic carboxylic acids such as acetic acid, formic acid and the like; etc. These solvents may be used alone or in admixture of two or more.

In this reaction, a base may also be used, which includes, for example, organic bases such as triethylamine, pyridine; alkali metal carbonates such as sodium carbonates, potassium carbonate and the like; alkali metal hydrogencarbonates such as sodium hydrogencarbonate, potassium hydrogencarbonate and the like.

The reactive derivative of the compound of the formula [I-8] includes, for example, those activated by a conventionally known organic silylating agent.

The reactive derivative of the compound of the formula [k] includes, for example, those in the carboxyl group such as acid halides, mixed acid anhydrides, acid anhydrides, active esters, active amides and the like; and those obtained by reacting the compound of the formula [k] with a Vilsmeier reagent.

Also, when the compound of the formula [k] or a salt thereof is used, the above acylation reaction can be conducted in the presence of a conventionally known condensing agent such as N,N-dicyclohexylcarbodimide or the like.

The amount of the compound of the formula [k] or a reactive derivative thereof used and the amount of the base used are each 1 to 5 moles per mole of the compound of the formula [I-8] or its reactive derivative.

The above reaction may usually be carried out at a temperature of −20° to 100° C. for a period of 30 minutes to 24 hours.

In the formylation to obtain a compound of the formula [I-12] in which $R^{10}$ is a hydrogen atom, there may be used a conventional formylating agent such as formic acid-acetic anhydride, a formic acid ester or the like.

(2) The compound of the formula [I-13] can be obtained by reacting the compound of the formula [I-12] with a compound of the formula [32] or [33].

In this reaction, a solvent may be used, which may be any solvent as far as it does not adversely affect the reaction, and includes, for example, amides such as N,N-dimethylformamide and the like; sulfoxides such as dimethylsulfoxide and the like; alcohols such as methanol, ethanol and the like; ketones such as acetone and the like; etc. These solvents may be used alone or in admixture of two or more.

In this reaction, a base may also be used, which includes, for example, alkali metal alkoxides such as sodium methoxide, sodium ethoxide, potassium tert-butoxide and the like; alkali metal hydrides such as sodium hydride, potassium hydride and the like; alkali metal carbonates such as potassium carbonate, sodium carbonate and the like; etc.

The amounts of the compounds of the formula [32] or [33] and the base used are 1 to 5 moles and 1 to 3 moles, respectively, per mole of the compound of the formula [I-12].

The above reaction may usually be carried out at a temperature of −20° to 150° C. for a period of 30 minutes to 24 hours.

(3) The compound of the formula [I-14] can be obtained by subjecting the compound of the formula [I-13] to deacylation reaction. The deacylation reaction includes, for example, hydrolysis and the like.

In this reaction, a solvent may be used, which may be any solvent as far as it does not adversely affect the reaction, and includes, for example, water; amides such as N,N-dimethylformamide, N,N-dimethylacetamide and the like; sulfolane; nitriles such as acetonitrile and the like; ketones such as acetone and the like; sulfoxides such as dimethylsulfoxide and the like; alcohols such as methanol, ethanol and the like; ethers such as tetrahydrofuran, dioxane and the like; etc. These solvents may be used alone or in admixture of two or more.

This reaction is preferably effected in the presence of an acid, which includes, for example, hydrogen halides such as hydrogen chloride, hydrogen bromide and the like; mineral acids such as hydrochloric acid, hydrobromic acid and the like; organic acids such as p-toluenesulfonic acid, methanesulfonic acid and the like; etc.

The amount of the acid used is 0.5 to 50 moles per mole of the compound of the formula [I-13].

The above reaction may usually be carried out at a temperature of 0° to 150° C. for a period of 30 minutes to 24 hours.

By subjecting to reaction a compound of the formula [I-13] in which $R^{10}$ is

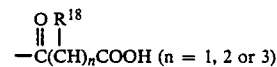

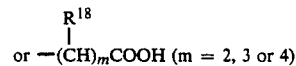

wherein $nR^{18}$'s or $mR^{18}$'s may be the same or different and hydrogen atoms or groups mentioned as substituents for $R^5$, according to the method stated in Organic Synthesis Col. vol. V, pp. 944–946, there can be obtained a compound of the formula [I] in which $R^6$ and $R^7$ form a 3- to 7-membered optionally substituted heterocyclic group with the nitrogen atom to which the two are bonded.

Production Process 11

The compound of the formula [I-16] can be obtained by reacting a compound of the formula [I-15] with a compound of the formula [34] or [35].

In this reaction, a solvent may be used, which may be any solvent as far as it does not adversely affect the reaction, and includes water and the solvents mentioned in Production Process 7(1).

The amount of the compound of the formula [34] or [35] used is 1 to 5 moles per mole of the compound of the formula [I-15].

The above reaction may usually be carried out at a temperature of $-20°$ to 150° C. for a period of 5 minutes to 24 hours.

Incidentally, when chlorosulfonyl isocyanate is used, the compound obtained by the reaction can be treated with a conventional acid to convert it to the objective compound of the formula [I-16].

Production Process 12

(1) The compound of the formula [I-17] can be obtained by reacting a compound of the formula [I-6] with a halogenating agent in an amount of 2 to 2.5 moles per mole of the compound of the formula [I-6].

This reaction can be effected in the same manner as stated in Production Process 7(1).

(2) The compound of the formula [I-18] can be obtained by reacting the compound of the formula [I-17] with a base.

In this reaction, a solvent may be used, which may be any solvent as far as it does not adversely affect the reaction, and includes, for example, halogenated hydrocarbons such as methylene chloride, 1,2-dichloroethane, chloroform and the like; alcohols such as methanol, ethanol and the like; esters such as ethyl acetate and the like; amides such as N,N-dimethylformamide and the like; sulfoxides such as dimethylsulfoxide and the like; pyridine; 2,6-lutidine and the like. These solvents may be used alone or in admixture of two or more.

The base used in this reaction includes, for example, organic bases such as triethylamine, pyridine, 2,6-lutidine, DBU; alkali metal carbonates such as sodium carbonate, potassium carbonate and the like.

The amount of the base used is 1 to 5 moles per mole of the compound of the formula [I-17].

The above reaction may usually be carried out at a temperature of 20° to 150° C. for a period of 10 minutes to 24 hours.

(3) The compound of the formula [I-19] can be obtained by reacting the compound of the formula [I-18] with a compound of the formula [36].

In this reaction, a solvent may be used, which may be any solvent as far as it does not adversely affect the reaction, and includes, for example, alcohols such as methanol, ethanol and the like; ethers such as tetrahydrofuran, diethyl ether, dioxane and the like; amides such as N,N-dimethylformamide and the like; sulfoxides such as dimethylsulfoxide and the like; water and the like. These solvents may be used alone or in admixture of two or more.

The amount of the compound of the formula [36] is 1 to 50 moles per mole of the compound of the formula [I-18].

The above reaction may usually be carried out at a temperature of $-20°$ to 80° C., preferably $-10°$ to 30° C. for a period of 30 minutes to 24 hours.

(4) The compound of the formula [I-20] can be obtained by acylating the compound of the formula [I-19] in which $R^6$ is a hydrogen atom in the same manner as stated in Production Process 10(1).

Production Process 13

(1) The compound of the formula [I-22] can be obtained by reacting the compound of the formula [I-21] with a halogenating agent in an amount of 0.9 to 1.5 moles per mole of the compound of the formula [I-21] in the same manner as stated in Production Process 7(1). obtained by acylating the compound of the formula [I-22] in the same manner as stated in Production Process 10(1).

(2) The compound of the formula [I-23] can be obtained by acylating the compound of the formula [I-22] in the same manner as stated in Production Process 10(1).

(3) The compound of the formula [I-24] can be obtained by reacting the compound of the formula [I-23] with a compound of the formula [37].

In this reaction, a solvent may be used, which may be any solvent as far as it does not adversely affect the reaction, and includes, for example, alcohols such as methanol, ethanol and the like; amides such as N,N-dimethylformamide and the like; sulfoxides such a dimethylsulfoxide and the like; ethers such as tetrahydrofuran, dioxane and the like; water; etc. These solvents may be used alone or in admixture of two or more.

In this reaction, a base may be used, which includes, for example, the organic bases mentioned in Production Process 12(2).

The amounts of the compound of the formula [37] and the base are each 1 to 3 moles per mole of the compound of the formula [I-23].

The above reaction may usually be carried out at a temperature of $-20°$ to 150° C. for a period of 30 minutes to 24 hours.

The compound of the formula [37] may be prepared in the reaction system.

Also, the compound of the formula [I-24] in which $R^{3c}$ is a cyano group can be converted into a compound of the formula [I-24] in which $R^{3c}$ is a carbamoyl, carboxyl or alkoxycarbonyl group by a conventionally known hydrolysis, esterification or the like.

The compound of the formula [I-24] in which $R^{3c}$ is an azido group can be converted into a compound of the formula [I-24] in which $R^{3c}$ is an amino group by a catalytic hydrogenation or a conventional reduction with hydrogen sulfide-triethylamine or the like.

Production Process 14

The compound of the formula [I-25] can be obtained by reacting a compound of the formula [I-8] with a compound of the formula [38].

This reaction may be effected by, for example, the method stated in Organic Synthesis Col. vol. V, pp. 716–719.

Production Process 15

The compound of the formula [I-26] can be obtained by reacting a compound of the formula [I-8] with a compound of the formula [39].

In this reaction, a solvent may be used, which may be any solvent as far as it does not adversely affect the reaction, and includes, for example, the solvents mentioned in Production Process 7(1); amides such as N,N-dimethylformamide, N-methylpyrrolidone and the like; sulfoxides such as dimethylsulfoxide and the like; ethers such as 1,2-diethoxyethane and the like; etc. These solvents may be used alone or in admixture of two or more.

In this reaction, a base may also be used, which includes, for example, organic bases such as triethylamine, pyridine and the like; inorganic bases such as sodium carbonate, potassium carbonate and the like; etc.

The amounts of the compound of the formula [39] and the base used are 1 to 10 moles and 1 to 2 moles, respectively, per mole of the compound of the formula [I-8].

The above reaction may usually be carried out at a temperature of $-20°$ to $150°$ C. for a period of 30 minutes to 10 hours.

Incidentally, when a compound of the formula [39] in which $R^{6a}$ a substituted or unsubstituted phenyl group is used, there may further be added alkali iodides such as sodium iodide, potassium iodide or the like; copper powder; a copper compound such as cuprous oxide, cuprous chloride or the like alone or in admixture of two or more as a reaction-accelerating agent. The amounts thereof are each 0.01 to 2 moles per mole of the compound of the formula [I-8].

The above reaction may usually be carried out at a temperature of $100°$ to $200°$ C. for a period of 1 to 15 hours.

Production Process 16

The compound of the formula [I-28] can be obtained by subjecting a compound of the formula [I-27] to nitration.

In this reaction, a solvent may be used, which includes, for example, acetic acid, acetic anhydride and the like.

The nitrating agent used in this reaction includes conc. nitric acid, fuming nitric acid and the like, and the amount thereof is 1 to 5 moles per mole of the compound of the formula [I-27].

The above reaction may usually be carried out at a temperature of $0°$ to $150°$ C. for a period of 10 minutes to 24 hours.

Production Process 17

The compound of the formula [I-29] can be converted into a compound of the formula [I-8] by a conventional reduction of nitro group.

Production Process 18

The compound of the formula [I-31] can be obtained by reacting a compound of the formula [I-30] or a reactive derivative thereof with a compound of the formula [36].

The reactive derivative of the compound of the formula [I-30] includes, for example, acid halides, acid anhydrides, mixed acid anhydrides, active esters, active acid amides and reactive derivatives obtained by reacting the compound of the formula [I-30] with a Vilsmeier reagent.

In this reaction, a solvent may be used, which may be any solvent as far as it does not adversely affect the reaction, and includes, for example, water; halogenated hydrocarbons such as methylene chloride, 1,2-dichloroethane, chloroform and the like; alcohols such as methanol, ethanol and the like; ethers such as diethyl ether, tetrahydrofuran, dioxane and the like; aromatic hydrocarbons such as benzene, toluene and the like; amides such as N,N-dimethylformamide, N,N-dimethylacetamide and the like; nitriles such as acetonitrile and the like; esters such as ethyl acetate and the like; pyridine; 2,6-lutidine; etc. These solvents may be used alone or in admixture of two or more.

In this reaction, a base may be used, which includes, for example, organic bases such as triethylamine, DBU, pyridine and the like; alkali metal hydroxides such as sodium hydroxide, potassium hydroxide and the like; alkali metal carbonates such as sodium carbonate, potassium carbonate and the like; etc. Further, the compound of the formula [36] may be used as the base, too.

Also, when the compound of the formula [I-30] is used in the form of a free acid or a salt with a nitrogen-containing organic base, the above reaction may be conducted with an appropriate condensing agent.

The condensing agent used includes, for example, N,N'-di-substituted carbodiimides such as N,N'-dicyclohexylcarbodiimide and the like.

The amount of the compound of the formula [36] used is 1 to 50 moles per mole of the compound of the formula [I-30] or its reactive derivative.

The above reaction may usually be carried out at a temperature of $-20°$ to $150°$ C. for a period of 30 minutes to 24 hours.

Production Process 19

The compound of the formula [I-33] can be obtained by hydrolyzing a compound of the formula [I-32] with an acid.

In this reaction, a solvent may be used, which may be any solvent as far as it does not adversely affect the reaction, and includes, for example, water and organic carboxylic acids such as formic acid, acetic acid and the like. These solvents may be used alone or in admixture of two or more.

The acid used in this reaction includes, for example, mineral acids such as hydrochloric acid, sulfuric acid and the like; hydrogen chloride; hydrogen bromide; polyphosphoric acid; formic acid; Lewis acids such as boron trifluoride, titanium tetrachloride and the like; etc.

The amount of the acid used is 5 to 100 moles per mole of the compound of the formula [I-32].

The above reaction may usually be carried out at a temperature of 20° to 150° C. for a period of 30 minutes to 24 hours.

The starting compounds and intermediate compounds may be used in the form of salts and the definition of the salt of the compound of the formula [I] mentioned above can also be applied to the salts.

The starting compounds in this invention can be produced by, for example, the following production methods:

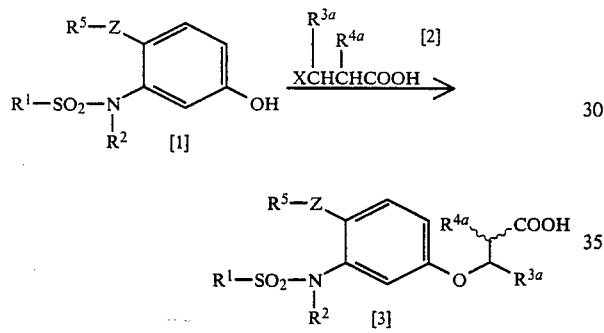

-continued
Production process F

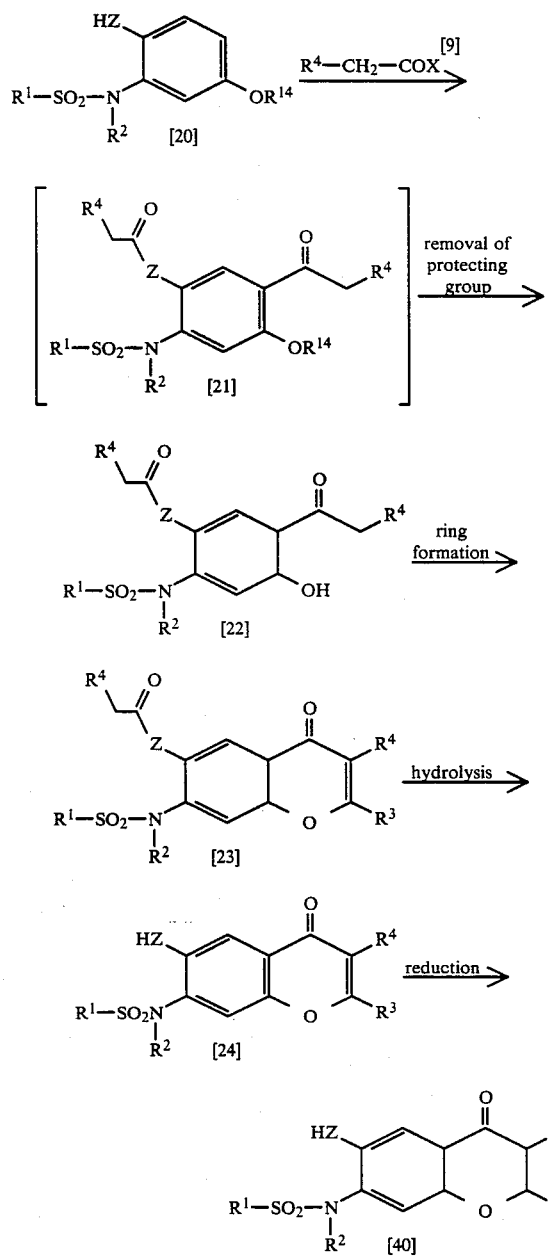

Production process G

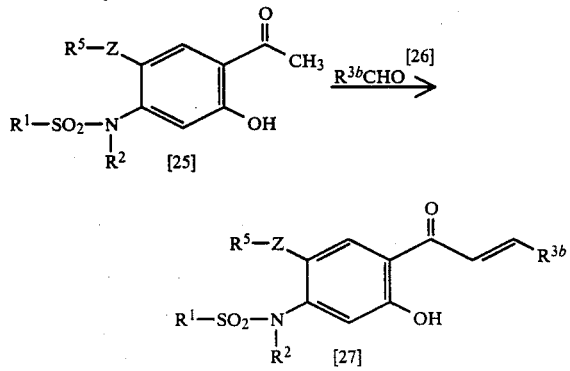

Production Process H

-continued

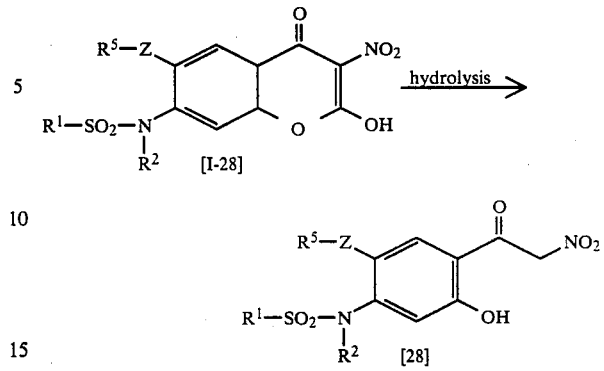

In the above formulas, Z, $R^1$, $R^2$, $R^3$, $R^{3a}$, $R^{3b}$, $R^4$, $R^{4a}$, $R^{4b}$, $R^5$, $R^{12}$, X and $\sim$ have the same meanings as defined above; $R^{13}$ means a halogen atom or a removable group such as an alkylsulfonyloxy or arylsulfonyloxy group or the like; $R^{14}$ means a hydroxyl-protecting group; $R^{15}$ means an acyl group; and $R^{16}$ means a hydrogen atom or a hydroxyl-protecting group.

The hydroxyl-protecting group includes, for example, lower alkyl groups such as methyl, ethyl and the like and aralkyl groups such as benzyl and the like.

Incidentally, the starting compounds and intermediates in the above reactions may also be used in the form of salts, and the definition of salt of the compound of the formula [I] mentioned above can also be applied to the salts.

Each production process is explained in detail below.

Production Process A

The compound of the formula [3] can be produced by reacting a compound of the formula [1] with a compound of the formula [2] in the presence of a base.

In this reaction, a solvent may be used, which may be any solvent as far as it does not adversely affect the reaction, and includes, for example, water, N,N-dimethylformamide, N,N-dimethylacetamide, dimethylsulfoxide or a mixture of water with an organic solvent (e.g., N,N-dimethylformamide, dioxane, methanol, ethanol or the like).

The base used in the above reaction includes alkali metal hydroxides such as sodium hydroxide, potassium hydroxide and the like; alkali metal alkoxides such as sodium methoxide, sodium ethoxide, potassium tert-butoxide and the like; alkali metal hydrides such as sodium hydride, potassium hydride and the like.

A β-propiolactone or its derivative may be substituted for the compound of the formula [2].

The amounts of the base and the compound of the formula [2] used are 1 to 10 moles and 1 to 5 moles, respectively, per mole of the compound of the formula [1].

The above reaction may be effected at a temperature of 20° to 100° C. for a period of 30 minutes to 24 hours.

The compound of the formula [1] which is the starting material can be obtained by subjecting a 3-nitrophenol having a $R^5$—Z— group in the 4-position in which $R^5$ and Z have the same meanings as defined above (see Japanese Patent Application Kokai No. 203,079/82) to conventional reduction of nitro group and sulfonylation which is mentioned hereinbefore in connection with Production Process 4.

Production Process B (1) The compound of the formula [6] can be obtained by reacting a compound of the formula [1] with a compound of the formula [4] or [5] in the presence of a base In this reaction, a solvent may be used, which may be any solvent as far as it does not adversely affect the reaction, and includes, for example, amides such as N,N-dimethylformamide and the like; sulfoxides such as dimethylsulfoxide and the like; HMPA; halogenated hydrocarbons such as methylene chloride, 1,2-dichloroethane, chloroform and the like. These solvents may be used alone or in admixture of two or more.

The base used in the above reaction includes metallic alkalis such as metallic sodium, metallic potassium and the like; alkali metal hydrides such as sodium hydride, potassium hydride and the like; alkali metal alkoxide such as sodium methoxide, sodium ethoxide, potassium tert-butoxide and the like; alkali metal carbonates such as sodium carbonate, potassium carbonate and the like; organic amines such as triethylamine, DBU, pyridine and the like; etc.

The amounts of the compounds of the formula [4] or [5] and the base are each 1 to 5 moles per mole of the compound of the formula [1].

The above reaction may be carried out at a temperature of $-20°$ to $150°$ C. for a period of 30 minutes to 24 hours The compound of the formula [6] obtained by the above reaction includes cis-form, trans-form and a mixture of the two, and all of the cis-form, trans-form and mixture may be used as such in the subsequent reaction.

(2) The compound of the formula [7] can be obtained by hydrolyzing the compound of the formula [6].

A solvent may be used in this reaction, which may be any solvent as far as it does not adversely affect the reaction, and includes, for example, water and mixtures of water with organic solvents such as alcohols, for example, methanol, ethanol and the like and ethers, for example, dioxane, tetrahydrofuran and the like.

This hydrolysis may usually be conducted with an inorganic base such as sodium hydroxide, potassium hydroxide or the like.

The amount of the inorganic base used is 1 to 50 moles per mole of the compound of the formula [6].

The above reaction may usually be carried out at a temperature of $0°$ to $100°$ C. for a period of 30 minutes to 24 hours When $R^{4a}$ is an alkoxycarbonyl group, the compound of the formula [6] may be directly subjected to the same ring closure reaction as stated in Production Process 2(1) to obtain a compound of the formula [I-3].

Production Process C (1) The compound of the formula [10] can be obtained by reacting a compound of the formula [8] with a compound of the formula [9] in the presence of a Lewis acid such as aluminum chloride, boron trifluoride or the like.

In this reaction, a solvent may be used, which may be any solvent as far as it does not adversely affect the reaction, and includes, for example, halogenated hydrocarbons such as methylene chloride, 1,2-dichloroethane and the like; organic carboxylic acids such as acetic acid and the like; carbon disulfide; nitrobenzene; etc. These solvents may be used alone or in admixture of two or more.

The amounts of the compound of the formula [9] and the Lewis acid used are 1 to 1.2 moles and 1 to 5 moles, respectively, per mole of the compound of the formula [8].

The above reaction may usually be carried out at a temperature of $0°$ to $150°$ C. for a period of 30 minutes to 24 hours.

Moreover, the compound of the formula [11] can be obtained by subjecting a compound of the formula [10] to conventional removal of protecting group.

The compound of the formula [8] can also be prepared, for example, by subjecting a 3-nitroanisole having a $R^5$—Z— group in which $R^5$ and Z have the same meanings as defined above to conventional reduction of nitro group and then to sulfonylation [refer to J. Chem. Soc., 581-588 (1960); Helv. Chim. Acta..61, 2452-2462 (1978); J. Chem. Soc., 885-889 (1959); Helv. Chim. Acta. 48, 336-347 (1965) and Chemical Abstracts, 40, 2806 (3) (1946)].

Production Process D

The compound of the formula [15] can be obtained by reacting a compound of the formula [12] with a compound of the formula [2] according to the methods stated in Production Process 1 and Production Process A to obtain a compound of the formula [13], then subjecting the compound of the formula [13] to ring closure and subjecting the compound of the formula [14] thus obtained to dehydrogenation.

The compound of the formula [16a] can be obtained by subjecting the compound of the formula [15] to deacylation reaction in the presence of an acid catalyst.

In this reaction, a solvent may be used, which includes water and mixtures of water with organic solvents such as methanol, ethanol, dioxane, tetrahydrofuran and the like.

The acid catalyst used in this reaction includes mineral acids such as hydrochloric acid, sulfuric acid and the like and organic acids such as paratoluenesulfonic acid and the like.

The amount of the acid catalyst is 0.1 to 50 moles per mole of the compound of the formula [15].

The above reaction may usually be carried out at a temperature of $0°$ to $150°$ C. for a period of 30 minutes to 24 hours.

Production Process E

The compound of the formula [19] can be obtained by reacting a compound of the formula [17] with a compound of the formula [18] in the presence of a base.

In this reaction, a solvent may be used, which may be any solvent as far as it does not adversely affect the reaction, and includes, for example, aromatic hydrocarbons such as benzene, toluene, xylene and the like; amides such as N,N-dimethylformamide and the like; alcohols such as methanol, ethanol and the like; etc. The compound of the formula [18] may also be used as the solvent.

The base used in this reaction includes, for example, metallic alkalis such as metallic sodium, metallic potassium and the like; alkali metal amides such as sodium amide, potassium amide and the like; alkali metal alkoxides such as sodium methoxide, sodium ethoxide, potassium tert-butoxide and the like; alkali hydrides such as sodium hydride, potassium hydride and the like; etc.

The amounts of the base and the compound of the formula [18] used are 1 to 10 moles and 1 to 100 moles, respectively, per mole of the compound of the formula [17].

The above reaction may usually be carried out at a temperature of 20° to 150° C. for a period of 30 minutes to 24 hours When $R^{16}$ is a hydroxyl-protecting group, the compound of the formula [19] can also be produced by reacting the compound of the formula [17] with the compound of the formula [18] in the same manner as mentioned above and then subjecting the reaction product to conventional removal of protecting group.

The compound of the formula [17] can be obtained by reacting a compound of the formula [1] with boron trifluoride-acetic acid, aluminum chloride-acetic anhydride or the like.

This reaction is effected by applying the Fries rearrangement reaction according to the method described in, for example, Chem. Ber., vol. 95, p. 1413 (1962), Jean Mathieu, Jean Weill-Raynal, "Formation of C—C Bonds", vol. III, pp. 384–453 published by Geoge Thieme Publishers, or the like.

Production Process F (1) The compound of the formula [21] can be obtained by reacting a compound of the formula [20] with a compound of the formula [9] in the presence of a Lewis acid such as aluminum chloride, boron trifluoride or the like.

In this reaction, a solvent may be used, which may be any solvent as far as it does not adversely affect the reaction, and includes, for example, halogenated hydrocarbons such as methylene chloride, 1,2-dichloroethane and the like; carbon disulfide; nitrobenzene; and the like. These solvents may be used alone or in admixture of two or more.

The amounts of the compound of the formula [9] and the Lewis acid are 2 to 10 moles and 2 to 5 moles, respectively, per mole of the compound of the formula [20].

The above reaction can be carried out at a temperature of 0° to 150° C. for a period of 30 minutes to to 24 hours.

Moreover, the compound of the formula [22] can be obtained by subjecting the compound of the formula [21] to conventional removal of protecting group.

(2) The compound of the formula [23] can be obtained by subjecting the compound of the formula [22] to the same reaction as in Production Process 3.

Furthermore, the compound of the formula [24] can be obtained by subjecting the compound of the formula [23] to conventional hydrolysis.

(3) The compound of the formula [40] can be obtained by subjecting the compound of the formula [24] to the same reaction as in Production Process 2(2).

The compound of the formula [20] can also be obtained by subjecting, for example, 3-nitroanisole having a H—Z— group in which Z has the same meaning as defined above to conventional reduction of nitro group and then to sulfonylation which is mentioned hereinbefore in connection with Production Process 4.

Production Process G (1) The compound of the formula [27] can be obtained by reacting a compound of the formula [25] with a compound of the formula [26] in the presence of a base.

In this reaction, a solvent may be used, which may be any solvent as far as it does not adversely affect the reaction, and includes, for example, water; alcohols such as methanol, ethanol and the like; etc. These solvents may be used alone or in admixture of two or more.

The base used in the above reaction includes, for example, alkali metal hydroxides such as sodium hydroxide, potassium hydroxide and the like; alkali metal alkoxides such as sodium methoxide, sodium ethoxide, potassium tert-butoxide and the like; etc.

The amounts of the base and the compound of the formula [26] used are 1 to 10 moles and 1 to 100 moles, respectively, per mole of the compound of the formula [25].

The above reaction may usually be carried out at a temperature of 0° to 100° C. for a period of 30 minutes to 24 hours.

Production Process H

The compound of the formula [28] can be obtained by hydrolyzing the compound of the formula [I-28] with an alkali metal hydroxide such as sodium hydroxide, potassium hydroxide or the like.

In this reaction, a solvent may be used, which may be any solvent as far as it does not adversely affect the reaction, and includes, for example, water and alcohols such as methanol, ethanol and the like. These solvents may be used alone or in admixture of two or more.

The amount of the alkali hydroxide used in this reaction is 2 to 50 moles per mole of the compound of the formula [I-28].

The above reaction may usually be carried out at a temperature of 0° to 100° C. for a period of 30 minutes to 24 hours.

In addition to the production processes mentioned above, the compound of the formula [I] can be obtained by reacting a compound of the formula [I-8] with (i) an alkyl iminoacetate or iminoacetic acid chloride, (ii) cyanamide or (iii) an alkylisothiourea by the method described in the following three literature references (i) to (iii), respectively.

(i) Synthetic Organic Chemistry published by John Wiley & Sons, Inc., 1953, pp. 634–639
(ii) Ann. 442, p. 144 (1925)
(iii) Organic Synthesis Col., vol. III, pp. 440–442.

Moreover, the compound of this invention and the starting compounds therefor can be converted to another objective compound and another starting compound, respectively, by subjecting them to appropriate combination of conventional oxidation, reduction, dehydration, hydrolysis, halogenation, alkylation, acylation, amidation, alkylsulfonylation, alkenylsulfonylation, arylsulfonylation, esterification, imination, dealkylation, formation of heterocyclic ring and the like.

The compounds of the formula [I] in which $R^3$, $R^4$ and $R^5$ are or have aldehyde, acyl, cyano, carbamoyl or carboxyl groups can be converted to other objective compounds. For example, the compounds of the formula [I] in which $R^3$, $R^4$ and $R^5$ are or have aldehyde groups can be converted to other objective compounds in which $R^3$, $R^4$ and $R^5$ are or have carboxyl, nitrile, halogen, nitr or hydroxyl groups according to the methods described in Tetrahedron Lett., 1187–1190 (1974); Synth. Comm., 10, 889–895 (1980); Tetrahedron, 30, 3563–3568 (1974); Curr. Sci., 49, 18–19 (1980); Tetrahedron Lett., 1995–1998 (1973); U.S. Pat. Nos. 4,196,128 and 3,906,005, AU. 516,897 and the like.

Also, the compounds of the formula [I] in which $R^3$, $R^4$ and $R^5$ are or have acyl groups can be converted to the compounds in which $R^3$, $R^4$ and $R^5$ are or have alkenyl groups by, for example, the Witting reaction.

This reaction can be effected according to the method stated in Organic Reaction, 14, 270–490. Alternatively, the acyl group can be covered to a corresponding alcohol by the Grignard reaction. This reaction can be effected according to the method described in Jikken Kagaku Kouza, vol. 18, editted by Japan Chemical Society, Yuuki Kagoubutsu no Hannou (Reaction of Organic Chemistry), pp. 363–408 published by Maruzen.

The compounds of the formula [I] in which $R^3$, $R^4$ and $R^5$ are or have carboxyl groups can be converted to those in which $R^3$, $R^4$ and $R^5$ are or have amino or alkoxycarbonylamino groups by the Curtius rearrangement. This reaction can be effected according to the method described in Organic Reaction, 3, 337–449.

When the above-mentioned compounds have hydroxyl, amino or carboxyl groups, these groups may be protected by the protecting groups mentioned in, for example, T. W. Green, Protective Groups in Organic Synthesis (1981) published by John Wiley & Sons, Inc.

The compound of the formula [I] can be administered orally or parenterally in a conventional manner in the form of capsules, powders, granules, pills, tablets, suspensions, emulsions, solutions, cataplasms, ointments, injections, eye drops, liniments, syrups or suppositories. Also, the administration method, dose and number of administration times can be appropriately varied depending upon the age and symptom of a patient. Usually, the compound may be administered in several portions a day in a dose of about 5.0 to about 1,000 mg per adult.

The compounds of this invention shown in Table 1 were subjected to the following tests to obtain the results shown in each test item.

TABLE 1

| Compound No. | $R^1$ | $R^2$ | $R^3$ | $R^4$ | $R^5$ | Z |
|---|---|---|---|---|---|---|
| 1 | CH$_3$— | H | H | H | C$_6$H$_5$— | O |
| 4 | CH$_3$— | H | H | CH$_3$S— | C$_6$H$_5$— | O |
| 12 | CH$_3$— | H | H | H | C$_6$H$_5$— | NH |

TABLE 1-continued

| Compound No. | R¹ | R² | R³ | R⁴ | R⁵ | Z |
|---|---|---|---|---|---|---|
| 34 | CH₃— | H | H | HN—CHO | 2-F-C₆H₄ | O |
| 39 | CH₃— | H | H | HN—CHO | 2,4-F₂-C₆H₃ | O |
| 40 | ClCH₂— | H | H | HN—CHO | C₆H₅ | O |
| 46 | CH₃— | H | H | HN—CHO | 2-CH₃-C₆H₄ | O |
| 61 | CH₃— | H | CH₃— | H₂NC(O)— | C₆H₅ | O |
| 88 | CH₃— | H | H | HN—CHO | C₆H₅ | S |
| 94 | CH₃— | H | H | H | 2,4-F₂-C₆H₃ | O |
| 9 | CH₃— | H | CH₃— | H | C₆H₅ | O |
| 96 | CH₃— | CH₃C(O)— | H | H | C₆H₅ | O |
| 99 | CH₃— | H | H | HN—CHO | C₆H₅ | O |
| 100 | CH₃— | H | H | CH₃N—CHO | C₆H₅ | O |

TABLE 1-continued

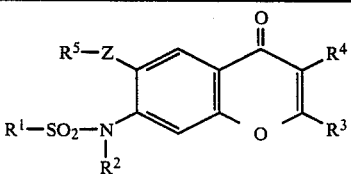

| Compound No. | R¹ | R² | R³ | R⁴ | R⁵ | Z |
|---|---|---|---|---|---|---|
| 101 | CH₃— | H | H | NH—<br>\|<br>CH₃ | —⟨phenyl⟩— | O |
| 122 | CH₃— | H | H | H₂NC—<br>‖<br>O | —⟨phenyl⟩— | O |

1. Anti-inflammatory activity (1) Carrageenin-induced paw edema

This inhibitory activity was tested according to the method of C. A. Winter et al. [Proceedings of the Society for Experimental Biology and Medicine, vol. 111, p. 544 (1962)].

To male rats of Donryu strain (body weight: 90–120 g, 6 to 7 rats per group) which had been fasted overnight was orally administered a test compound suspended in 0.5% (w/v) aqueous carboxylmethylcellulose solution in a proportion of 1 ml/100 g of body weight. After one hour, 0.1 ml of a 1% carrageenin was injected into the subplantar region of the left hind paw. Three hours after carrageenin injection, the paw volume was measured plethysmographically and the percent swelling was determined from the volume before injection and the inhibitory percentage was calculated according to the following equation:

$$\text{Inhibition (\%)} = \left(1 - \frac{\text{Percent swelling in test compound-administered group}}{\text{Percent swelling in control group}}\right) \times 100$$

The result is shown in Table 2 in terms of inhibitory effect indicated below based on the inhibition (x%).

| | | | |
|---|---|---|---|
| —: | x < 10, | ±: | 10 ≦ x < 15, |
| +: | 15 ≦ x < 20, | ++: | 20 ≦ x < 30 |
| +++: | 30 ≦ x < 40, | ++++: | x ≧ 40. |

TABLE 2

Inhibitory Activity against Carrageenin-Induced Paw Edema

| Compound No. | Dose (mg/kg) | Inhibitory effect |
|---|---|---|
| 1 | 10 | +++ |
| 4 | 10 | ++ |
| 12 | 10 | +++ |
| 34 | 10 | ++++ |
| 39 | 10 | ++++ |
| 40 | 10 | ++++ |
| 46 | 10 | ++++ |
| 61 | 10 | + |
| 88 | 10 | +++ |

TABLE 2-continued

Inhibitory Activity against Carrageenin-Induced Paw Edema

| Compound No. | Dose (mg/kg) | Inhibitory effect |
|---|---|---|
| 94 | 10 | +++ |
| 9 | 10 | ++ |
| 96 | 10 | +++ |
| 99 | 10 | ++++ |
| 100 | 10 | ++++ |
| 101 | 10 | +++ |
| 122 | 10 | ++ |
| IM* (control) | 10 | ++++ |

Note:
IM* refers to indomethacin.

(2) Adjuvant-induced arthritis

This inhibitory activity was tested according to the method of E. M. Glenn [American Journal of Veterinary Research, vol. 27, p. 339 (1966)].

To male rats of Westar-Lewis strain (body weight: 190–230 g, 5 rats per group) was intradermally injected 0.1 ml of a suspension of heat-killed Mycobacterium tuberculosis in liquid paraffin at a concentration of 6 mg/ml as the adjuvant into the root of tail. Eighteen days after the adjuvant injection, the rats were classified based on the volume of both hind paws, and then a suspension of the test compound in 0.5% (w/v) aqueous carboxymethylcellulose solution was orally administered to the classified rats in a proportion of 1 ml/100 g of body weight once a day for seven continuous days (see Table 3) or four continuous days (see Table 4). On the day following the last administration, the volume of both hind paws was measured, and in the same manner as in (1) above, the inhibitory effect was determined. Incidentally, the result is shown in Tables 3 and 4 in terms of the inhibitory effect indicated below based on inhibition (x%).

| Inhibition (x %) | | | |
|---|---|---|---|
| —: | x < 10, | ±: | 10 ≦ x < 15, |
| +: | 15 ≦ x < 20, | ++: | 20 ≦ x < 30, |
| +++: | 30 ≦ x < 40, | ++++: | x ≧ 40. |

TABLE 3

Inhibitory Activity against Adjuvant Arthritis

| Compound No. | Dose (mg/kg) | Inhibitory effect |
|---|---|---|
| 1 | 10 | +++ |
| 94 | 10 | ++++ |
| 9 | 10 | ++++ |
| 96 | 10 | ++++ |
| IM* (control) | 1 | +++ |

Note
IM* refers to indomethacin.

TABLE 4

Inhibitory Activity against Adjuvant Arthritis

| Compound No. | Dose (mg/kg) | Inhibitory effect |
|---|---|---|
| 4 | 3 | ++ |
| 12 | 3 | +++ |
| 34 | 3 | +++ |
| 39 | 3 | ++ |
| 40 | 3 | ++ |
| 46 | 3 | ++ |
| 61 | 10 | +++ |
| 88 | 10 | ++ |
| 99 | 3 | ++ |
| 100 | 10 | ++ |
| 101 | 10 | ++ |
| 122 | 3 | ++ |
| IM* (control) | 3 | +++ |

Note:
IM* refers to indomethacin.

2. Ulcerogenic Effect

To male rats of Wister strain (body weight: 180–230 g, 7 to 8 rats per group) which had been fasted for 24 hours with free access to water was orally administered a test compound suspended in 0.5% (w/v) aqueous carboxymethylcellulose solution in a proportion of 1 ml/100 g of body weight. The rats were allowed to stand under abstinence from food and water for 24 hours, and thereafter, sacrificed by dislocation of cervical vertebrae, after which the stomach was removed and fixed in 1% (v/v) formaline solution for 30 minutes. This stomach was split along the greater curvature and the length (mm) of the erosion and ulcer formed on the gastric mucosa was measured by a stereomicroscope, and the total sum of the lengths (lmm) was determined, from which ulcerogenic index was assessed based on the following arbitrary scale:

| | |
|---|---|
| 0  l < 0.5, | 1  0.5 ≦ l < 1, |
| 2  1 ≦ l < 2, | 3  2 ≦ l < 3, |
| 4  3 ≦ l < 5, | 5  5 ≦ l < 7, |
| 6  7 ≦ l < 10, | 7  10 ≦ l < 15, |
| 8  15 ≦ l < 25, | 9  25 ≦ l < 40, |
| 10  l ≧ 40. | |

Subsequently, $UD_{50}$ (mg/kg) which is the dose of the test compound which induces ulcerogenic index 5 was determined on each test compound.

The results obtained are shown in Table 5.

TABLE 5

Ulcerogenic Activity

| Compound No. | $UD_{50}$ (mg/kg) |
|---|---|
| 1* | >300 |
| 34 | >500 |
| 39 | >500 |
| 46 | >500 |
| 94* | >300 |
| 99 | >500 |
| IM (Control) | 4.3 |

Note:
*Rats were allowed to stand for 5 hours under abstinence from food and water and then tested.

3. Acute toxicity

ICR strain male mice (body weight: 20–25 g, weeks old, 3 mice per group) were tested for oral acute toxicity. A test compound suspended in 0.5% (w/v) aqueous carboxymethylcellulose solution was orally administered to the mice in a proportion of 0.2 ml/10 g of body weight. After the administration, general symptom was observed over one week. With Test Compounds Nos. 1, 34, 39, 46, 94 and 99 no death case was found even at a dose of 500 mg/kg, and no behavioural changes were observed.

$LD_{50}$ values of these test compounds were >500 mg/kg.

Incidentally, $LD_{50}$ value of indomethacin was 25 mg/kg.

From the above results, it can be seen that the compound of this invention has excellent pharmacological effect and high safety, and has a very broad safety region as compared with indomethacin. Accordingly, it is clear that the compound of this invention has excellent pharmacological effect or high safety.

Next, this invention is illustrated by way of Reference Examples and Examples but is not limited to these Examples.

In the Examples, the mixing ratio of solvent is by volume in all cases, and the carrier in column chromatography is a silica gel produced by Merck Co. (Kieselgel 60, Art. 7734).

Also in the Examples, the following abbreviations are used:
Me Methyl
Et Ethyl
i-Pr: Isopropyl
Ac Acetyl
IPA: Isopropyl alcohol
IPE: Diisopropyl ether
Bz Benzoyl
DMF: N,N-Dimethylformamide
DMSO: Dimethylsufoxide
t-Bu: tert-Butyl The substance shown in [] shows a recrystallization solvent.

REFERENCE EXAMPLE 1

(1) 120 ml of ethanol and 120 ml of water were added to 23.1 g of 3-nitro-4-phenoxyphenol, and the mixture was made into a solution by heating at 60° C. 2.3 ml of 4N hydrochloric acid was added thereto. While maintaining the reaction temperature at 65°–70° C., 16.8 g of an iron powder was added thereto in portions in 20 minutes. Stirring was conducted for 30 minutes at the same temperature. The reaction mixture was hot-filtered. 50 ml of water was added to the filtrate and the mixture was allowed to stand. The resulting crystal was collected by filtration to obtain 16.5 g (yield: 82.1%) of 3-amino-4-phenoxyphenol having a melting point of 156°–157° C.

IR (KBr) cm$^{-1}$: 3400, 3320, 1590, 1453, 1230

The compounds shown in Table 6 were obtained in the same manner.

TABLE 6

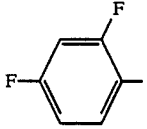

| $R^5$ | Z | Melting point (°C.) | IR(KBr) cm$^{-1}$ |
|---|---|---|---|
| 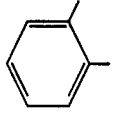 | O | 147.1–147.8 [aqueous ethanol] | 3400, 3325, 3080, 1600, 1500, 1460 |
| 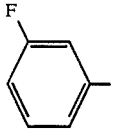 | O | 113.5–115 [50% aqueous ethanol] | 3390, 3325, 1595, 1490, 1450, 1205 |
| 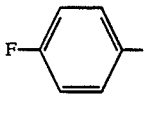 | O | 130–131 [50% aqueous ethanol] | 3390, 3300, 1590, 1500, 1440, 1205 |
| 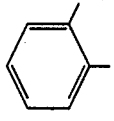 | O | 154–155 [50% aqueous ethanol] | 3390, 3300, 1585, 1495, 1460, 1210 |
| 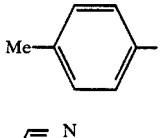 | O | 138–139 [IPE-n-hexane] | 3380, 3300, 1585, 1500, 1480, 1445, 1225, 1205, 1175 |
| 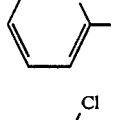 | O | 160–163 [Benzene] | 3380, 3300, 1600, 1490, 1450, 1220, 1200 |
| 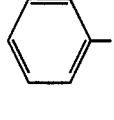 | S | 141–143 | 3475, 3360, 1610, 1570, 1210 |
| 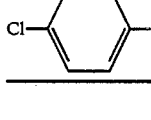 | O | Oily | (Neat) 3480, 3375, 1620, 1505, 1470, 1230, 1210 |
| 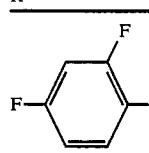 | O | Oily | (Neat) 3480, 3375, 1620 |

(2) 20.1 g of 3-amino-4-phenoxyphenol and 23.7 g of pyridine were dissolved in 200 ml of methylene chloride. To the resulting solution being ice-cooled was dropwise added a solution of 12.6 g of methanesulfonyl chloride in 60 ml of methylene chloride, at the same temperature in 30 minutes. The mixture was subjected to reaction at the same temperature for 2 hours. 200 ml of water was added thereto and then 4N hydrochloric acid was added to adjust the pH to 3. The organic layer was separated, washed with water and a saturated aqueous sodium chloride solution in this order, and then dried with anhydrous magnesium sulfate. Thereafter, the organic layer was subjected to distillation under reduced pressure to remove the solvent. The resulting crystal was recrystallized from benzene to obtain 23.7 g (yield: 84.9%) of 3-methylsulfonylamino-4-phenoxyphenol having a melting point of 138°–140° C.

IR (KBr) cm$^{-1}$: 3440, 3250, 1318, 1215, 1150

The compounds shown in Table 7 were obtained in the same manner.

TABLE 7

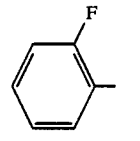

| $R^5$ | Z | Melting point (°C.) | IR(KBr) cm$^{-1}$: |
|---|---|---|---|
| 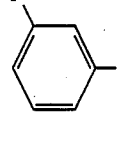 | O | 158.9–159.7 [Benzene] | 3460, 3250, 1600, 1487 |
| 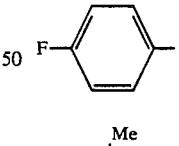 | O | 131–132 [Benzene] | 3450, 3270, 1320, 1200, 1140 |
| 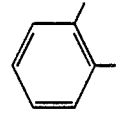 | O | 118–119 [Benzene] | 3440, 3250, 1590, 1310, 1210, 1150 |
| 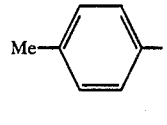 | O | 159–160 [Benzene] | 3460, 3250, 1600, 1487 |
| 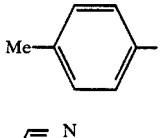 | O | 111–116 [Toluene-n-hexane] | 3380, 3200, 1600, 1490, 1300, 1265, 1230, 1195, 1150, 1140, 1110 |
| 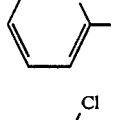 | O | 101–103 [Toluene] | 3425, 3250, 1600, 1490, 1390, 1320, 1220, 1150 |
| 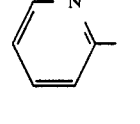 | S | 169–170.5 | 3300, 1575, 1445, 1330, 1150 |

TABLE 7-continued

[Structure: R⁵-Z-benzene ring with MeSO₂-NH at one position and OH at another]

| R⁵ | Z | Melting point (°C.) | IR(KBr) cm⁻¹: |
|---|---|---|---|
| *CF₃-phenyl | O | Oily | (Neat) 3400, 3250, 1500, 1440, 1320, 1275, 1215, 1160 |
| *N-pyridyl | O | 176–177 [IPA] | 3260, 1470, 1420, 1330, 1245, 1165, 1150 |
| 2-Cl-phenyl | O | 118–119 [Ethanol] | 3280, 1610, 1500, 1390, 1330, 1220, 1150 |
| 4-Cl-phenyl | O | 108–109 [Toluene] | 3240, 1490, 1475, 1380, 1320, 1215, 1155 |

*These were obtained in the same manner as in Reference Example 1 (1) and (2).

REFERENCE EXAMPLE 2

20.1 g of 3-amino-4-phenoxyphenol was dissolved in 60 ml of acetic acid. 30 ml of acetic anhydride was added thereto with ice cooling. Stirring was conducted at 20°-25° C. for 1 hour. The mixture was subjected to distillation under reduced pressure to remove the solvent. The resulting crystal was recrystallized from toluene to obtain 22.6 g (yield: 93%) of 3-acetylamino-4-phenoxyphenol having a melting point of 151°-153° C.

IR (KBr) cm⁻¹: 3440, 3190, 1665, 1605, 1540, 1450, 1238, 1215

REFERENCE EXAMPLE 3

(1) 3-Nitro-4-phenoxyanisole was subjected to the same reaction as in Reference Example 1 (1) to obtain the following compound:

3-Amino-4-phenoxyanisole

Melting point: 111°-113° C. (recrystallized from 50% aqueous ethanol)

IR (KBr) cm¹: 3455, 3350, 1618, 1500, 1475, 1215,

NMR (CDCl₃)δ: 3.61 (2H, bs), 3.77 (3H, s), 6.12–7.45 (8H, m)

(2) 21.5 g of 3-amino-4-phenoxyanisole and 11.1 g of triethylamine were added to 220 ml of methylene chloride, and the mixture was cooled to −40° C. Thereto was dropwise added a solution of 31.0 g of trifluoromethanesulfonic anhydride in 60 ml of methylene chloride, in 30 minutes. Then, stirring was conducted at −40° C. for 1 hour. 200 ml of water was added thereto and the resulting organic layer was separated. The organic layer was washed with a saturated aqueous sodium chloride solution and dried with anhydrous magnesium sulfate. Thereafter, the organic layer was subjected to distillation under reduced pressure to remove the solvent. To the resulting crystal was added n-hexane. The mixture was filtered to obtain 25.8 g (yield: 74.4%) of 4-phenoxy-3-trifluoromethylsulfonylaminoanisole.

Melting point: 57°-58° C.

IR (KBr) cm⁻¹: 3260, 1500, 1370, 1235, 1215, 1190,

NMR (CDCl₃)δ: 3.79 (3H, s), 6.58–7.48 (9H, m)

(3) 34.7 g of 4-phenoxy-3-trifluoromethylsulfonylaminoanisole and 31 g of ethanethiol were dissolved in 350 ml of methylene chloride. The resulting solution was then ice-cooled. Thereto was added 27 g of aluminum chloride at the same temperature in 30 minutes. Stirring was conducted for 30 minutes at 5°-10° C. The reaction mixture was poured into 300 ml of ice water and the resulting organic layer was separated. The organic layer was washed with water and a saturated aqueous sodium chloride solution in this order, dried with anhydrous magnesium sulfate, and subjected to distillation under reduced pressure to remove the solvent. The resulting crystal was recrystallized from toluene to obtain 28.5 g (yield: 85.6%) of 4-phenoxy-3-trifluoromethylsulfonylaminophenol having a melting point of 97°-99° C.

IR (KBr) cm⁻¹: 3500, 3150, 1500, 1438, 1360, 1230, 1200,

NMR (CDCl₃+d₆-DMSO)δ: 6.56–7.53 (8H, m), 9.03 (1H, bs), 10.3 (1H, bs)

The following compound was obtained in the same manner:

4-Phenoxy-3-phenylsulfonylaminophenol

Melting point: 182°-183° C. (recrystallized from isopropyl alcohol)

IR (KBr) cm⁻¹: 3425, 3240, 1500, 1480, 1305, 1215, 1160

(4) 10.0 g of 3-amino-4-phenoxyanisole was dissolved in 50 ml of pyridine. Thereto was dropwise added 5.59 g of methanesulfonyl chloride in 10 minutes with ice-cooling. The mixture was stirred for 1 hour at 20°-25° C. The reaction mixture was introduced into a mixture of 200 ml of ethyl acetate and 100 ml of water. The resulting organic layer was separated and washed with three 100-ml portions of 2N hydrochloric acid and then with a saturated aqueous sodium chloride solution. The organic layer was separated, dried with anhydrous magnesium sulfate, and subjected to distillation under reduced pressure to remove the solvent. The resulting crystal was recrystallized from isopropyl alcohol to obtain 12.5 g (yield: 91.9%) of 3-methylsulfonylamino-4-phenoxyanisole having a melting point of 109.5°-111° C.

IR (KBr) cm⁻¹: 3250, 1610, 1585, 1480, 1320, 1220, 1150

NMR (CDCl₃)δ: 2.94 (3H, s), 3.81 (3H, s), 6.36–7.43 (9H, m)

REFERENCE EXAMPLE 4

(1) 21.4 g of 3-amino-4-phenylaminoanisole was dissolved in 210 ml of pyridine. The solution was then ice-cooled. Thereto was dropwise added 12 g of methanesulfonyl chloride in 30 minutes. Stirring was conducted for 2 hours at 5°-10° C. The mixture was subjected to distillation under reduced pressure to remove the solvent. To the residue were added 500 ml of water and 300 ml of ethyl acetate. The resulting mixture was adjusted to pH 4 with 4N hydrochloric acid. The organic layer was separated, washed with water and a saturated aqueous sodium chloride solution in this order, and dried with anhydrous magnesium sulfate. The organic layer was then subjected to distillation under reduced pressure to remove the solvent. Toluene was added to the residue, and the resulting crystal was filtered to obtain 23.9 g (yield: 81.8%) of 3-methylsulfonylamino-4-phenylaminoanisole having a melting point of 109°-111° C.

IR (KBr) cm$^{-1}$: 3360, 3230, 1600, 1490, 1390, 1330, 1290, 1150

(2) 29.2 g of 3-methylsulfonylamino-4-phenylaminoanisole, 18.6 g of ethanethiol and 300 ml of methylene chloride were mixed and then ice-cooled. To the mixture was added 40 g of aluminum chloride in 20 minutes. Stirring was conducted for 3 hours at 5°-10° C. The reaction mixture was introduced into 500 ml of ice water. The resulting organic layer was separated, washed with water and a saturated aqueous sodium chloride solution in this order and then dried with anhydrous magnesium sulfate. The solvent was removed by distillation under reduced pressure. Ethanol was added to the residue and the resulting crystal was filtered to obtain 23.9 g (yield: 86%) of 3-methylsulfonylamino-4-phenylaminophenol having a melting point of 184°-186° C. IR (KBr) cm$^{-1}$: 3425, 3380, 3250, 1600, 1490, 1310, 1150

REFERENCE EXAMPLE 5

(1) 20 g of 4-methoxy-2-nitrophenol was suspended in 350 ml of ethanol. Thereto was added 550 mg of 5% palladium-carbon. The mixture was subjected to hydrogenation at 20°-30° C. at atmospheric pressure. After the completion of the reaction, the catalyst was removed by filtration and then the solvent was removed by distillation under reduced pressure. The resulting crystal was recrystallized from isopropyl alcohol to obtain 15.3 g (yield: 93%) of 2-amino-4-methoxyphenol.

(2) 10 g of 2-amino-4-methoxyphenol was dissolved in 100 ml of methylene chloride. 17 ml of pyridine was added thereto and the mixture was cooled to 5° C. Then, 9.1 g of methanesulfonyl chloride was added dropwise in 10 minutes and stirring gas conducted for 1 hour at 5°-10° C. The solvent was removed by distillation under reduced pressure. To the residue were added 100 ml of ethyl acetate and 50 ml of water. The mixture was adjusted to pH 2 with 4N hydrochloric acid. The organic layer was separated, washed with water and a saturated aqueous sodium chloride solution in this order, and dried with anhydrous magnesium sulfate. The solvent was removed by distillation under reduced pressure. The residue was recrystallized from isopropyl alcohol to obtain 14.4 g (yield: 92%) of 4-methoxy-2-methylsulfonylaminophenol having a melting point of 135°-136° C.

IR (KBr) cm$^{-1}$: 3275, 1600, 1500, 1405, 1325, 1210, 1150

REFERENCE EXAMPLE 6

4-(3-Methylphenoxy)-3-nitroanisole was subjected to the same procedure as in Reference Example 1 (1) and (2) to obtain 3-methylsulfonylamino-4-(3-methylphenoxy)anisole.

Melting point: 87°-88° C. (recrystallized from isopropyl alcohol)

IR (KBr) cm$^{-1}$: 3250, 1480, 1385, 1335, 1250, 1210, 1150, 1105

The compounds shown in Table 8 were obtained in the same manner.

TABLE 8

$$R^5-Z-\underset{\underset{H}{MeSO_2-N}}{\bigcirc}-OMe$$

| $R^5$ | Z | Melting Point (°C.) | IR (KBr) cm$^{-1}$: |
|---|---|---|---|
| 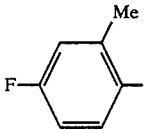 | O | 98–99 [IPE] | 3225, 1615, 1585, 1485, 1400, 1330, 1210, 1165 |
| 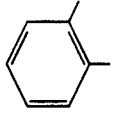 | O | 83–84.5 [IPE] | 3250, 2950, 1490, 1390, 1330, 1230, 1150, 1100 |
| 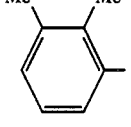 | O | 108–109 [IPA] | 3300, 1610, 1500, 1380, 1330, 1210, 1150 |
| 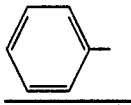 | S | 68–69 [IPA-IPE] | 3290, 1590, 1475, 1320, 1290, 1150 |

REFERENCE EXAMPLE 7

(1) There were mixed 20 g of 4-chloro-3-nitroanisole, 67 ml of acetic acid and 83 ml of 47% (w/w) hydrobromic acid. Thereto was added 50 ml of acetic anhydride. The mixture was refluxed for 8.5 hours. After the completion of the reaction, the solvent was removed by distillation under reduced pressure. The residue was mixed with 300 ml of ethyl acetate and 500 ml of water. The resulting organic layer was separated, washed with a saturated aqueous sodium hydrogencarbonate solution, water and a saturated aqueous sodium chloride solution in this order, and then dried with anhydrous magnesium sulfate. The solvent was removed by distillation under reduced pressure. The resulting crystal was recrystallized from toluene to obtain 15.5 g (yield: 83.6%) of 4-chloro-3-nitrophenol having a melting point of 123.5°-125.5° C.

IR (KBr) cm$^{-1}$: 3400, 1510, 1340, 1280, 1200

(2) 2.0 g of 4-chloro-3-nitrophenol was dissolved in 15 ml of N,N-dimethylformamide. Thereto was added 490 mg of sodium hydride (purity: 60%) in 10 minutes at 5°–10° C. Then, 1.53 g of benzyl chloride was added dropwise in 10 minutes. Stirring was conducted for 1 hour at 70° C. The reaction mixture was introduced into a mixture of 50 ml of ice water and 50 ml of ethyl acetate. The resulting organic layer was separated, washed with water and a saturated aqueous sodium chloride solution in this order, and dried with anhydrous magnesium sulfate. The solvent was removed by distillation under reduced pressure. The residue was washed with n-hexane and then mixed with a mixture of diisopropyl ether and n-hexane. The resulting crystal was collected by filtration to obtain 1.8 g (yield: 59.4%) of 4-benzyloxy-2-nitro-chlorobenzene having a melting point of 50°–50.5° C.

IR (KBr) cm$^{-1}$: 1520, 1475, 1350, 1300, 1235, 990

(3) 880 mg of 4-methoxyphenol was dissolved in 10 ml of N,N-dimethylformamide. 790 mg of potassium t-butoxide was added thereto. Then, 1.7 g of 4-benzyloxy-2-nitro-chlorobenzene was added thereto. The mixture was stirred for 1 hour at 110°–120° C. The reaction mixture was introduced into a mixture of 50 ml of ice water and 50 ml of ethyl acetate. The organic layer was separated, washed with water and a saturated aqueous sodium chloride solution in this order, and dried with anhydrous magnesium sulfate. The solvent was removed by distillation under reduced pressure. The residue was purified by a column chromatography (eluant: toluene) to obtain 1.92 g of 5-benzyloxy-2-(4-methoxyphenoxy)nitrobenzene.

Melting point: 120°–120.5° C. (recrystallized from ethanol)

IR (KBr) cm$^{-1}$: 1520, 1485, 1245, 1225, 1210, 1195

The following compound was obtained in the same manner:

5-Benzyloxy-2-(2-methoxyphenoxy)nitrobenzene

Melting point: 80°–81° C. (recrystallized from ethanol)

IR (KBr) cm$^{-1}$: 1525, 1495, 1350, 1265, 1235, 1215, 1005

(4) 1.8 g of 5-benzyloxy-2-(4-methoxyphenoxy)nitrobenzene was dissolved in 40 ml of acetic acid. 200 mg of 5% palladium-carbon was added thereto. The mixture was subjected to hydrogenation at room temperature at atmospheric pressure. After the completion of the reaction, the catalyst was removed by filtration and the solvent was removed by distillation under reduced pressure. The residue was mixed with 7 ml of methylene chloride and 1.10 ml of pyridine to obtain a solution. Thereto was dropwise added 400 mg of methanesulfonyl chloride in 5 minutes at 5°–10° C. Stirring was conducted for 1 hour at the same temperature. 20 ml of water and 20 ml of chloroform were added thereto. The resulting organic layer was separated and washed with 20 ml of 2N hydrochloric acid and 200 ml of water. The organic layer was mixed with a 5% aqueous sodium hydroxide solution. The aqueous layer was separated and adjusted to pH 2 with 6N hydrochloric acid. 50 ml of ethyl acetate was added thereto. The organic layer was separated, washed with water and a saturated aqueous sodium chloride solution in this order, and dried with anhydrous magnesium sulfate. The solvent was removed by distillation under reduced pressure. The residue was purified by a column chromatography [eluant: a 10 : 1 mixture of toluene and ethyl acetate] to obtain 1.29 g (yield: 81.6%) of 3-methylsulfonylamino-4-(4-methoxyphenoxy)phenol.

Melting point: 109–110.5% (recrystallized from toluene)

IR (KBr) cm$^{-1}$: 3470, 1500, 1315, 1220, 1150

The following compound was obtained in the same manner:

3-Methylsulfonylamino-4-(2-methoxyphenoxy)-phenol

Melting point: 114°–115° C. (recrystallized from toluene)

IR (KBr) cm$^{-1}$: 3480, 3250, 1495, 1305, 1275, 1140

REFERENCE EXAMPLE 8

(1) In 100 ml of anhydrous methylene chloride were dissolved 10 g of 3-methylsulfonylamino-4-phenoxyanisole and 2.81 g of acetyl chloride. Thereto was added 9.1 g of aluminum chloride in 5 minutes with ice-cooling. The mixture was stirred for 1 hour at 20°–25° C. The reaction mixture was introduced into 100 ml of ice water. The resulting organic layer was separated, washed with water and a saturated aqueous sodium chloride solution in this order, and dried with anhydrous magnesium sulfate. The solvent was removed by distillation under reduced pressure. The residue was recrystallized from isopropyl alcohol to obtain 9.83 g (yield: 86%) of methyl 4-methylsulfonylamino-2-methoxy-5-phenoxyphenyl ketone having a melting point of 108.5–110° C.

IR (KBr) cm$^{-1}$: 3300, 1640, 1600, 1490, 1330, 1210, 1155

The compounds shown in Table 9 were obtained in the same manner.

TABLE 9 structure: $R^5$—O— (benzene ring) —C(=O)—$R^4$; Me—SO$_2$—NH— and —O—Me substituents on the ring

| $R^4$ | $R^5$ | Melting point (°C.) | IR (KBr) cm$^{-1}$: |
|---|---|---|---|
| Me | 2-Cl-phenyl | 106–107 | 3270, 1680, 1640, 1610, 1500, 1420, 1340, 1230 |
| Me | 4-Cl-phenyl | Amorphous powder | 3270, 1680, 1640, 1610 |
| Et | phenyl | 104.8–105.6 | 3200, 1660, 1600, 1485, 1410, 1340, 1210, 1160, 1130 |

(2) 10.0 g of methyl 4-methylsulfonylamino-2-methoxy-5-phenoxyphenyl ketone was dissolved in 100 ml of methylene chloride. 3.98 g of aluminum chloride was added thereto in portions in 30 minutes with ice-cooling. The mixture was stirred for 1 hour at 20°-25° C. The reaction mixture was introduced into 100 ml of ice water. The organic layer was separated, washed with water and a saturated aqueous sodium chloride solution in this order, and dried with anhydrous magnesium sulfate. The solvent was removed by distillation under reduced pressure. The resulting crystal was recrystallized from isopropyl alcohol to obtain 8.8 g (yield: 91.9%) of methyl 2-hydroxy-4-methylsulfonylamino-5-phenoxyphenyl ketone having a melting point of 151-153° C.

IR (KBr) cm$^{-1}$: 3230, 1625, 1590, 1580, 1560, 1485

The compounds shown in Table 10 were obtained in the same manner.

TABLE 10

Structure: $R^5-O$ and $Me-SO_2-NH$ substituents on benzene ring with $-C(=O)-R^4$ and $-OH$ groups.

| $R^4$ | $R^5$ | Melting point (°C.) | IR (KBr) cm$^{-1}$ |
|---|---|---|---|
| Me | 2-Cl-phenyl | 153–154 [Ethanol] | 3230, 1630, 1500, 1370, 1320, 1260, 1230 |
| Me | 4-Cl-phenyl | 206–208 [Acetonitrile] | 3240, 1620, 1480, 1420, 1330, 1310, 1220, 1155 |
| Et | phenyl | 151.4–152.4 [IPA] | 3220, 1630, 1580, 1485, 1330, 1215, 1190, 1160, 1115 |

REFERENCE EXAMPLE 9

60 ml of an acetic acid solution containing of boron trifluoride was added to 29- 7 g of 3-methylsulfonylamino-4-phenoxyphenol. The mixture was stirred for 30 minutes at 70°-75° C. The reaction mixture was introduced into 500 ml of water. The resulting crystal was collected by filtration. The crystal was recrystallized from isopropyl alcohol to obtain 2.85 g (yield: 88.8%) of methyl 2-hydroxy-4-methylsulfonylamino 1 5-phenoxyphenyl ketone having a melting point of 151°-153° C.

The compounds shown in Table 11 were obtained in the same manner.

TABLE 11

Structure: $R^5-O$ and $R^1-SO_2-NH$ substituents on benzene ring with $-C(=O)-Me$ and $-OH$ groups.

| $R^1$ | $R^5$ | Melting point (°C.) | IR (KBr) cm$^{-1}$ |
|---|---|---|---|
| Me | 2-F-phenyl | 171–172 [IPA] | 3250, 1635, 1610, 1500, 1420, 1370, 1340, 1265 |
| Me | 3-F-phenyl | 148–149 [IPA] | 3240, 1630, 1600, 1500, 1420, 1350, 1260, 1140 |
| Me | 4-F-phenyl | 174–175 [IPA] | 3240, 1625, 1500, 1425, 1340, 1200 |
| Me | 3,4-diF-phenyl | 179.5–180 [IPA] | 3275, 1640, 1500, 1420, 1375 |

TABLE 11-continued

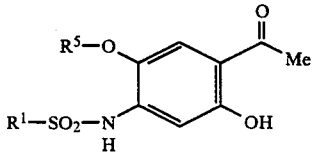

| R¹ | R⁵ | Melting point (°C.) | IR (KBr) cm⁻¹: |
|---|---|---|---|
| Me | Me-[phenyl] (2-methylphenyl) | 132–134 [IPA] | 3225, 1630, 1480, 1420, 1325, 1310, 1220 |
| Me | Me-[phenyl] (4-methylphenyl) | 131–133 [IPA] | 3230, 1625, 1500, 1425, 1340, 1200, 1160 |
| phenyl | phenyl | 147–148 [IPA] | 3240, 1630, 1490, 1340, 1160 |

EXAMPLE 1

(1) 4 g of sodium hydroxide was dissolved in 250 ml of water. Therein was dissolved 27.9 g of 3-methylsulfonylamino-4-phenoxyphenol. Thereto was added an aqueous solution obtained by dissolving 10.9 g of 3-chloropropionic acid and 4 g of sodium hydroxide in 30 ml of water. The mixture was refluxed for 30 minutes. The reaction mixture was water-cooled and adjusted to pH 8 with 4N hydrochloric acid. 70 ml of ethyl acetate was added thereto. The aqueous layer was separated, adjusted to pH 4 with 4N hydrochloric acid and extracted with 100 ml of ethyl acetate. The resulting extracts were washed with water and a saturated aqueous sodium chloride solution in this order, and dried with anhydrous magnesium sulfate. The solvent was removed by distillation under reduced pressure. The residue was mixed with diethyl ether. The resulting solid was collected by filtration to obtain 8.1 g (yield: 23.1%) of 3-(3-methylsulfonylamino-4-phenoxyphenoxy)propionic acid having a melting point of 145°–149° C.

IR (KBr) cm⁻¹: 3250, 1705, 1482, 1325, 1210, 1145

(2) There were mixed 3.51 g of 3-3-methylsulfonylamino-4-phenoxyphenoxy)propionic acid and 70 g of polyphosphoric acid. The mixture was stirred for 1.5 hours at 65°–70° C. The reaction mixture was introduced into 300 ml of ice water. The resulting mixture was extracted with two 200-ml portions of ethyl acetate. The resulting extracts were combined, washed with water and a saturated aqueous sodium chloride solution in this order, and dried with anhydrous magnesium sulfate. The solvent was removed by distillation under reduced pressure. The resulting crystal was recrystallized from methanol to obtain 18.7 g (yield; 56.1%) of 2,3-dihydro-7-methylsulfonylamino-6-phenoxy-4H-1-benzopyran-4-one having a melting point of 143°–144° C.

IR (KBr) cm⁻¹: 3120, 1665, 1610, 1485, 1440, 1320, 1265, 1215, 1160, 1135

MNR (CDCl₃)δ: 2.74 (2H, t, J=6Hz), 3.10 (3H, s), 4.53 (2H, t, J=6Hz), 6.91–7.49 (7H, m), 7.40 (1H, s)

(3) To 60 ml of dioxane were added 3.33 g of 2,3-dihydro-7-methylsulfonylamino-6-phenoxy-4H-1-benzopyran-4-one and 3.40 g of 2,3-dichloro-5,6-dicyano-1,4-benzoquinone. The mixture was refluxed for 12 hours. After water cooling, the precipitate was removed by filtration. The filtrate was subjected to distillation under reduced pressure to remove the solvent. The residue was purified by a column chromatography (eluant: a 5 : 1 mixture of toluene and ethyl acetate) to obtain 2.68 g (yield: 81%) of 7-methylsulfonylamino-6-phenoxy4H-1-benzopyran-4-one [Compound No. 1].

Melting point: 216.7°–217.6° C. (recrystallized from acetonitrile)

IR (KBr) cm⁻¹: 3110, 1620, 1585, 1560, 1485, 1465, 1440, 1320, 1140

NMR (CCDl₃+d₆-DMSO)δ: 3.12 (3H, s), 6.24 (1H, d, J=6Hz), 6.98–7.53 (6H, m), 7.75 (1H, s), 7.90 (1H, d, J=6Hz), 9.20 (1H, bs)

EXAMPLE 2

(1) There were mixed 4.12 g of 3-bromo-2,3-dihydro-7-methylsulfonylamino-6-phenoxy-4H-1-benzopyran-4-one, 9.37 g of silver tetrafluoroborate and 100 ml of methanol. The mixture was refluxed for 4 hours. The reaction mixture was cooled and filtered to remove the insolubles. The filtrate was subjected to distillation under reduced pressure to remove the solvent. The residue was purified by a column chromatography (eluant: a 5 : 1 mixture of toluene and ethyl acetate) to obtain 1.27 g (yield: 35%) of 2,3-dihydro-3-methoxy-7-methylsulfonylamino-6-phenoxy-4H-1-benzopyran-4-one.

Melting point: 139°–141° C. (recrystallized from ethanol)

IR (KBr) cm$^{-1}$: 1 3230, 1680, 1610, 1490, 1450, 1330, 1260, 1210, 1150

(2) There were mixed 3.63 g of 2,3-dihydro-3-methoxy-7-methylsulfonylamino-6-phenoxy-4H-1-benzopyran-4-one, 3.41 g of 2,3-dichloro-5,6-dicyano-1,4-benzoquinone and 150 ml of dioxane. The mixture was refluxed for 48 hours. The reaction mixture was cooled. The resulting precipitate was removed by filtration. The solvent was removed by distillation under reduced pressure. The residue was purified by a column chromatography (eluant: a 3 : 1 mixture of toluene and ethyl acetate) to obtain 1.91 g (yield: 52.9%) of 3-methoxy-7-methylsulfonylamino-6-phenoxy-4H-1-benzopyran-4-one [Compound No. 2].

Melting point: 164°-166° C. (recrystallized from ethanol)

IR (KBr) cm$^{-1}$: 1610, 1480, 1460, 1330, 1260, 1215, 1175, 1140

(3) 3-Methoxy-7-methylsulfonylamino-6-phenoxy-4H-1-benzopyran-4-one was treated in the same manner as in Reference Example 4(2) to obtain 3-hydroxy-7-methylsulfonylamino-6-phenoxy-4H-1-benzopyran-4-one [Compound No. 3].

Melting point: 170°-173° C. (recrystallized from isopropyl alcohol)

IR (KBr) cm$^{-1}$: 1610, 1480, 1470, 1340, 1265, 1210,

EXAMPLE 3

(1) In 50 ml of methylene chloride were dissolved 2.06 g of 3-bromo-2,3-dihydro-7-methylsulfonylamino-6-phenoxy-4H-1-benzopyran-4-one and 480 mg of methylmercaptan. Thereto was added 2.02 g of triethylamine at 0°-5° C. The mixture was stirred for 1 hour at room temperature. The reaction mixture was introduced into 30 ml of water. The organic layer was separated, washed with water, and dried with anhydrous magnesium sulfate. The solvent was removed by distillation under reduced pressure. The residue was purified by a column chromatography (eluant: a 50 : 1 mixture of toluene and ethyl acetate) to obtain 900 mg (yield: 47.4%) of 2,3-dihydro-7-methylsulfonylamino-3-methylthio-6-phenoxy-4H-1-benzopyran-4-one.

Melting point: 126°-128° C. (recrystallized from ethanol)

IR (KBr) cm$^{-1}$: 3250, 1690, 1610, 1480, 1440, 1340, 1260, 1220, 1160, 1140

(2) 350 mg of 2,3-dihydro-7-methylsulfonylamino-3-methylthio-6-phenoxy-4H-1-benzopyran-4-one and 1.08 g of 2,3-dichloro-5,6-dicyano-1,4-benzoquinone were refluxed in 14 ml of dioxane for 9 hours. The solvent was removed by distillation under reduced pressure. The residue was purified by a column chromatography (eluant: a 10 : 1 mixture of toluene and ethyl acetate) to obtain 160 mg (yield: 45.7%) of 7-methylsulfonylamino-3-methylthio-6-phenoxy-4H-1-benzopyran-4-one [Compound No. 4].

Melting point: 175°-176° C. (recrystallized from acetonitrile)

IR (KBr) cm$^{-1}$: 3120, 1600, 1480, 1420, 1310, 1210, 1140

(3) 7-Methylsulfonylamino-3-methylthio-6-phenoxy-4H-1-benzopyran-4-one was reacted with m-chloroperbenzoic acid in equimolar amounts to obtain 3-methylsulfinyl-7-methylsulfonylamino-6-phenoxy-4H-1-benzopyran-4-one [Compound No. 5].

Melting point: >250° C. (recrystallized from acetonitrile)

IR (KBr) cm$^{-1}$: 3100, 1620, 1490, 1460, 1340, 1280, 1220, 1160, 1060

(4) 1 Mole of 7-methylsulfonylamino-3-methylthio-6-phenoxy-4H-1-benzopyran-4-one was reacted with 2 moles of m-chloroperbenzoic acid to obtain 7-methylsulfonylamino-3-methylsulfonyl-6-phenoxy-4H-1-benzopyran-4-one [Compound No. 6].

Melting point: >250° C. (recrystallized from acetonitrile)

IR (KBr) cm$^{-1}$: 3280, 1640, 1620, 1480, 1460, 1340, 1310, 1290, 1220, 1160, 1140

EXAMPLE 4

The compounds shown in Tables 12 to 20 were obtained in the same manner as in Example 1(3), Example 2(2) or Example 3(2).

TABLE 12

R$^5$—Z—[benzopyran-4-one structure]—O—R$^3$, R$^1$—SO$_2$—NH—

| No. | R$^1$ | R$^3$ | R$^5$ | Z | Melting point (°C.) | IR (KBr) cm$^{-1}$: | NMR δ |
|---|---|---|---|---|---|---|---|
| 7 | Et | H |  | O | 216–218 [Ethanol] | 3070, 1620, 1582, 1490, 1455, 1335, 1200, 1155, 1138, | (CDCl$_3$+d$_6$-DMSO) 1.37(3H, t, J=7.2Hz), 3.25(2H, q, J=7.2Hz), 6.22(1H, d, J=6Hz), 7.01–7.47(5H, m), 7.68(1H, s), 7.76 (1H, s), 7.93(1H, d, J=6Hz), 9.21(1H, bs) |

TABLE 12-continued

Structure: R⁵—Z and R¹—SO₂—NH groups on a chromone-type ring with R³ substituent

| No. | R¹ | R³ | R⁵ | Z | Melting point (°C.) | IR (KBr) cm⁻¹ | NMR δ |
|---|---|---|---|---|---|---|---|
| 8 | —CF₃ | H | phenyl | O | 198–200 [Ethanol] | 3075, 1620, 1482, 1382, 1295, 1230, 1200, 1140 | (CDCl₃+d₆-DMSO) 6.24(1H, d, J=6Hz), 7.03–7.84(7H, m), 8.02(1H, d, J=6Hz) |
| 9 | Me | Me | phenyl | O | 186.5–187 [Ethyl acetate-IPE] | 3180, 1630, 1597, 1482, 1452 | (d₆-DMSO) 2.38(3H, s), 3.20 (3H, s), 6.15(1H, s), 6.90–7.50(6H, m), 7.65(1H, s), 9.85 (1H, bs) |
| 10 | Me | H | 2-pyridyl | S | 142–144 [Ethyl acetate-IPE] | 3200, 1630, 1610, 1590, 1440 | (CDCl₃) 3.05(3H, s), 6.26 (1H, d, J=6Hz), 6.90–8.15(4H, m), 7.22(1H, s), 7.77 (1H, d, J=6Hz), 8.48 (1H, s), 8.95(1H, bs) |
| 11 | Me | phenyl | phenyl | O | 222.5–223.1 [Ethyl acetate-IPE] | 3300, 1620, 1483, 1452, 1408 | (d₆-DMSO) 3.28(3H, s), 6.94 (1H, s), 7.05–8.20 (12H, m), 9.90(1H, bs) |
| 12 | Me | H | phenyl | NH | 190–191 [Ethanol] | 3380, 1620, 1610, 1580, 1480, 1450, 1310, 1285, 1155, 1130 | — |
| 13 | Me | H | 3-CF₃-phenyl | O | 182–183.5 [Ethyl acetate-IPE] | 3260, 1660, 1625, 1450, 1325, 1140 | — |
| 14 | Me | H | 3-pyridyl | O | 186–187 [IPA] | 1650, 1620, 1450, 1325, 1220, 1155, 1140 | — |

TABLE 13

Structure: R⁵—O and R¹—SO₂—NH groups on a chromone ring system

| No. | R¹ | R⁵ | Melting point (°C.) | IR (KBr) cm⁻¹ |
|---|---|---|---|---|
| 15 | Me | 2-F-phenyl | 174.5–175.5 [Ethanol] | 3070, 2825, 1620, 1495, 1460, 1335, 1290, 1150 |

TABLE 13-continued

[Structure: R⁵—O— on benzene ring fused to chromone (4H-chromen-4-one); R¹—SO₂—NH— substituent on benzene ring]

| No. | R¹ | R⁵ | Melting point (°C.) | IR (KBr) cm⁻¹: |
|---|---|---|---|---|
| 16 | Me | 3-F-phenyl | 212–213 [Acetonitrile] | 3000, 2800, 1620, 1590, 1460, 1440, 1325, 1300, 1140 |
| 17 | Me | 4-F-phenyl | 211–213 | 3000, 2800, 1620, 1590, 1500, 1460, 1325, 1300, 1200, 1140 |
| 18 | Me | 2-Cl-phenyl | 151–152 [Ethanol] | 3180, 1640, 1620, 1455, 1330, 1295, 1155 |
| 19 | Me | 4-Cl-phenyl | 185–186 [Acetonitrile] | 3070, 1615, 1475, 1450, 1320, 1285, 1205, 1145 |
| 20 | Me | 2-Me-phenyl | 140–141 [Ethanol-IPE] | 3100, 1640, 1620, 1480, 1450, 1335, 1290, 1225, 1160 |
| 21 | Me | 4-Me-phenyl | 151–152 [50% aqueous Ethanol] | 3050, 1620, 1615, 1490, 1450, 1320, 1285, 1205, 1150 |
| 22 | phenyl | phenyl | 208–209 [Ethanol] | 3080, 2875, 1630, 1470, 1435, 1340, 1290, 1160 |

TABLE 14

[Structure: R⁵—O— on benzene ring fused to chromone; 3-NH₂ and 2-R³ substituents on pyranone; R¹—SO₂—NH— on benzene ring]

| No. | R¹ | R³ | R⁵ | Melting point (°C.) | IR (KBr) cm⁻¹: | NMR δ |
|---|---|---|---|---|---|---|
| 23 | Me | H | 2-F-phenyl | 173–174 [Ethyl acetate-IPE] | 3440, 3350, 3150, 1610, 1580, 1560, 1490, 1465, 1330, 1260, 1155 | (CDCl₃) 3.14(3H, s), 3.32(2H, bs), 7.05–7.90(8H, m) |

TABLE 14-continued
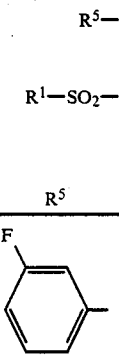
| No. | R¹ | R³ | R⁵ | Melting point (°C.) | IR (KBr) cm⁻¹: | NMR δ |
|---|---|---|---|---|---|---|
| 24 | Me | H | 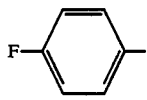 | 207–208 [Ethanol] | 3440, 3340, 3180, 1595, 1580, 1460, 1320, 1260, 1150 | (d₆-DMSO) 3.18(3H, s), 5.5–6.8 (2H, br), 6.90–7.68(4H, m), 7.46(1H, s), 7.64 (1H, s), 7.96(1H, s) |
| 25 | Me | H | 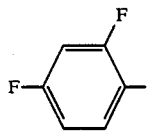 | 204–206 [Ethanol] | 3440, 3340, 3175, 1600, 1585, 1550, 1495, 1465, 1320, 1205, 1150 | (CDCl₃+d₆-DMSO) 3.12(3H, s), 3.12(2H, bs), 7.10–8.20(8H, m) |
| 26 | Me | H | 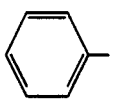 | 202–202.5 [Ethanol] | 3440, 3340, 1620, 1605, 1575, 1555 | (d₆-DMSO) 3.20(3H, s), 7.12–7.69 (4H, m), 7.61(1H, s), 7.96(1H, s) |
| 27 | Me | Me | 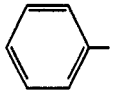 | 176.5–178 [Ethanol] | 3320, 3080, 1615, 1580, 1550, 1480, 1460, 1320, 1260, 1215, 1145, 1120 | (d₆-DMSO) 2.38(3H, s), 3.15(3H, s), 7.04–7.58(7H, m) |
| 28 | ClCH₂— | H | 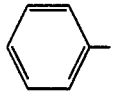 | 207–209 [IPA] | 3450, 3350, 3160, 1600, 1570, 1555, 1480, 1460, 1335, 1200, 1155 | (d₆-DMSO) 5.15(2H, s), 5.5–6.8 (2H, br), 7.06–7.61 (5H, m), 7.31(1H, s), 7.67(1H, s), 7.96(1H, s) |
| 29 | Et | H | 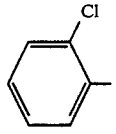 | 208–209 [Ethanol] | 3450, 3350, 3020, 1610, 1580, 1555, 1485, 1465 | — |
| 30 | Me | H | 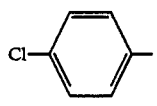 | 199–200 [Acetonitrile] | 3450, 3350, 3100, 1620, 1580, 1470, 1330, 1260, 1150 | — |
| 31 | Me | H | 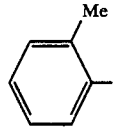 | 215–217 [Acetonitrile] | 3460, 3355, 3260, 1615, 1480, 1470, 1325, 1215, 1160 | — |
| 32 | Me | H | 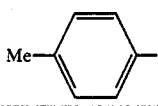 | 193–194 [Ethyl acetate] | 3440, 3350, 3100, 1610, 1580, 1465, 1335, 1260, 1150 | — |
| 33 | Me | H | Me—⟨phenyl⟩— | 177–178 [Ethyl acetate] | 3460, 3350, 3230, 1615, 1465, 1320, 1210, 1155 | — |

TABLE 15

$$R^1-SO_2-NH-\text{[benzene ring with } R^5-O \text{ at 5-position, chromone with C=O, NHR}^7, R^3 \text{]}$$

| No. | R¹ | R³ | R⁵ | R⁷ | Melting point (°C.) | IR (KBr) cm⁻¹ | NMR δ: |
|---|---|---|---|---|---|---|---|
| 34 | Me | H | 2-F-phenyl | CHO | 256–257 [Acetonitrile] | 3380, 3300, 1690, 1620, 1605, 1460, 1335, 1145 | (d₆-DMSO) 3.26(3H, s), 7.10–7.70(5H, m), 7.73(1H, s), 8.36(1H, s), 9.28(1H, s), 9.77(1H, s), 10.16(1H, s) |
| 35 | Me | H | 3-F-phenyl | CHO | 231.5–232.5 [Acetonitrile] | 3350, 3250, 1670, 1600, 1455, 1325, 1250, 1145, 1120 | (d₆-DMSO) 3.23(3H, s), 6.92–7.55(4H, m), 7.48(1H, s), 7.74(1H, s), 8.37(1H, s), 9.29(1H, s), 9.80(1H, s), 10.08(1H, s) |
| 36 | Me | H | 4-F-phenyl | CHO | 237–238 [Acetonitrile] | 3340, 3265, 1685, 1620, 1600, 1495, 1460, 1330, 1195, 1140 | (d₆-DMSO) 3.24(3H, s), 7.10–7.65(5H, m), 7.71(1H, s), 8.35(1H, s), 9.28(1H, s), 9.77(1H, s), 10.04(1H, s) |
| 37 | Me | Me | phenyl | CHO | 205–208 [Ethanol] | 3300, 3150, 1665, 1630, 1620, 1460, 1350, 1320, 1205, 1155 | (d₆-DMSO) 2.34(3H, s), 3.21(3H, s), 7.07–7.69(5H, m), 7.28(1H, s), 7.69(1H, s), 8.20(1H, s), 9.35(1H, s), 9.99(1H, s) |
| 38 | Me | H | phenyl | Ac | 254–256 [Acetonitrile] | 3295, 1665, 1615, 1610, 1490, 1460, 1340, 1210, 1200, 1160 | (d₆-DMSO) 2.12(3H, s), 3.22(3H, s), 7.05–7.61(5H, m), 7.35(1H, s), 7.71(1H, s), 9.18(1H, s), 9.18(1H, s), 9.99(1H, s) |
| 39 | Me | H | 2,4-di-F-phenyl | CHO | 240–241 [Acetonitrile] | 3365, 3300, 1685, 1620, 1605, 1525, 1500, 1460 | (d₆-DMSO) 3.23(3H, s), 7.19–7.67(4H, m), 7.72(1H, s), 8.35(1H, s), 9.28(1H, s), 9.75(1H, s), 10.13(1H, s) |
| 40 | ClCH₂— | H | phenyl | CHO | 239–241 [Acetonitrile] | 3350, 3270, 1685, 1615, 1600, 1480, 1460, 1340, 1200, 1160 | (d₆-DMSO) 5.22(2H, s), 7.12–7.64(5H, m), 7.34(1H, s), 7.78(1H, s), 8.37(1H, s), 9.30(1H, s), 9.77(1H, s), 10.5(1H, bs) |
| 41 | Me | H | phenyl | CO—(CH₂)₂—COOH | 253.5–254 | 3350, 3260, 3125, 1725, 1675, 1610, 1590 | (d₆-DMSO) 3.21(3H, s), 3.21(4H, s), 7.11–7.49(6H, m), 7.71(1H, s), 9.19(1H, s), 9.27(1H, s), 10.0(1H, bs) |
| 42 | Et | H | phenyl | CHO | 226–227 [Acetonitrile] | 3275, 1685, 1610, 1530, 1485, 1460 | (d₆-DMSO) 1.26(3H, t, J=7Hz), 3.32(2H, q, J=7Hz), 7.08–7.62(5H, m), 7.38(1H, s), 7.71(1H, s), 8.35(1H, s), 9.27(1H, s), 9.77(1H, s), 10.04(1H, s) |

TABLE 15-continued
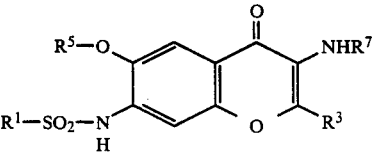
| No. | R¹ | R³ | R⁵ | R⁷ | Melting point (°C.) | IR (KBr) cm⁻¹: | NMR δ: |
|---|---|---|---|---|---|---|---|
| 43 | —CF₃ | H |  | CHO | 211–212 [Ethanol] | 3270, 1680, 1165, 1480, 1455, 1380, 1235, 1200, 1135 | (d₆-DMSO) 6.94–7.55(5H, m), 7.33(1H, s), 7.65(1H, s), 8.34(1H, s), 9.23(1H, s), 10.12(1H, bs) |
| 44 | Me | H | 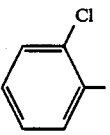 | CHO | 241–242 [Ethanol] | 3350, 3270, 1680, 1620, 1600, 1455, 1330, 1150 | — |
| 45 | Me | H | 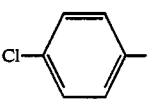 | CHO | 254–255 [Acetonitrile] | 3275, 1660, 1610, 1480, 1450, 1330, 1210 | — |
| 46 | Me | H | 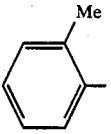 | CHO | 215-14 217 [Acetonitrile] | 3325, 3280, 1685, 1620, 1485, 1455, 1335, 1260, 1155 | — |
| 47 | Me | H | 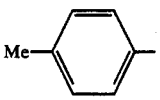 | CHO | 244–245 [Acetonitrile] | 3290, 1670, 1620, 1485, 1450, 1340, 1215, 1160 | — |
TABLE 16
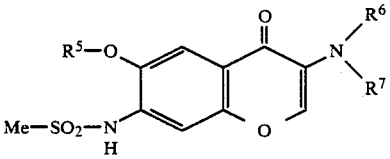
| No. | R⁵ | R⁶ | R⁷ | Melting point (°C.) | IR (KBr) cm⁻¹: | NMR δ: |
|---|---|---|---|---|---|---|
| 48 | 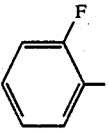 | Me | CHO | 171–172.5 [Ethanol] | 1660, 1640, 1620, 1490, 1460, 1330, 1270, 1160 | (CDCl₃) 3.18(6H, s), 7.10–7.70(5H, m), 7.47(1H, s), 7.82(1H, s), 7.94(1H, s), 8.11(1H, s) |
| 49 | 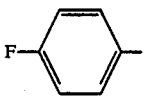 | Me | CHO | 184–186 [Ethanol] | 1655, 1625, 1610, 1490, 1455, 1330, 1270, 1200, 1155 | (CDCl₃) 3.18(6H, s), 7.05–7.70(5H, m), 7.51(1H, s), 7.78(1H, s), 7.94(1H, s), 8.12(1H, s) |
| 50 |  | Et | CHO | 189–190 [Ethanol] | 1650, 1620, 1490, 1460, 1320, 1160 | (CDCl₃) 1.11(3H, t, J=8Hz), 3.16(3H, s), 3.73(2H, q, J=8Hz), 6.80–7.60(6H, m), 7.57(1H, s), 7.80(1H, s), 7.91(1H, s), 8.05(1H, s) |

TABLE 16-continued

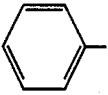

| No. | R⁵ | R⁶ | R⁷ | Melting point (°C.) | IR (KBr) cm⁻¹: | NMR δ: |
|---|---|---|---|---|---|---|
| 51 | Ph | Me | Ac | 183–185 [Ethanol] | 1650, 1610, 1495, 1455, 1330, 1270, 1155 | (CDCl₃) 1.95(3H, s), 3.17(6H, s), 6.80–7.79(6H, m), 7.59(1H, s), 7.80(1H, s), 8.00(1H, s) |
| 52 | Ph | CH₂—COOMe | CHO | 182–183 [Ethyl acetate-IPE] | 3075, 1745, 1660, 1625, 1480, 1450, 1330, 1190, 1145 | (d₆-DMSO) 3.23(3H, s), 3.64(3H, s), 4.34(2H, s), 7.07–7.51(5H, m), 7.31(1H, s), 7.76(1H, s), 8.20(1H, s), 8.58(1H, s), 10.08(1H, s) |
| 53 | Ph | CH₂—CH₂—CH₂—COOEt | CHO | 142.5–144 [Ethanol] | 3240, 1725, 1665, 1640, 1620, 1480, 1450, 1320, 1260, 1150 | (CDCl₃) 1.21(3H, t, J=8Hz), 1.81(2H, t, J=8Hz), 2.33(2H, t, J=8Hz), 3.17(3H, s), 3.69(2H, t, J=8Hz), 4.10(2H, q, J=8Hz), 6.80–7.60(6H, m), 7.57(1H, s), 7.80(1H, s), 8.00(1H, s), 8.07(1H, s) |
| 54 | Ph | Ph-CO— | CHO | 243–244.5 [Acetonitrile] | 3360, 3440, 1658, 1620, 1610, 1520, 1450, 1330, 1210, 1150 | (d₆-DMSO) 3.24(3H, s), 7.07–7.65(8H, m), 7.37(1H, s), 7.76(1H, s), 7.87–8.03(2H, m), 9.11(1H, s), 9.32(1H, s), 10.05(1H, s) |
| 55 | Ph | CO—COOEt | H | 232–233 [Acetonitrile] | 3355, 3230, 1755, 1700, 1630, 1605, 1525, 1460, 1335, 1160 | (d₆-DMSO) 1.30(3H, t, J=7.2Hz), 3.24(3H, s), 4.31(2H, q, J=7.2Hz), 7.09–7.51(5H, m), 7.33(1H, s), 7.75(1H, s), 9.13(1H, s), 9.63(1H, bs), 10.09(1H, s) |
| 56 | Ph | Me | Me | 177–178 [Ethanol] | 3230, 1635, 1615, 1485, 1455, 1340, 1280, 1160 | (d₆-DMSO) 2.67(6H, s), 3.20(3H, s), 7.07–7.50(5H, m), 7.34(1H, s), 7.64(1H, s), 7.89(1H, s), 10.0(1H, s) |
| 57 | Ph | pyrrolidino (R⁶R⁷N—) |  | 191–192 [Ethyl acetate] | 3150, 1620, 1600, 1480, 1420, 1340, 1275, 1210, 1150 | (d₆-DMSO) 1.5–2.2(4H, m), 3.18(3H, s), 3.0–3.6(4H, m), 7.07–7.49(5H, m), 7.32(1H, s), 7.61(1H, s), 7.75(1H, s), 9.87(1H, s) |
| 58 | Ph | H | OH | 113–115 [Ethyl acetate-benzene] | 3280, 3240, 1620, 1560, 1480, 1460, 1320, 1300, 1215, 1135 | (d₆-DMSO+CDCl₃) 2.97(3H, s), 6.99–7.44(5H, m), 7.53(1H, s), 8.06(1H, s), 8.14(1H, s), 9.15(1H, s), 10.80(1H, bs) |

TABLE 17
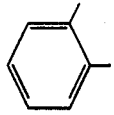
| No. | R³ | R⁴ | R⁵ | Melting point (°C.) | IR (KBr) cm⁻¹: |
|---|---|---|---|---|---|
| 59 | H | —CHO | 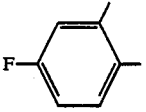 | 234–236 [Ethyl acetate] | 3120, 3080, 1690, 1640, 1620, 1490, 1460, 1335, 1305, 1270, 1150 |
| 60 | H | —CHO | 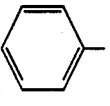 | 247–249 [Acetonitrile] | 3080, 1680, 1630, 1610, 1485, 1450, 1330, 1300, 1250, 1200, 1150, |
| 61 | Me | —CONH₂ | 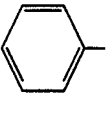 | 248–249 [Acetic acid] | 3310, 3260, 1685, 1620, 1485, 1450, 1380, 1330, 1205, 1155 |
| 62 | H | —CONMe H | 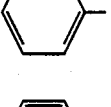 | 255–256 [Ethanol] | 3250, 1680, 1610, 1540, 1480, 1450, 1325, 1150 |
| 63 | H | —CON(cyclopropyl)H | 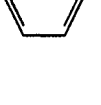 | 224–225 [Ethanol] | 3250, 1670, 1610, 1485, 1455, 1325, 1150 |
| 64 | H | —CON(phenyl)H | 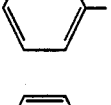 | >250 [Acetonitrile] | 1675, 1610, 1585, 1485, 1455, 1330, 1150 |
| 65 | H | —CONOMe H | 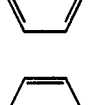 | 247.5–248.5 [Ethanol] | 3280, 3225, 1685, 1615, 1485, 1445, 1330, 1210, 1155 |
| 66 | H | —CON(Me)(Me) | 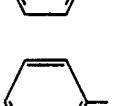 | 213–215 [Ethyl acetate] | 3075, 1620, 1480, 1440, 1330, 1300, 1220, 1150 |
| 67 | H | —CON(piperidinyl) | 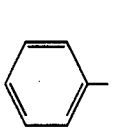 | 204.5–205 [IPA] | 1640, 1625, 1610, 1490, 1440, 1300 |
| 68 | H | —CON(2-pyridyl)H |  | 216–218 [Ethanol] | 3250, 1620, 1460, 1320, 1270 |
| 69 | —CF₃ | H |  | 216–217 [IPA] | 3275, 3050, 1665, 1620, 1490, 1460, 1335, 1220, 1165 |

TABLE 17-continued

[Structure: chromone with R⁵-O- at one position, Me-SO₂-NH- at another, C=O, R⁴, and O-R³]

| No. | R³ | R⁴ | R⁵ | Melting point (°C.) | IR (KBr) cm⁻¹: |
|---|---|---|---|---|---|
| 70 | Et | H | phenyl | 187.5-188.5 [IPA] | 3190, 1625, 1450, 1335, 1150 |
| 71 | -i-Pr | H | phenyl | 163-165 [IPA] | 3260, 1650, 1630, 1485, 1455, 1330, 1215, 1145 |
| 72 | cyclopropyl | H | phenyl | 203-204 [Ethanol] | 3120, 1620, 1455, 1370, 1330, 1205, 1150 |
| 73 | H | H | 4-pyridyl | >250 [IPA] | 1635, 1575, 1485, 1420, 1340, 1295 |
| 74 | H | H | 5-chloro-2-pyridyl | >250 [Dioxane] | 3310, 3070, 1620, 1565, 1460, 1405, 1325, 1295, 1235 |
| 75 | H | H | 2-thienyl | 192.5-193.5 [Ethanol] | 3450, 1620, 1590, 1460, 1440, 1320, 1300 |
| 76 | H | H | 2-(COOMe)phenyl | 189-191 [Ethyl acetate] | 3075, 1710, 1640, 1595, 1450, 1335, 1290, 1160 |
| 77 | H | H | 2-(CONH₂)phenyl | >250 [Acetonitrile] | 3425, 3200, 1660, 1630, 1460, 1320, 1155 |

TABLE 18

[Structure: chromone with R⁵-Z- at one position, Me-SO₂-NH- at another, C=O, R⁴]

| No. | R⁴ | R⁵ | Z | Melting point (°C.) | IR (KBr) cm⁻¹: |
|---|---|---|---|---|---|
| 78 | H | i-Pr phenyl | O | 181.5-183.5 [Ethanol] | 3250, 1640, 1620, 1480, 1450, 1330, 1300, 1220, 1160 |

TABLE 18-continued

Structure: R⁵-Z on benzene ring with Me-SO₂-NH- substituent, connected to chromone-type ring with R⁴ group

| No. | R⁴ | R⁵ | Z | Melting point (°C.) | IR (KBr) cm⁻¹: |
|---|---|---|---|---|---|
| 79 | H | 2,6-dimethylphenyl | O | 157–158 [Ethanol] | 3150, 1640, 1620, 1450, 1335, 1295, 1160 |
| 80 | H | 4-fluoro-2-methylphenyl | O | 160–161 [Ethanol] | 3120, 1615, 1610, 1590, 1485, 1450, 1335, 1295, 1155 |
| 81 | H | phenyl | S | 167.5–169 [2-Methoxyethanol] | 3050, 1625, 1605, 1465, 1440, 1335, 1160, 1135 |
| 82 | —CH₂—phenyl | phenyl | O | 182–183 [Ethanol] | 3125, 1625, 1600, 1485, 1455, 1340, 1160 |
| 83 | Et | phenyl | O | 120–121 [IPA] | 3275, 3120, 1630, 1600, 1480, 1420, 1330, 1210, 1145 |
| 84 | phenyl | phenyl | O | 210–211 [Ethanol] | 3170, 1610, 1590, 1480, 1420, 1155 |
| 85 | -i-Pr | phenyl | O | 155–156 [IPA] | 3250, 1620, 1480, 1450, 1310, 1140 |
| 86 | —NCHO / H | 2-methylphenyl | O | 225–226 [Ethanol] | 3270, 1620, 1605, 1455, 1325, 1150 |
| 87 | —NCHO / H | 4-fluoro-2-methylphenyl | O | 235–236 [Acetonitrile] | 3250, 1680, 1610, 1480, 1450, 1330, 1180, 1155 |
| 88 | —NCHO / H | phenyl | S | >250 [Acetonitrile-DMF] | 3270, 1620, 1600, 1440, 1325, 1150 |
| 89 | —NAc / H | 2-fluorophenyl | O | 233–234 [Acetonitrile] | 3300, 1675, 1605, 1490, 1455, 1330, 1260, 1200, 1155 |

TABLE 18-continued
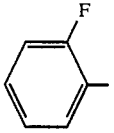
| No. | R⁴ | R⁵ | Z | Melting point (°C.) | IR (KBr) cm$^{-1}$: |
|---|---|---|---|---|---|
| 90 | —C≡NOH | 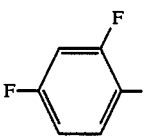 | O | 206–207 [Acetonitrile] | 3240, 1620, 1490, 1455, 1335, 1260, 1160 |
| 91 | —C≡NOH | 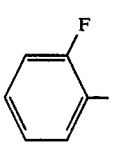 | O | 226–227 [Acetonitrile] | 3260, 3220, 1620, 1615, 1490, 1460, 1340, 1160 |
| 92 | —CN | 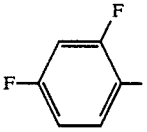 | O | 244–246 [Acetonitrile] | 3140, 3070, 2240, 1655, 1620, 1490, 1460, 1330, 1320, 1270, 1150 |
| 93 | —CN | 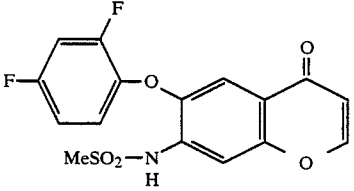 | O | 247–249 [Acetonitrile] | 3120, 3070, 1645, 1620, 1480, 1450, 1330, 1150 |
TABLE 19
| No. | Objective compound | Melting Point (°C.) | IR (KBr) cm$^{-1}$: | NMR δ: |
|---|---|---|---|---|
| 94 | 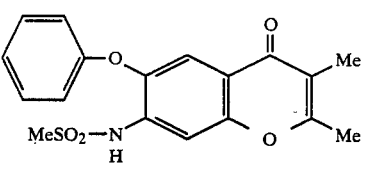 | 182.2–182.8 [Ethyl acetate] | 3200, 3090, 1635, 1500, 1480 | (d₆-DMSO) 3.26(3H, s), 6.28(1H, d, J=6Hz), 7.18(1H, s), 7.71 (1H, s), 7.20–7.66(3H, m), 8.25(1H, d, J=6Hz), 10.09(1H, bs) |
| 95 | 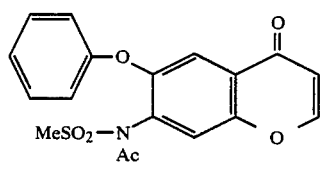 | 224.6–225.6 [Ethyl acetate] | 3200, 1625, 1605, 1460, 1355, 1340, 1260, 1220, 1200, 1155 | (CDCl₃) 2.01(3H, s), 2.39(3H, s), 3.10(3H, s), 6.93–7.42 (6H, m), 7.67(1H, s), 7.59(1H, s) |
| 96 | 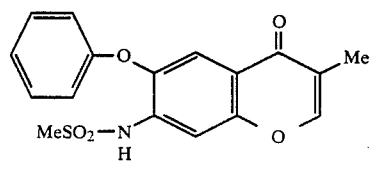 | 166–169 [Ethanol] | 1700, 1640, 1620, 1480, 1445, 1360, 1295, 1155 | (CDCl₃) 2.12(3H, s), 3.40(3H, s), 6.30(1H, d, J=6Hz), 7.11–7.63(7H, m), 7.86(1H, d, J=6Hz), |
| 97 |  | 164–165 [IPA] | 1630, 1605, 1485, 1460, 1340, 1160 | — |

TABLE 19-continued

| No. | Objective compound | Melting Point (°C.) | IR (KBr) cm$^{-1}$: | NMR δ: |
|---|---|---|---|---|
| 98 | (chromone with 3-NH$_2$, 6-phenoxy, 7-MeSO$_2$NH) | 162–163 [Ethanol] | 3440, 3330, 3180, 1600, 1580, 1550, 1480, 1465, 1330, 1205, 1150 | (d$_6$-DMSO) 3.19(3H, s), 5.50–7.00 (2H, br), 7.04–7.49(5H, m), 7.35(1H, s), 7.62(1H, s), 7.94(1H, s) |
| 99 | (chromone with 3-NHCHO, 6-phenoxy, 7-MeSO$_2$NH) | 236–238 [Acetonitrile] | 3340, 3260, 1680, 1615, 1600, 1485, 1460, 1340, 1210, 1150 | (d$_6$-DMSO) 3.24(3H, s), 7.09–7.62 (5H, m), 7.35(1H, s), 7.72(1H, s), 8.36(1H, s), 9.28(1H, s), 9.79(1H, s), 10.04(1H, s) |
| 100 | (chromone with 3-N(Me)CHO, 6-phenoxy, 7-MeSO$_2$NH) | 185–186 [Acetonitrile] | 1655, 1625, 1610, 1490, 1330, 1275, 1160 | (d$_6$-DMSO) 3.04(3H, s), 3.24(3H, s), 7.09–7.62(5H, m), 7.34(1H, s), 7.76(1H, s), 8.09(1H, s), 8.63(1H, s), 10.07 (1H, s) |
| 101 | (chromone with 3-NHMe, 6-phenoxy, 7-MeSO$_2$NH) | 192.5–193 [Ethanol] | 3350, 3100, 1600, 1585, 1560, 1480, 1415, 1330, 1275, 1210, 1200, 1140 | (d$_6$-DMSO) 2.62(3H, s), 3.20(3H, s), 4.50–5.20(1H, br), 7.07–7.50(5H, m), 7.34(1H, s), 7.63(1H, s), 7.67(1H, s), 9.88(1H, s) |
| 102 | (chromone with 3-NHEt, 6-phenoxy, 7-MeSO$_2$NH) | 221–222 [Ethanol] | 3340, 3100, 1580, 1555, 1480, 1420, 1215, 1140 | (CDCl$_3$) 1.29(3H, t, J=8Hz), 3.00 (2H, t, J=8Hz), 3.11(3H, s), 6.70–8.00(7H, m), 7.64(1H, s), 7.70(1H, s) |
| 103 | (chromone with 3-NHCOOMe, 6-phenoxy, 7-MeSO$_2$NH) | 233–235 [Acetonitrile] | 3390, 3330, 1720, 1620, 1605, 1525, 1455, 1335, 1210, 1160 | (d$_6$-DMSO) 3.23(3H, s), 3.66(3H, s), 7.09–7.50(5H, m), 7.34(1H, s), 7.72(1H, s), 8.34(1H, s), 8.74(1H, s), 10.00(1H, s) |
| 104 | (chromone with 3-Br, 6-phenoxy, 7-MeSO$_2$NH) | 215–216 [Acetonitrile] | 3100, 3080, 1635, 1620, 1485, 1455, 1335, 1155 | (d$_6$-DMSO) 3.23(3H, s), 7.06–7.66 (5H, m), 7.30(1H, s), 7.72 (1H, s), 8.81(1H, s), 10.07(1H, s) |
| 105 | (chromone with 3-Cl, 6-phenoxy, 7-MeSO$_2$NH) | 200–201 [Ethyl acetate-IPE] | 3220, 3050, 1645, 1600, 1560, 1480, 1450 | — |
| 106 | (chromone with 3-NHCONH$_2$, 6-phenoxy, 7-MeSO$_2$NH) | >250 [Acetic acid] | 3495, 3340, 3300, 1680, 1620, 1590 | (d$_6$-DMSO) 3.21(3H, s), 6.34(2H, s) 7.02–7.55(6H, m), 7.69(1H, s), 8.02(1H, s), 9.09 (1H, s), 9.90(1H, bs) |

TABLE 19-continued

| No. | Objective compound | Melting Point (°C.) | IR (KBr) cm$^{-1}$: | NMR δ: |
|---|---|---|---|---|
| 107 | (structure) | 145–145.5 [Ethanol] | 3450, 3350, 1640, 1620, 1480, 1450 | (d$_6$-DMSO) 2.95(3H, s), 3.20(3H, s), 5.85(2H, bs), 7.06–7.50 (6H, m), 7.70(1H, s), 8.43(1H, s), 10.00(1H, bs) |
| 108 | (structure) | 220–221 [Ethyl acetate] | 3050, 1780, 1720, 1650, 1620, 1575 | (d$_6$-DMSO) 2.13(3H, s), 2.88(4H, s), 3.59(3H, s), 7.17–7.56 (6H, m), 8.27(1H, s), 8.63(1H, s) |
| 109 | (structure) | 98–100 | 3220, 1730, 1665, 1610, 1490, 1445, 1335, 1205, 1160 | (d$_6$-DMSO) 3.22(3H, s), 4.25(2H, s) 7.07–7.65(5H, m), 7.32(1H, s), 7.76(1H, s), 8.19 (1H, s), 8.56(1H, s), 10.00(1H, bs) |
| 110 | (structure) (hydrobromic acid salt form) | 165 (dec.) | 1620, 1480, 1450, 1350, 1260, 1200, 1150 | — |
| 111 | (structure) | 237–238 [Ethyl acetate-IPE] | 3170, 1670, 1635, 1610, 1475, 1440, 1325, 1260, 1200, 1150 | (d$_6$-DMSO) 3.23(3H, s), 7.04–7.63 (5H, m), 7.23(1H, s), 7.73(1H, s), 8.21(1H, s), 9.63(1H, s), 10.17(1H, s) |
| 112 | (structure) | 188 (dec.) [Aceto-nitrile] | 1675, 1610, 1560, 1450, 1320, 1260, 1205, 1140 | (d$_6$-DMSO) 3.19(3H, s), 4.17(3H, s), 7.04–7.61(5H, m), 7.29 (1H, s), 7.77(1H, s), 8.16(1H, s), 9.07(1H, s), 10.06(1H, s) |
| 113 | (structure) | >250 (dec.) [Ethanol] | 3350, 3280, 1695, 1670, 1620, 1565, 1370, 1340, 1145 | — |
| 114 | (structure) | 229–230 [Aceto-nitrile] | 3260, 2225, 1715, 1610, 1485, 1460, 1330, 1215, 1150 | (d$_6$-DMSO) 3.28(3H, s), 7.07–7.62 (5H, m), 7.27(1H, s), 7.76(1H, s), 8.37(1H, d, J=3Hz), 10.22(1H, d, J=3Hz), 10.22(1H, s) |

TABLE 19-continued

| No. | Objective compound | Melting Point (°C.) | IR (KBr) cm$^{-1}$: | NMR δ: |
|---|---|---|---|---|
| 115 | [structure: phenoxy-benzene with MeSO$_2$-NH substituent, chromone core with pyrrole N-substituted vinyl ketone] | 238.5–240 [Ethyl acetate-IPE] | 1640, 1615, 1575, 1475, 1440, 1425, 1410 | — |
| 116 | [structure: phenoxy-benzene with MeSO$_2$-NH, chromone with NHPh-substituted vinyl ketone] | 212–213 [Aceto-nitrile] | 3240, 1645, 1620, 1580, 1485, 1455, 1340, 1265, 1160 | (d$_6$-DMSO) 3.22(3H, s), 6.92–7.59 (12H, m), 7.76(1H, s), 8.58(1H, s), 10.01(1H, bs) |
| 117 | [structure: phenoxy-benzene with MeSO$_2$-NH, chromone-CHO] | 210–215 (dec.) [Toluene-ethyl acetate] | 3125, 3070, 1685, 1635, 1615, 1485, 1455, 1340, 1305, 1210, 1150 | — |

TABLE 20

| No. | Objective compound | Melting Point (°C.) | IR (KBr) cm$^{-1}$: |
|---|---|---|---|
| 118 | [structure: phenoxy-benzene with MeSO$_2$-NH, chromone with COOEt] | 167–168 [Ethanol] | 3200, 1745, 1620, 1450, 1335, 1310, 1160, 1070 |
| 119 | [structure: phenoxy-benzene with MeSO$_2$-NH, chromone with COOH] | >250 [Acetic acid] | 3200, 1730, 1620, 1460, 1330, 1150 |
| 120 | [structure: phenoxy-benzene with MeSO$_2$-N(Ac), chromone with COOEt and Me] | 166–167.5 [IPA] | 1730, 1705, 1640, 1615, 1435, 1340, 1230, 1160, 1155 |
| 121 | [structure: phenoxy-benzene with MeSO$_2$-NH, chromone with COOH and Me] | 238–241 [Acetic acid] | 3250, 1725, 1620, 1480, 1450, 1375, 1330 |
| 122 | [structure: phenoxy-benzene with MeSO$_2$-NH, chromone with CONH$_2$] | >250 [Acetic acid] | 3350, 1705, 1620, 1585, 1485, 1460, 1340, 1160 |

TABLE 20-continued
| No. | Objective compound | Melting Point (°C.) | IR (KBr) cm$^{-1}$: |
|---|---|---|---|
| 123 | 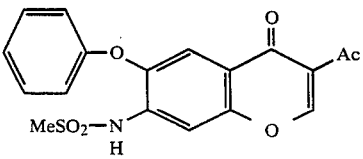 | 175–177 [Ethanol] | 3220, 1680, 1640, 1620, 1485, 1450, 1330, 1295, 1210, 1155 |
| 124 | 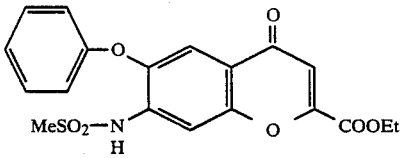 | 155–156 [Ethyl acetate-IPE] | 3235, 1740, 1645, 1620, 1485, 1450, 1360, 1250, 1145 |
| 125 | 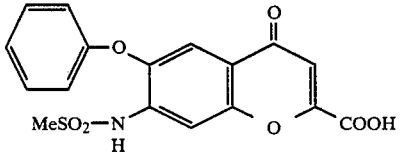 | >250 [Ethanol] | 3245, 1730, 1625, 1590, 1460, 1335, 1220, 1160 |
| 126 | 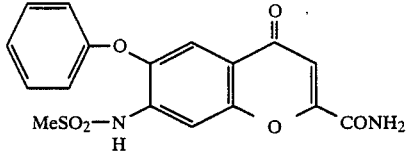 | >250 [Methanol] | 3425, 1700, 1645, 1625, 1450, 1325, 1210, 1135 |
| 127 | 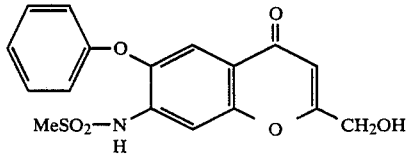 | 210–215 (dec.) [Ethyl acetate] | 3375, 3240, 1630, 1585, 1480, 1455, 1395, 1370, 1325, 1260, 1210 |
| 128 | 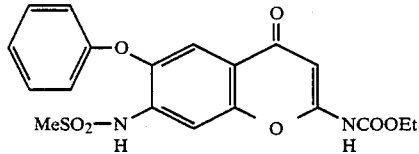 | 207–209 [Ethanol] | 3230, 1740, 1620, 1535, 1480, 1450, 1325, 1210, 1140 |
| 129 | 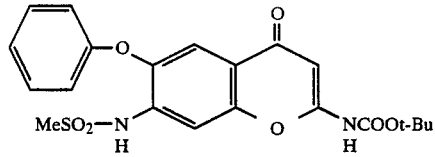 | 147–150 [Benzene] | 3250, 1745, 1620, 1525, 1490, 1450, 1360, 1330, 1230, 1140 |
| 130 | 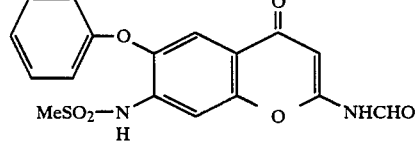 | 214–216 [Acetonitrile] | 3225, 3120, 1710, 1625, 1610, 1555, 1450, 1215, 1150, 1145 |
| 131 | 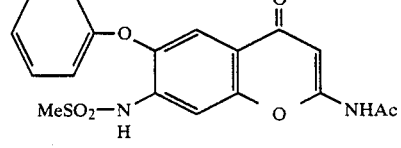 | 236–238 [Ethanol] | 3170, 1700, 1620, 1600, 1525, 1450, 1350, 1250, 1240, 1220, 1145 |

TABLE 20-continued

| No. | Objective compound | Melting Point (°C.) | IR (KBr) cm$^{-1}$: |
|---|---|---|---|
| 132 | (phenoxy-substituted benzene with MeSO$_2$-NH group, C(O)CH=C(NH$_2$)-O-) | 223–225 [Ethanol] | 3225, 1660, 1615, 1550, 1480, 1200, 1145 |
| 133 | (2,4-difluorophenoxy-substituted benzene with MeSO$_2$-NH group, chromone with Me) | 180–181 [IPA] | 3100, 1640, 1605, 1500, 1460, 1390, 1360, 1160, 1140 |
| 134 | (phenoxy-substituted chromone with CH$_2$OH substituent, MeSO$_2$-NH) | 165–166.5 [Ethyl acetate-diethyl ether] | 3450, 3250, 1635, 1605, 1485, 1460, 1325, 1210, 1150 |
| 135 | (phenoxy-substituted chromone with CH=CH-Ph substituent, MeSO$_2$-NH) | 174–175 [Ethanol] | 3400, 1630, 1620, 1480, 1450, 1330, 1200, 1155 |
| 136 | (phenoxy-substituted chromone with CHCH$_3$(OH) substituent, MeSO$_2$-NH) | 136–138 [Ethyl acetate] | 3325, 3225, 1615, 1590, 1480, 1445, 1325, 1205, 1145 |
| 137 | (phenoxy-substituted chromone with CH$_2$NHAc substituent, MeSO$_2$-NH) | 240–242 [IPA] | 3350, 3250, 1680, 1640, 1600, 1460, 1340, 1215, 1150 |
| 138 | (phenoxy-substituted chromone with CH$_2$NH$_2$ substituent, MeSO$_2$-NH) | 190–195 (dec.) [Ethyl acetate] | 3450, 3070, 1635, 1580, 1480, 1455, 1385, 1320, 1275 |
| 139 | (phenoxy-substituted chromone with thiazole substituent, MeSO$_2$-NH) | >250 [Acetonitrile] | 3260, 1635, 1620, 1480, 1450, 1315, 1200, 1150 |

TABLE 20-continued

| No. | Objective compound | Melting Point (°C.) | IR (KBr) cm$^{-1}$: |
|---|---|---|---|
| 140 | (phenoxy-substituted compound with MeSO$_2$-NH and chromone-like dione) | >250 [Acetonitrile] | 3530, 3400, 3300, 1680, 1620, 1560, 1480, 1330, 1225, 1140 |
| 141 | (compound with =N—CHN(Me)Me group) | 103–104 [Diethyl ether] | 1630, 1580, 1470, 1430, 1330, 1190, 1140 |
| 142 | (compound with NCCHMe / OOH group) | 219.5–221.5 [Ethanol] | 3450, 3350, 3250, 1680, 1620, 1590, 1520, 1480, 1460, 1380, 1340, 1260, 1220, 1200, 1160 |
| 143 | (compound with NCCHMe / ONH$_2$ group) | 111–113 (dec.) [Ethanol] | 3250, 1680, 1620, 1500, 1350, 1210, 1160 |
| 144 | (compound with NSO$_2$Me group) | 199–200 [Ethanol] | 3240, 1640, 1630, 1500, 1340, 1330, 1210, 1150 |
| 145 | (compound with OH, OMe, OMe substituents) | 222–223.5 [Acetonitrile] | 3225, 1630, 1490, 1320, 1210, 1160, 1120 |
| 146 | (compound with COOH group) | 243–246 [Acetonitrile] | 3150, 1720, 1670, 1640, 1605, 1480, 1360, 1330, 1260, 1220, 1160 |
| 147 | (compound with NH$_2$ group) | 238–240 [Acetonitrile] | 3415, 3300, 3200, 1635, 1620, 1455, 1330, 1290, 1155 |

TABLE 20-continued

| No. | Objective compound | Melting Point (°C.) | IR (KBr) cm$^{-1}$: |
|---|---|---|---|
| 148 | (structure with NHAc, MeSO$_2$–NH) | 130–132 [Ethanol] | 3250, 1620, 1480, 1450, 1325, 1290, 1150 |
| 149 | (structure with NHCHO, MeSO$_2$–NH) | 203–204 [Acetonitrile] | 3220, 1665, 1620, 1490, 1450, 1320, 1295, 1150 |
| 150 | (structure with OMe, MeSO$_2$–NH) | 122.5–123.5 [Ethanol-IPE] | 3220, 1620, 1490, 1450, 1325, 1290, 1150 |
| 151 | (structure with MeO-, MeSO$_2$–NH) | 122–124 [Ethanol] | 3080, 1620, 1495, 1455, 1335, 1295, 1200, 1160 |
| 152 | (structure with Me, MeSO$_2$–NH) | 183.5–184.5 [Ethanol-DMF] | 3170, 1620, 1455, 1330, 1160, 1140 |
| 153 | (structure with OH, MeSO$_2$–NH) | 186.5–187 [IPA] | 3250, 1620, 1585, 1480, 1450, 1320, 1290, 1160, 1140 |
| 154 | (structure with OMe, NHCHO, MeSO$_2$–NH) | 226.5–227 [Ethyl acetate] | 3280, 1685, 1620, 1600, 1495, 1460, 1335, 1145 |
| 155 | (structure with CH=NOH, MeSO$_2$–NH) | 199–200 [Ethanol] | 3250, 1620, 1495, 1330, 1210, 1160 |

TABLE 20-continued

| No. | Objective compound | Melting Point (°C.) | IR (KBr) cm$^{-1}$: |
|---|---|---|---|
| 156 | (phenoxy substituted chromone with CN group, MeSO₂NH-) | 219.5-220.5 [Ethanol] | 3140, 2240, 1650, 1620, 1485, 1455, 1330, 1155 |
| 157 | (2-fluorophenoxy chromone with CONH₂, MeSO₂NH-) | 249-251 [Acetic acid] | 3330, 3260, 3150, 1695, 1620, 1490, 1455, 1330, 1285, 1155 |
| 158 | (2,4-difluorophenoxy chromone with CONH₂, MeSO₂NH-) | >250 [Acetic acid] | 3380, 3340, 1720, 1670, 1660, 1620, 1500, 1465, 1335, 1300, 1155 |
| 159 | (phenoxy chromone with NO₂ and OH, MeSO₂NH-) | 228-230 (dec.) [Acetonitrile] | 3300, 1755, 1740, 1620, 1600, 1535, 1485, 1440, 1390, 1330, 1205, 1145 |
| 160 | (phenoxy chromone with NO₂, MeSO₂NH-) | 225-227 [Acetonitrile] | 3170, 3070, 1670, 1620, 1480, 1450, 1330, 1300, 1150 |
| 161 | (phenoxy chromone with NHCHO, CH₂=CHSO₂NH-) | 233-234 [Acetonitrile] | 3270, 1685, 1620, 1600, 1460, 1340, 1220, 1150 |
| 162 | (2,4-difluorophenoxy chromone, MeSO₂N(Ac)-) | 176-178 [IPA] | 1705, 1640, 1620, 1440, 1335, 1295, 1245, 1165 |
| 163 | (phenoxy chromone with NHCHO, MeSO₂N(Ac)-) | 237-239 [Acetonitrile] | 3320, 1705, 1685, 1610, 1520, 1485, 1440, 1345, 1240, 1215, 1190, 1160 |

TABLE 20-continued

| No. | Objective compound | Melting Point (°C.) | IR (KBr) cm$^{-1}$: |
|---|---|---|---|
| 164 | (phenoxy-chromone with MeSO$_2$—N(Bz)— substituent) | 164–165.5 [Ethyl acetate] | 1685, 1650, 1610, 1475, 1435, 1360, 1285, 1260, 1200, 1160 |
| 165 | (phenoxy-chromone with MeSO$_2$—N(Me)— substituent) | 187–189 [Ethanol] | 1630, 1610, 1480, 1440, 1340, 1150 |
| 166 | (phenoxy-chromone with MeSO$_2$—NH— and NHCO(CH$_2$)$_3$Cl substituent) | 209–210 [Acetonitrile] | 3300, 3240, 1680, 1620, 1610, 1460, 1340, 1160 |
| 167 | (phenoxy-chromone with MeSO$_2$—NH— and 2-oxopyrrolidin-1-yl substituent) | 192–193 [Ethanol] | 1680, 1635, 1610, 1485, 1335, 1280, 1160 |
| 168 | (phenoxy-chromone with MeSO$_2$—NH— and CONH-tetrazolyl substituent) | >250 [Ethanol] | 3350, 1680, 1620, 1580, 1495, 1465, 1310, 1220, 1170 |
| 169 | (phenoxy-chromone with MeSO$_2$—NH— and CONH-tetrazolyl substituent) | >250 [2-Methoxy-ethanol] | 3120, 1690, 1630, 1590, 1570, 1450, 1370, 1325, 1200, 1140 |
| 170 | (phenoxy-chromone with MeSO$_2$—NH— and tetrazolyl substituent) | >250 [Dioxane-IPE] | 3370, 3170, 1630, 1480, 1460, 1340, 1295, 1160 |
| 171 | (phenoxy-chromone with MeSO$_2$—NH—, CONH$_2$ and NH$_2$ substituents) | >250 [Acetonitrile] | 3460, 3380, 3125, 1640, 1570, 1545, 1475, 1320, 1220, 1150 |

EXAMPLE 5

(1) 3 g of 4-(2,4-difluorophenoxy)-3-methylsulfonylaminophenol was dissolved in 15 ml of N,N-dimethylformamide. 420 mg of sodium hydride (purity: 60%) was added. The mixture was stirred for 20 minutes at 20–25° C. Then, 0.88 g of methyl propiolate was added dropwise in about 5 minutes so that the reaction temperature was maintained below 40° C. The mixture was stirred for 30 minutes at 30°–40° C. After the completion of the reaction, 50 ml of water and 50 ml of ethyl acetate were added thereto. The resulting mixture was adjusted to pH 4 with 4N hydrochloric acid. The organic layer was separated, washed with water and a saturated aqueous sodium chloride solution in this order, and dried with anhydrous magnesium sulfate. The solvent was removed by distillation under reduced pressure, and the residue was purified by a column chromatography (eluant: a 20:1 mixture of toluene and ethyl acetate) to obtain 1.2 g (yield: 31.6%) of methyl trans-3-[4-(2,4-difluorophenoxy)-3-methylsulfonylaminophenoxy]acrylate.

Melting point: 98.5°-98.9° C. (recrystallized from ethyl acetate-diisopropyl ether)

IR (KBr) cm$^{-1}$: 3180, 1700, 1645, 1600, 1485, 1335

NMR (CDCl$_3$) δ: 3.07(3H, s), 3.73(3H, s), 5.55(1H, d, J=12Hz), 6.70-7.40(7H, m), 7.70(1H, d, J=12Hz)

The compounds shown in Table 21 were obtained in the same manner.

(2) 24 ml of a 1N aqueous sodium hydroxide solution was added to 1.2 g of methyl trans-3-[4-(2,4-difluorophenoxy)-3-methylsulfonylaminophenoxy]acrylate. The mixture was stirred for 1 hour at 20°-25° C. 30 ml of ethyl acetate was added thereto. The resulting mixture was adjusted to pH 4 with 4N hydrochloric acid. The organic layer was separated, washed with water and a saturated aqueous sodium chloride solution in this order, and dried with anhydrous magnesium sulfate. The solvent was removed by distillation under reduced pressure to obtain 1.0 g (yield: 87.0%) of oily trans-3-[4-(2,4-difluorophenoxy)-3methylsulfonylaminophenoxy]acrylic acid.

IR (neat) cm$^{-1}$: 3250, 1690, 1600, 1485

NMR (CDCl$_3$) δ: 3.07(3H), s), 5.52(1H, d, J=12Hz), 6.70-7.04(7H, m), 7.79(1H, d, J=12Hz)

The compounds shown in Table 22 were obtained in the same manner.

TABLE 21

| Objective compound | Melting Point (°C.) | IR (KBr) cm$^{-1}$: | NMR (CDCl$_3$) δ: |
|---|---|---|---|
| [structure: MeSO$_2$-NH-phenyl-O-phenyl with COOMe acrylate] | 101-103 [Ethyl acetate-IPE] | 3250, 1700, 1645, 1607, 1490, 1340, 1220, 1163, 1145, 1120 | 3.01(3H, s), 3.73(3H, s), 5.50(1H, d, J=12Hz), 6.60-7.40(9H, m), 7.70 (1H, d, J=12Hz) |
| [structure: CF$_3$-SO$_2$-NH-phenyl-O-phenyl with MeOOC cis-acrylate] | 140-143 [Ethyl acetate-IPE] | 3060, 1695, 1640, 1485, 1378, 1230, 1205, 1190, 1160, 1140 | 3.37(3H, s), 5.20(1H, d, J=6Hz), 6.72-7.42(10H, m) |
| [structure: MeSO$_2$-NH-phenyl-O-phenyl-O-C(Me)=CH-COOEt] | 90.5-91.1 [IPE] | 3250, 1700, 1620, 1495, 1405 | 1.23(3H, t, J=7Hz), 2.46(3H, s), 3.00(3H, s), 4.11(2H, q, J=7Hz), 4.95(1H, s), 6.55-7.55(9H, m) |
| [structure: pyridyl-S-phenyl(MeSO$_2$NH)-O-CH=CH-COOMe] | 102-103 | 3250, 1700, 1645, 1585, 1565, 1480, 1330, 1175, 1140, 1120 | 2.98(3H, s), 3.75(3H, s), 5.65(1H, d, J=12Hz), 7.80(1H, d, J=12Hz), 6.20-8.50(7H, m), 8.58(1H, bs) |

TABLE 22

| Objective compound | Melting Point (°C.) | IR (KBr) cm$^{-1}$: | NMR δ: |
|---|---|---|---|
| [structure: MeSO$_2$-NH-phenyl-O-phenyl-O-CH=CH-COOH] | 110-111 (dec.) | 3250, 1670, 1635, 1600, 1490, 1343, 1190, 1155 | (d$_6$-DMSO) 2.99(3H, s), 5.40(1H, d, J=12Hz), 6.84-7.56(8H, m), 7.70(1H, d, J=12Hz), 8.40(1H, bs) |

TABLE 22-continued

| Objective compound | Melting Point (°C.) | IR (KBr) cm$^{-1}$: | NMR δ: |
|---|---|---|---|
| (structure: CF$_3$—SO$_2$—NH—phenyl with O-phenyl and O—CH=CH—COOH) | 190–193 [Ethyl acetate] | 3150, 1680, 1625, 1490, 1230, 1210, 1185 | (CDCl$_3$ + d$_6$-DMSO) 5.15(1H, d, J=6Hz), 6.75–75.8(9H, m) |
| (structure: MeSO$_2$—NH—phenyl with O-phenyl and O—C(Me)=CH—COOH) | 153.6–154.1 [Ethyl acetate-IPE] | 1680, 1600, 1490, 1330 | (CDCl$_3$) 2.47(3H, s), 3.02(3H, s), 4.94(1H, s), 6.55–7.55(9H, m) |
| (structure: pyridyl—S—phenyl with MeSO$_2$—NH and O—CH=CH—COOH) | 174–176 | 1680, 1650, 1580, 1480, 1320, 1180, 1125 | (CDCl$_3$) 3.00(3H, s), 5.60(1H, d, J=12Hz), 7.75(1H, d, J=12Hz), 6.70–8.50(7H, m) |

(3) 30 g of polyphosphoric acid was added to 1.0 g of trans-3-[4-(2,4-difluorophenoxy)-3-methylsulfonylaminophenoxylacrylic acid. The mixture was stirred for 1 hour at 55°–65° C. The reaction mixture was introduced into 200 ml of ice water. 50 ml of ethyl acetate was added thereto. The organic layer was separated, washed with water and a saturated aqueous sodium chloride solution in this order, and dried with anhydrous magnesium sulfate. The solvent was removed by distillation under reduced pressure. The residue was purified by a column chromatography (eluant: a 5 : 1 mixture of toluene and ethyl acetate) to obtain 0.4 g (yield: 42.0%) of 6-(2,4-difluorophenoxy)-7-methylsulfonylamino-4H-1-benzopyran-4-one. Melting point: 182.2°–182.8° C. (recrystallized from ethyl acetate)

IR (KBr) cm$^{-1}$: 3200, 3090, 1635, 1500, 1480

NMR (d$_6$-DMSO) δ: 3.26(3H, s), 6.28(1H, d, J=6Hz), 7.18(1H, s), 7.71(1H, s), 7 20–7 66(3H, m), 8.25(1H, d, J=6Hz), 10.09(1H, bs)

EXAMPLE 6

The compounds shown in Table 23 were obtained in the same manner as in Example 5(3).

The physical properties of these compounds were identical with those of the compounds in Examples 1 to 4.

TABLE 23

(general structure with R$^5$—Z, R$^1$—SO$_2$—N(R$^2$)—, R$^{3a}$, R$^{4a}$ substituents on benzopyranone)

| R$^1$ | R$^2$ | R$^{3a}$ | R$^{4a}$ | R$^5$ | Z |
|---|---|---|---|---|---|
| Me | H | H | H | phenyl | O |
| Et | H | H | H | phenyl | O |
| —CF$_3$ | H | H | H | phenyl | O |

TABLE 23-continued

Structure:

$R^5-Z$ and $R^1-SO_2-N(R^2)-$ substituents on a chromone-type core with $R^{3a}$ and $R^{4a}$ substituents.

| $R^1$ | $R^2$ | $R^{3a}$ | $R^{4a}$ | $R^5$ | Z |
|---|---|---|---|---|---|
| Me | H | Me | H | phenyl | O |
| Me | H | H | H | 2-pyridyl | O |
| Me | phenyl | | H | phenyl | O |
| Me | H | H | H | phenyl | HN |
| Me | H | H | H | 3-(CF$_3$)phenyl | O |
| Me | H | H | H | 3-pyridyl | O |
| Me | H | H | H | 2-F-phenyl | O |
| Me | H | H | H | 3-F-phenyl | O |
| Me | H | H | H | 4-F-phenyl | O |
| Me | H | H | H | 2-Cl-phenyl | O |
| Me | H | H | H | 4-Cl-phenyl | O |

TABLE 23-continued

Structure:
R⁵−Z on benzene ring; R¹−SO₂−N(R²) attached to benzene; benzene fused to chromone with R⁴ᵃ and R³ᵃ

| R¹ | R² | R³ᵃ | R⁴ᵃ | R⁵ | Z |
|---|---|---|---|---|---|
| Me | H | H | H | 2-methylphenyl | O |
| Me | H | H | H | 4-methylphenyl | O |
| phenyl | H | H | H | phenyl | O |
| Me | H | H | —CHO | 2-fluorophenyl | O |
| Me | H | H | —CHO | 2,4-difluorophenyl | O |
| Me | H | Me | —CONH₂ | phenyl | O |
| Me | H | H | —CONMe₂ | phenyl | O |
| Me | H | H | —CONH-cyclopropyl | phenyl | O |
| Me | H | H | —CONH-phenyl | phenyl | O |
| Me | H | H | —CONHOMe | phenyl | O |
| Me | H | H | —CON(Me)₂ | phenyl | O |

TABLE 23-continued
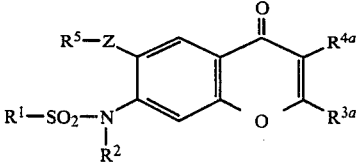
| R¹ | R² | R³ᵃ | R⁴ᵃ | R⁵ | Z |
|---|---|---|---|---|---|
| Me | H | H | —CON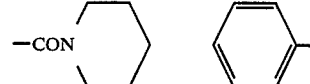 | 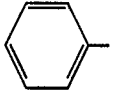 | O |
| Me | H | H | —CONH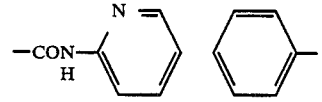 | 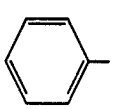 | O |
| Me | H | —CF₃ | H | 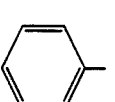 | O |
| Me | H | Et | H | 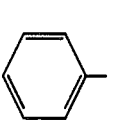 | O |
| Me | H | -i-Pr | H |  | O |
| Me | H |  | H |  | O |
| Me | H | H | H | 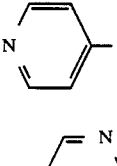 | O |
| Me | H | H | H |  | O |
| Me | H | H | H | 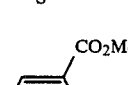 | O |
| Me | H | H | H | 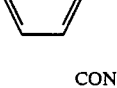 | O |
| Me | H | H | H | 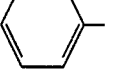 | O |

TABLE 23-continued
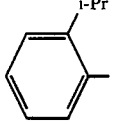
| $R^1$ | $R^2$ | $R^{3a}$ | $R^{4a}$ | $R^5$ | Z |
|---|---|---|---|---|---|
| Me | H | H | H | i-Pr 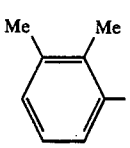 | O |
| Me | H | H | H | Me, Me 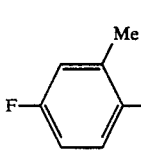 | O |
| Me | H | H | H | Me, F 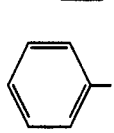 | O |
| Me | H | H | H | 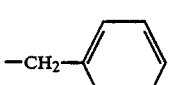 | S |
| Me | H | H | —CH$_2$— 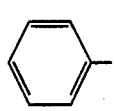 | 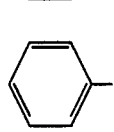 | O |
| Me | H | H | Et | 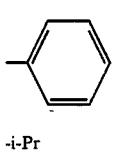 | O |
| Me | H | H | 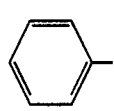 | 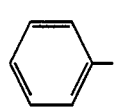 | O |
| Me | H | H | -i-Pr | 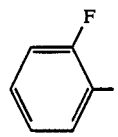 | O |
| Me | H | H | —CN | F 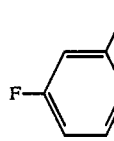 | O |
| Me | H | H | —CN | F, F 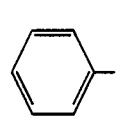 | O |
| Me | H | Me | Me |  | O |

TABLE 23-continued

Structure: R⁵—Z—[benzene ring]—C(=O)—C(R⁴ᵃ)=C(R³ᵃ)—O— (fused), with R¹—SO₂—N(R²)— substituent

| R¹ | R² | R³ᵃ | R⁴ᵃ | R⁵ | Z |
|---|---|---|---|---|---|
| Me | Ac | H | H | Ph | O |
| Me | H | H | Me | Ph | O |
| Me | H | H | —CHO | Ph | O |
| Me | H | H | —COOEt | Ph | O |
| Me | H | H | —COOH | Ph | O |
| Me | Ac | Me | —COOEt | Ph | O |
| Me | H | Me | —COOH | Ph | O |
| Me | H | H | —CONH₂ | Ph | O |
| Me | H | H | Ac | Ph | O |
| Me | H | Me | H | 2,4-difluorophenyl | O |
| Me | H | H | —CH₂OH | Ph | O |

TABLE 23-continued $$R^5-Z \quad \underset{R^1-SO_2-N}{\overset{O}{\underset{R^2}{\parallel}}} \quad \overset{R^{4a}}{\underset{O}{\rightthreetimes}} R^{3a}$$

| $R^1$ | $R^2$ | $R^{3a}$ | $R^{4a}$ | $R^5$ | Z |
|---|---|---|---|---|---|
| Me | H | H | —CHCH₃<br>\|<br>OH | phenyl | O |
| Me | H | H | H | 2-COOH-phenyl | O |
| Me | H | H | H | 2-NH₂-phenyl | O |
| Me | H | H | H | 2-NHAc-phenyl | O |
| Me | H | H | H | 2-NHCHO-phenyl | O |
| Me | H | H | H | 2-OMe-phenyl | O |
| Me | H | H | H | 4-MeO-phenyl | O |
| Me | H | H | H | 3-Me-phenyl | O |
| Me | H | H | H | 2-OH-phenyl | O |
| Me | H | H | —CN | phenyl | O |

TABLE 23-continued

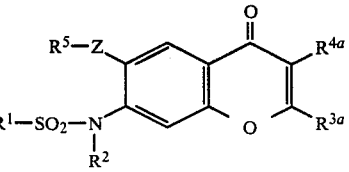

| R¹ | R² | R³ᵃ | R⁴ᵃ | R⁵ | Z |
|---|---|---|---|---|---|
| Me | H | H | —CONH₂ | 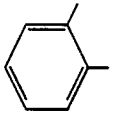 | O |
| Me | H | H | —CONH₂ | 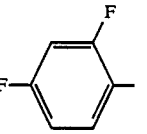 | O |
| CH₂=CH— | H | H | H | 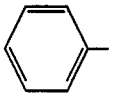 | O |
| Me | Ac | H | H | 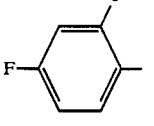 | O |
| Me | Bz | H | H | 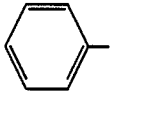 | O |
| Me | Me | H | H | 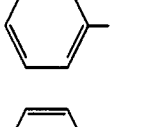 | O |
| Me | H | H | 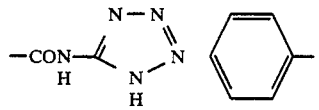 | 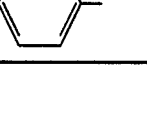 | O |

EXAMPLE 7

In 70 ml of toluene was suspended 3.4 g of methyl 2-hydroxy-4-methylsulfonylamino-5-phenoxyphenyl ketone. 17 ml of ethyl formate was added thereto. Further, 3.4 g of sodium hydride (purity: 60%) was added thereto in portions in 20 minutes. The mixture was refluxed for 5 hours. The reaction mixture was introduced into 300 ml of ice water. The aqueous layer was separated and adjusted to pH 4 with 4N hydrochloric acid. The mixture was then extracted with two 100-ml portions of ethyl acetate. The extracts were combined and subjected to distillation under reduced pressure to remove the solvent. The residue was dissolved in 20 ml of acetic acid. 1 ml of concentrated hydrochloric acid was added. The mixture was heated for 30 minutes at 50°–60° C. 200 ml of water was added thereto. The resulting mixture was extracted with 200 ml of ethyl acetate. The extract was washed with water and a saturated aqueous sodium chloride solution in this order, and dried with anhydrous magnesium sulfate. The solvent was removed by distillation under reduced pressure. The residue was recrystallized from acetonitrile to obtain 2.28 g (yield: 65%) of 7-methylsulfonylamino-6-phenoxy-4H-1-benzopyran-4-one having a melting point of 216.7°–217 6° C.

IR (KBr) cm⁻¹: 3110, 1620, 1585, 1560, 1485, 1465, 1440, 1320, 1140

EXAMPLE 8

There were mixed 3.21 g of methyl 2-hydroxy-4-methylsulfonylamino-5-phenoxyphenyl ketone, 5.45 g of acetic anhydride and 4.1 g of sodium acetate. The mixture was stirred for 1.5 hours at 130°–140° C. The reaction mixture was cooled to room temperature. 200 ml of ethyl acetate and 100 ml of water were added thereto. The organic layer was separated, washed with water and a saturated aqueous sodium chloride solution in this order, and dried with anhydrous magnesium sulfate. The solvent was removed by distillation under reduced pressure. The residue was recrystallized from ethyl acetate-diisopropyl ether to obtain 860 mg (yield: 25%) of 2-methyl-7-methylsulfonylamino-6-phenoxy-4H-1-benzopyran-4-one having a melting point of 186.5°–187° C.

EXAMPLE 9

In 16 ml of ethyl orthoformate was suspended 3.21 g of methyl 2-hydroxy-4-methylsulfonylamino-5-phenoxyphenyl ketone. To the mixture being ice-cooled was dropwise added 2.15 g of a 70% aqueous perchloric acid solution in 10 minutes. Stirring was conducted for 30 minutes at 20°–25° C. 50 ml of diethyl ether was added thereto. The resulting crystal was collected by filtration. The crystal was mixed with 50 ml of water, and the mixture was refluxed for 2 minutes and then cooled to room temperature. The resulting crystal was collected by filtration and recrystallized from acetonitrile to obtain 2.90 g (yield: 87.6%) of 7-methylsulfonylamino-6-phenoxy-4H-1-benzopyran-4-one.

The properties (melting point, IR and NMR) of this compound agreed with those of the compound obtained in Example 1 (3).

EXAMPLE 10

(1) In 500 ml of toluene were suspended 26.0 g of methyl 2-hydroxy-4-methylsulfonylamino-5-phenoxyphenyl ketone and 52 ml of ethyl formate. Thereto was added 16.3 g of sodium hydride (purity: 60%) in portions in 30 minutes at 50°–60° C. The mixture was refluxed for 2 hours. The reaction mixture was introduced into 500 ml of ice water. The mixture was adjusted to pH 2 with 6N hydrochloric acid. The organic layer was separated, washed with water and a saturated aqueous sodium chloride solution in this order, and dried with anhydrous magnesium sulfate. The solvent was removed by distillation under reduced pressure. The resulting oily matter was purified by a column chromatography (eluant: a 3 : 1 mixture of toluene and ethyl acetate) to obtain 25 g (yield: 88.7%) of 3-(2-hydroxy-4-methylsulfonylamino-5-phenoxybenzoyl)acetaldehyde.

Melting point: 121°–123° C. (recrystallized from ethyl acetate)

(2) 25 g of 2-(2-hydroxy-4-methylsulfonylamino-5-phenoxybenzoyl)acetaldehyde was dissolved in 260 ml of benzene and 130 ml of N,N-dimethylformamide. Thereto was added 26 ml of N,N-dimethylformamide dimethylacetal. The mixture was stirred for 8 hours at room temperature. The reaction mixture was introduced into a mixture consisting of 200 ml of ethyl acetate and 200 ml of water. The organic layer was separated, washed with water and a saturated aqueous sodium chloride solution in this order, and dried with anhydrous magnesium sulfate. The solvent was removed by distillation under reduced pressure. The resulting oily matter was purified by a column chromatography (eluant: a 20 : 1 mixture of toluene and ethyl acetate) to obtain 13 g (yield: 50.4%) of 3-formyl-7-methylsulfonylamino-6-phenoxy-4H-1-benzopyran-4-one.

Melting point: 210°–215° C. (decomposed) (recrystallized from toluene-ethyl acetate)

IR (KBr) cm$^{-1}$: 3125, 3070, 1685, 1635, 1615, 1485, 1455, 1340, 1305, 1210, 1150

EXAMPLE 11

(1) 50 g of methyl 2-hydroxy-4-methylsulfonylamino5-phenoxyphenyl ketone was dissolved in 1 liter of N,N-dimethylformamide. Thereto was added 13.7 g of sodium hydride (purity: 60%) in portions in 30 minutes at 20°–40° C. The mixture was stirred for 1 hour at 30°–40° C. Thereto was added 29.3 g of benzyl bromide in portions in 1 hour at 10°–15° C. Then, stirring was effected for 1 hour at 20°–25° C. The reaction mixture was mixed with 500 ml of ethyl acetate and 500 ml of water. The aqueous layer was separated. It was mixed with 500 ml of ethyl acetate. The mixture was adjusted to pH 2 with concentrated hydrochloric acid. The organic layer was separated, washed with water and a saturated aqueous sodium chloride solution in this order, and dried with anhydrous magnesium sulfate. The solvent was removed by distillation under reduced pressure. The residue was recrystallized from toluene to obtain 32.4 g (yield: 50.7%) of methyl 2-benzyloxy-4-methylsuflonylamino-5-phenoxyphenyl ketone having a melting point of 132°–134° C.

IR (KBr) cm$^{-1}$: 3225, 1660, 1500, 1420, 1335, 1215, 1160

(2) There were mixed 4.11 g of methyl 2-benzyloxy-4-methylsulfonylamino-5-phenoxyphenyl ketone, 20.6 ml of diethyl carbonate, 20.6 ml of N,N-dimethylformide and 1.6 g of sodium hydride (purity: 60%). The mixture was stirred for 30 minutes at 90°–100° C. The reaction mixture was introduced into 200 ml of ice water. The resulting mixture was washed with 50 ml of diethyl ether. The aqueous layer was separated, adjusted to pH 5 with 4N hydrochloric acid, and extracted with two 100-ml portions of ethyl acetate. The extracts were combined, washed with water and a saturated aqueous sodium chloride solution in this order, and dried with anhydrous magnesium sulfate. The solvent was removed by distillation under reduced pressure. The residue was purified by a column chromatography (eluant: a 3 : 1 mixture of toluene and ethyl acetate) to obtain 4.35 g (yield: 90%) of ethyl 2-(2-benzyloxy-4-methylsulfonylamino-5-phenoxybenzoyl)acetate.

Melting point: 85°–90° C. (recrystallized from diisopropyl ether)

IR (KBr) cm$^{-1}$: 3325, 1740, 1655, 1605, 1495, 1425, 1395, 1340, 1200, 1160, 1120

(3) In 50 ml of ethanol was dissolved 4.83 g of ethyl 2-(2-benzyloxy-4-methylsulfonylamino-5-phenoxybenzoyl)acetate. Thereto was added 200 mg of 5% palladium-carbon. The mixture was subjected to hydrogenation for 1 hour at 40° C. at atmospheric pressure. After the completion of the reaction, the catalyst was removed by filtration. The filtrate was subjected to distillation under reduced pressure to remove the solvent. The residue was mixed with diisopropyl ether. The resulting crystal was collected by filtration and recrystallized from a mixed solvent of ethyl acetate and diisopropyl ether to obtain 3.46 g (yield: 88%) of ethyl 2-(2-hydroxy-4-methylsulfonylamino-5-phenoxybenzoyl)acetate having a melting point of 111.5°–112.5° C.

IR (KBr) cm$^{-1}$: 3330, 1740, 1640, 1490, 1345, 1210, 1160, 1120

(4) 3.93 g of ethyl 2-(2-hydroxy-4-methylsulfonylamino-5-phenoxybenzoyl)acetate was dissolved in 40 ml of N,N-dimethylformamide. Thereto was added 2.60 g of N,N-dimethylformaide dimethylacetal. The mixture was stirred for 1 hour at 20°–25° C. The reaction mixture was introduced into 200 ml of water. The resulting mixture was adjusted to pH 5 with 4N hydrochloric acid and then extracted with 100 ml of ethyl acetate. The extract was washed with water and a saturated aqueous sodium chloride solution in this order, and dried with anhydrous magnesium sulfate. The solvent was removed by distillation under reduced pressure. The residue was recrystallized from ethanol to obtain 3.55 g (yield: 88.1%) of 3-ethoxycarbonyl-7-methylsulfonylamino-6-phenoxy-4H-1-benzopyran-4-one having a melting point of 167°–168° C.

IR (KBr) cm$^{-1}$: 3200, 1745, 1620, 1450, 1335, 1310, 1160, 1070

(5) 80 ml of dioxane and 40 ml of 6N hydrochloric acid were added to 4.03 g of 3-ethoxycarbonyl-7-methylsulfonylamino-6-phenoxy-4H-1-benzopyran-4-one. The mixture was refluxed for 30 minutes. The reaction mixture was cooled. 200 ml of water was added thereto. The resulting crystal was collected by filtration, washed with water and recrystallized from acetic acid to obtain 3.41 g (yield: 91%) of 3-carboxy-7-methylsulfonylamino-6-phenoxy4H-1-benzopyran-4-one having a melting point of >250° C.

IR (KBr) cm$^{-1}$: 3200, 1730, 1620, 1460, 1330, 1150

EXAMPLE 12

(1) 2.55 ml of acetic anhydride was added to 850 mg of ethyl 2-(2-hydroxy-4-methylsulfonylamino-5-phenoxybenzoyl)acetate and 540 mg of sodium acetate. The mixture was stirred for 10 minutes at 110°–120° C. The reaction mixture was introduced into a mixture of 20 ml of ethyl acetate and 20 ml of water. The resulting mixture was adjusted to pH 2 with 2N hydrochloric acid. The organic layer was separated, washed with water and a saturated aqueous sodium chloride solution in this order, and dried with anhydrous magnesium sulfate. The solvent was removed by distillation under reduced pressure. The residue was purified by a column chromatography (eluant: a 5 : 1 mixture of toluene and ethyl acetate) to obtain 550 mg (yield: 55.6%) of 7-(N-acetyl-N-methylsulfonylamino)-3-ethoxycarbonyl-2-methyl-6-phenoxy-4H-1-benzopyran-4-one.

Melting point: 166°–167.5° C. (recrystallized from isopropyl alcohol)

IR (KBr) cm$^{-1}$: 1730, 1705, 1640, 1615, 1435, 1340, 1230, 1160, 1155

(2) 10 ml of dioxane and 10 ml of 6N hydrochloric acid were added to 500 mg of 7-(N-acetyl-N-methylsulfonylamino)-3-ethoxycarbonyl-2-methyl-6-phenoxy-4H-1-benzopyran-4-one. The mixture was refluxed for 20 minutes. The reaction mixture was cooled to 5°–10° C. 30 ml of water was added thereto. The resulting crystal was collected by filtration and recrystallized from acetic acid to obtain 400 mg (yield: 95.2%) of 3-carboxy-2-methyl-7-methylsulfonylamino-6-phenoxy-4H-1-benzopyran-4-one having a melting point of 238°–241° C.

IR (KBr) cm$^{-1}$: 3250, 1725, 1620, 1480, 1450, 1375, 1330

EXAMPLE 13

(1) There were mixed 3.21 g of methyl 2-hydroxy-7-methylsulfonylamino-6-phenoxyphenyl ketone, 50 ml of ethyl acetate and 3.2 g of sodium hydride (purity: 60%). The mixture was refluxed for 4 hours. The reaction mixture was introduced into 200 ml of ice water. The aqueous layer was separated, adjusted to pH 4 with 4N hydrochloric acid and extracted with two 50-ml portions of ethyl acetate. The extracts were combined, washed with water and a saturated aqueous sodium chloride solution in this order, and dried with anhydrous magnesium sulfate. The solvent was removed by distillation under reduced pressure. The residue was mixed with toluene. The resulting crystal was collected by filtration and recrystallized from a mixed solvent of ethyl acetate and diisopropyl ether to obtain 2.65 g (yield: 73%) of 2-(2-hydroxy-4-methylsulfonylamino-5-phenoxybenzoyl)acetone having a melting point of 142°–143° C.

IR (KBr) cm$^{-1}$: 3230, 1620, 1580, 1490, 1345, 1320, 1250, 1220, 1160, 1130

(2) 3.63 g of 2-(2-hydroxy-4-methylsulfonylamino-5-phenoxybenzoyl)acetone was dissolved in 18 ml of N,N-dimethylformamide. Thereto was added 2.62 g of N,N-dimethylformamide dimethylacetal. The mixture was stirred for 1 hour at 20°–25° C. The reaction mixture was introduced into 100 ml of water. The resulting mixture was adjusted to pH 5 with 4N hydrochloric acid and then extracted with 100 ml of ethyl acetate. The extract was washed with water and a saturated aqueous sodium chloride solution in this order, and dried with anhydrous sodium sulfate. The solvent was removed by distillation under reduced pressure. The residue was recrystallized from ethanol to obtain 2.38 g (yield: 64%) of 3-acetyl-7-methylsulfonylamino-6-phenoxy-4H-1-benzopyran-4-one having a melting point of 175°–177° C.

IR (KBr) cm$^{-1}$: 3220, 1680, 1640, 1620, 1485, 1450, 1330, 1295, 1210, 1155

EXAMPLE 14

5.0 g of methyl 2-hydroxy-4-methylsulfonylamino-5-phenoxyphenyl ketone was suspended in 85 ml of ethanol. Thereto was added 4.5 ml of diethyl oxalate. Further, 3.1 g of sodium hydride (purity: 60%) was added thereto in portions in 10 minutes. The mixture was refluxed for 1.5 hours. The reaction mixture was introduced into 300 ml of ice water. The resulting mixture was adjusted to pH 2 with 4N hydrochloric acid. The resulting crystal was collected by filtration and then suspended in 50 ml of acetic acid. 1 ml of concentrated hydrochloric acid was added thereto. The mixture was stirred for 10 minutes at 80° C. After the completion of the reaction, 200 ml of water and 200 ml of ethyl acetate were added thereto. The organic layer was separated, washed with water and a saturated aqueous sodium chloride solution in this order, and dried with anhydrous magnesium sulfate. The solvent was removed by distillation under reduced pressure. The residue was recrystallized from a mixed solvent of ethyl acetate and diisopropyl ether to obtain 3.5 g (yield: 56%) of 2-ethoxycarbonyl-7-methylsulfonylamino-6-phenoxy-4H-1-benzopyran-4-one having a melting point of 155°–156° C.

IR (KBr) cm$^{-1}$: 3235, 1740, 1645, 1620, 1485, 1450, 1360, 1250, 1145

EXAMPLE 15

1.06 ml of acetic anhydride was added to 2.0 g of methyl 2-hydroxy-4-methylsulfonylamino-5-(2,4-difluorophenoxy)phenyl ketone and 550 mg of sodium acetate. The mixture was refluxed for 1 hour. The reaction mixture was introduced into a mixture of 50 ml of ethyl acetate and 50 ml of water. The organic layer was separated and washed with water. The solvent was removed by distillation under reduced pressure. The residue was dissolved in 20 ml of ethanol. 12 ml of a 1N aqueous sodium hydroxide solution was added thereto. The mixture was refluxed for 10 minutes. The reaction mixture was introduced into a mixture of 50 ml of ethyl acetate and 50 ml of water. The resulting mixture was adjusted to pH 2.0 with 4N hydrochloric acid. The organic layer was separated, washed with water, and dried with anhydrous magnesium sulfate. The solvent was removed by distillation under reduced pressure. The residue was purified by a column chromatography (eluant: a 10 : 1 mixture of toluene and ethyl acetate) to obtain 300 mg (yield: 14.4%) of 7-methylsulfonylamino-2-methyl-6-(2,4-difluorophenoxy)-4H-1-benzopyran-4-one.

Melting point: 180°–181° C. (recrystallized from isopropyl alcohol)

IR (KBr) cm$^{-1}$: 3100, 1640, 1605, 1500, 1460, 1390, 1360, 1160, 1140

EXAMPLE 16

3.93 g of ethyl 2-(2-hydroxy-4-methylsulfonylamino-5-phenoxybenzoyl)acetate was dissolved in 20 ml of N,N-dimethylformamide. Thereto was added 880 mg of sodium hydride (purity: 60%). The mixture was stirred for 30 minutes at 25°–30° C. The reaction mixture was introduced into 100 ml of ice water. Thereto was added 50 ml of diethyl ether. The aqueous layer was separated, adjusted to pH 5 with 4N hydrochloric acid, and extracted with two 50-ml portions of ethyl acetate. The extracts were combined, washed with water and a saturated aqueous sodium chloride solution in this order, and dried with anhydrous magnesium sulfate. The solvent was removed by distillation under reduced pressure. The residue was recrystallized from acetonitrile to obtain 3.05 g (yield: 87.9%) of 2-hydroxy-7-methylsulfonylamino-6-phenoxy-4H-1-benzopyran-4-one having a melting point of >250° C.

IR (KBr) cm$^{-1}$: 3530, 3400, 3300, 1680, 1620, 1560, 1480, 1330, 1225, 1140

EXAMPLE 17

(1) In 25 ml of methanol were suspended 2.0 g of methyl 2-hydroxy-4-methylsulfonylamino-5-phenoxyphenyl ketone and 1.03 g of 3,4-dimethoxybenzaldehyde. Thereto was added 5 ml of 50% aqueous sodium hydroxide. The mixture was stirred for 3 hours at room temperature. The reaction mixture was introduced into a mixture of 20 ml of ethyl acetate and 20 ml of water. The resulting mixture was adjusted to pH 2.0 with 4N hydrochloric acid. The resulting crystal was collected by filtration, washed with water and ethyl acetate in this order, and recrystallized from acetic acid to obtain 2.2 g (yield: 75.6%) of 2-(3,4-dimethoxyphenyl)vinyl 2-hydroxy-4-methylsulfonylamino-5-phenoxyphenyl ketone.

Melting point: 210°–212° C. (recrystallized from acetic acid)

IR (KBr) cm$^{-1}$: 3520, 3250, 1625, 1490, 1340, 1155, 1120

(2) 2.0 g of 2-(3,4-dimethoxyphenyl)vinyl 2-hydroxy-4-methylsulfonylamino-5-phenoxyphenyl ketone was suspended in 20 ml of methanol. Thereto was added 3.7 ml of a 15% aqueous sodium hydroxide solution to obtain a solution. Thereto was dropwise added 2.5 ml of a 15% aqueous hydrogen peroxide solution in 10 minutes at 0°–5° C. The mixture was stirred for 10 hours at the same temperature. The reaction mixture was introduced into a mixture of 50 ml of ethyl acetate and 50 ml of water. The organic layer was separated, washed with water, and dried with anhydrous magnesium sulfate. The solvent was removed by distillation under reduced pressure. The residue was purified by a column chromatography (eluant: a 200 : 1 mixture of chloroform and methanol) to obtain 220 mg (yield: 10.7%) of 3-hydroxy-7-methylsulfonylamino-2-(3,4-dimethoxyphenyl)-6-phenoxy-4H-1-benzopyran-4-one.

Melting point: 222°–223.5° C. (recrystallized from acetonitrile)

IR (KBr) cm$^{-1}$: 3225, 1630, 1490, 1320, 1210, 1160, 1120

EXAMPLE 18

(1) 3.47 g of 2-hydroxy-7-methylsulfonylamino-6-phenoxy-4H-1-benzopyran-4-one was suspended in 50 ml of acetic acid. Thereto was added 1.67 ml of concentrated nitric acid (specific gravity: 1.38). The mixture was stirred for 20 minutes at 100°–110° C. The reaction mixture was introduced into 300 ml of ice water. The resulting crystal was collected by filtration, washed with water, and recrystallized from acetonitrile to obtain 800 mg (yield: 20.4%) of 2-hydroxy-7-methylsulfonylamino-3-nitro-6-phenoxy-4H-1-benzopyran-4-one having a melting point of 228°–230° C. (decomposed).

IR (KBr) cm$^{-1}$: 3300, 1755, 1740, 1620, 1600, 1535, 1485, 1440, 1390, 1330, 1205, 1145

(2) 3.92 g of 2-hydroxy-7-methylsulfonylamino-3-nitro-6-phenoxy-4H-1-benzopyran-4-one was mixed with 80 ml of a 1N aqueous sodium hydroxide solution. The mixture was stirred for 5 hours at 20°–25° C. The mixture was adjusted to pH 5 with 4N hydrochloric acid. 50 ml of ethyl acetate was added thereto. The organic layer was separated, washed with water and a saturated aqueous sodium chloride solution in this order, and dried with anhydrous magnesium sulfate. The solvent was removed by distillation under reduced pressure. The resulting yellow solid was dissolved in N,N-dimethylformamide. 2.62 g of N,N-dimethylformamide dimethylacetal was added thereto. The mixture was stirred for 1 hour at 20°–25° C. The reaction mixture was introduced into 300 ml of water. The resulting mixture was adjusted to pH 2 with 4N hydrochloric acid. The precipitate was washed with water and then recrystallized from acetonitrile to obtain 1.54 g (yield: 41%) of 3-nitro-7-methylsulfonylamino-6-phenoxy-4H-1-benzopyran-4-one having a melting point of 225°–227° C.

IR (KBr) cm$^{-1}$: 3170, 3070, 1670, 1620, 1480, 1450, 1330, 1300, 1150

EXAMPLE 19

The compounds shown in Table 24 were obtained in the same manner as in Examples 7 to 18.

The physical properties of these compounds were identical with those of the compounds in Examples 1 to 4.

TABLE 24

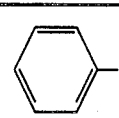

| $R^1$ | $R^2$ | $R^3$ | $R^4$ | $R^5$ | Z |
|---|---|---|---|---|---|
| Me | H | H | —OCH$_3$ | 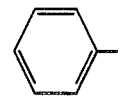 | O |
| Me | H | H | OH | 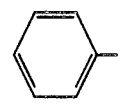 | O |
| Me | H | H | —SCH$_3$ | 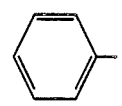 | O |
| Me | H | H | $\overset{O}{\underset{}{\uparrow}}$—SCH$_3$ | 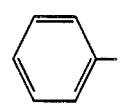 | O |
| Me | H | H | —S(=O)$_2$CH$_3$ | 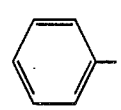 | O |
| Et | H | H | H | 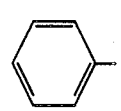 | O |
| —CF$_3$ | H | H | H | 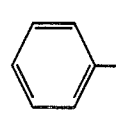 | O |
| Me | H | Me | H | 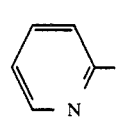 | O |
| Me | H | H | H | pyridyl | O |

TABLE 24-continued

| R¹ | R² | R³ | R⁴ | R⁵ | Z |
|---|---|---|---|---|---|
| Me | H | Ph | H | Ph | O |
| Me | H | H | H | Ph | NH |
| Me | H | H | H | 2-CF₃-C₆H₄ | O |
| Me | H | H | H | 3-pyridyl | O |
| Me | H | H | H | 2-F-C₆H₄ | O |
| Me | H | H | H | 3-F-C₆H₄ | O |
| Me | H | H | H | 4-F-C₆H₄ | O |
| Me | H | H | H | 2-Cl-C₆H₄ | O |
| Me | H | H | H | 4-Cl-C₆H₄ | O |
| Me | H | H | H | 2-Me-C₆H₄ | O |
| Me | H | H | H | 4-Me-C₆H₄ | O |

TABLE 24-continued
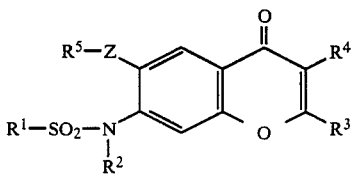
| R¹ | R² | R³ | R⁴ | R⁵ | Z |
|---|---|---|---|---|---|
| 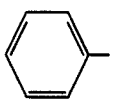 | H | H | H | 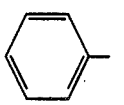 | O |
| Me | H | H | —NH₂ | 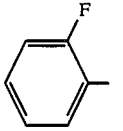 (F ortho) | O |
| Me | H | H | —NH₂ | 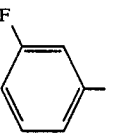 (F meta) | O |
| Me | H | H | —NH₂ | 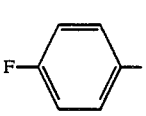 (F para) | O |
| Me | H | H | —NH₂ | 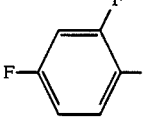 (2,4-diF) | O |
| Me | H | Me | —NH₂ | 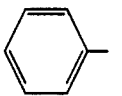 | O |
| ClCH₂— | H | H | —NH₂ | 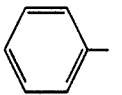 | O |
| Et | H | H | —NH₂ | 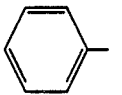 | O |
| Me | H | H | —NH₂ | 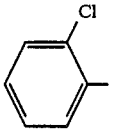 (Cl ortho) | O |
| Me | H | H | —NH₂ | 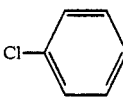 (Cl para) | O |

TABLE 24-continued

| R¹ | R² | R³ | R⁴ | R⁵ | Z |
|---|---|---|---|---|---|
| Me | H | H | —NH₂ | 2-methylphenyl | O |
| Me | H | H | —NH₂ | 4-methylphenyl | O |
| Me | H | H | —NCHO<br>H | 2-fluorophenyl | O |
| Me | H | H | —NCHO<br>H | 3-fluorophenyl | O |
| Me | H | H | —NCHO<br>H | 4-fluorophenyl | O |
| Me | H | Me | —NCHO<br>H | phenyl | O |
| Me | H | H | —NAc<br>H | phenyl | O |
| Me | H | H | —NCHO<br>H | 3,4-difluorophenyl | O |
| ClCH₂— | H | H | —NCHO<br>H | phenyl | O |
| Me | H | H | —NCO—(CH₂)₂—CO₂H<br>H | phenyl | O |
| Et | H | H | —NCHO<br>H | phenyl | O |

TABLE 24-continued
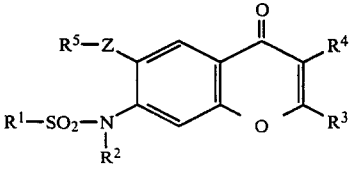
| R¹ | R² | R³ | R⁴ | R⁵ | Z |
|---|---|---|---|---|---|
| —CF₃ | H | H | —NCHO<br>H |  | O |
| Me | H | H | —NCHO<br>H | 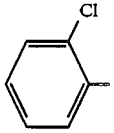 (Cl, ortho) | O |
| Me | H | H | —NCHO<br>H | 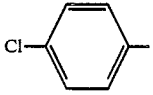 (Cl, para) | O |
| Me | H | H | —NCHO<br>H | 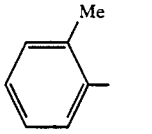 (Me, ortho) | O |
| Me | H | H | —NCHO<br>H | 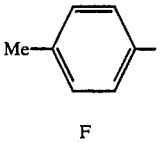 (Me, para) | O |
| Me | H | H | Me<br>—NCHO | 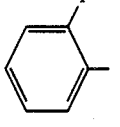 (F, ortho) | O |
| Me | H | H | Me<br>—NCHO | 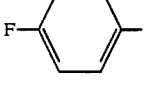 (F, para) | O |
| Me | H | H | Et<br>—NCHO |  | O |
| Me | H | H | Me<br>—NAc |  | O |
| Me | H | H | —NCHO<br>$\vert$<br>CH₂<br>$\vert$<br>CO₂Me |  | O |
| Me | H | H | —NCHO<br>$\vert$<br>(CH₂)₃<br>$\vert$<br>CO₂Et |  | O |

TABLE 24-continued
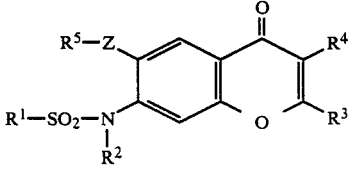
| R¹ | R² | R³ | R⁴ | R⁵ | Z |
|---|---|---|---|---|---|
| Me | H | H | -NHCOPh | Ph | O |
| Me | H | H | -NH-CO-CO₂Et | Ph | O |
| Me | H | H | -N(Me)₂ | Ph | O |
| Me | H | H | -N(pyrrolidinyl) | Ph | O |
| Me | H | H | -NHOH | Ph | O |
| Me | H | H | -CHO | 2-F-C₆H₄ | O |
| Me | H | H | -CHO | 2,4-F₂-C₆H₃ | O |
| Me | H | Me | -CONH₂ | Ph | O |
| Me | H | H | -CONHMe | Ph | O |
| Me | H | H | -CONH-cyclopropyl | Ph | O |
| Me | H | H | -CONHPh | Ph | O |

TABLE 24-continued
| R¹ | R² | R³ | R⁴ | R⁵ | Z |
|---|---|---|---|---|---|
| Me | H | H | —CONHOMe | 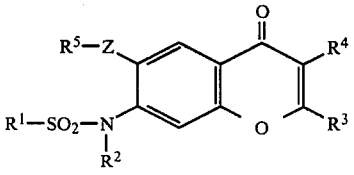 | O |
| Me | H | H | —CON(Me)Me |  | O |
| Me | H | H | —CON(piperidine) |  | O |
| Me | H | H | —CONH-(2-pyridyl) |  | O |
| Me | H | —CF₃ | H |  | O |
| Me | H | Et | H |  | O |
| Me | H | -i-Pr | H |  | O |
| Me | H | cyclopropyl | H |  | O |
| Me | H | H | H |  | O |
| Me | H | H | H |  | O |
| Me | H | H | H |  | O |
| Me | H | H | H |  | O |

TABLE 24-continued
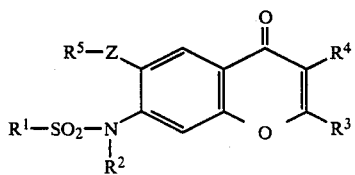
| R¹ | R² | R³ | R⁴ | R⁵ | Z |
|----|----|----|----|----|----|
| Me | H | H | H | 2-CONH₂-C₆H₄ | O |
| Me | H | H | H | 2-(i-Pr)-C₆H₄ | O |
| Me | H | H | H | 2,3-Me₂-C₆H₃ | O |
| Me | H | H | H | 4-F-2-Me-C₆H₃ | O |
| Me | H | H | H | C₆H₅ | S |
| Me | H | H | -CH₂-C₆H₅ | C₆H₅ | O |
| Me | H | H | Et | C₆H₅ | O |
| Me | H | H | C₆H₅ | C₆H₅ | O |
| Me | H | H | -i-Pr | C₆H₅ | O |
| Me | H | H | -N(H)CHO | 3-Me-C₆H₄ | O |

TABLE 24-continued

Structure: R⁵-Z and R¹-SO₂-N(R²) substituents on a chromone ring with R³, R⁴ substituents and carbonyl group.

| R¹ | R² | R³ | R⁴ | R⁵ | Z |
|---|---|---|---|---|---|
| Me | H | H | —NHCHO | 4-F-2-Me-phenyl | O |
| Me | H | H | —NHCHO | phenyl | S |
| Me | H | H | —NHAc | 2-F-phenyl | O |
| Me | H | H | —CH=NOH | 2-F-phenyl | O |
| Me | H | H | —CH=NOH | 2,4-F₂-phenyl | O |
| Me | H | H | —CN | 2-F-phenyl | O |
| Me | H | H | —CN | 2,4-F₂-phenyl | O |
| Me | H | H | H | 2,4-F₂-phenyl | O |
| Me | Ac | H | H | phenyl | O |
| Me | H | H | Me | phenyl | O |

TABLE 24-continued

![structure: R5-Z and R1-SO2-N(R2)- substituted chromone with R3, R4]

| R¹ | R² | R³ | R⁴ | R⁵ | Z |
|---|---|---|---|---|---|
| Me | H | H | —NH₂ | Ph | O |
| Me | H | H | —N(H)CHO | Ph | O |
| Me | H | H | —N(Me)CHO | Ph | O |
| Me | H | H | —N(H)Me | Ph | O |
| Me | H | H | —N(H)Et | Ph | O |
| Me | H | H | —N(H)CO₂Me | Ph | O |
| Me | H | H | Br | Ph | O |
| Me | H | H | Cl | Ph | O |
| Me | H | H | —N(H)CONH₂ | Ph | O |
| Me | H | H | —N(Me)CONH₂ | Ph | O |
| Me | Ac | H | succinimido (N-linked 2,5-dioxopyrrolidine) | Ph | O |

TABLE 24-continued
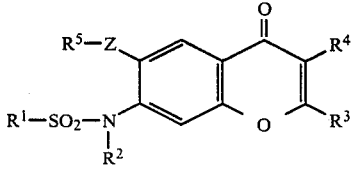
| R¹ | R² | R³ | R⁴ | R⁵ | Z |
|---|---|---|---|---|---|
| Me | H | H | —NCHO<br>\|<br>CH₂<br>\|<br>CO₂H | 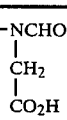 | O |
| Me | H | Br | —NH₂<br>(hydrobromic acid salt form) | 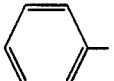 | O |
| Me | H | Br | —NCHO<br>\|<br>H | 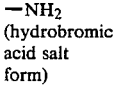 | O |
| Me | H | —OMe | —NCHO<br>\|<br>H |  | O |
| Me | H | —OH | —NCHO<br>\|<br>H |  | O |
| Me | H | —CN | —NCHO<br>\|<br>H |  | O |
| Me | H | H |  |  | O |
| Me | H | H |  |  | O |
| Me | H | H | —CONH₂ |  | O |
| Me | H | —COOH | H | 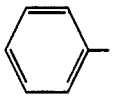 | O |
| Me | H | —CONH₂ | H |  | O |
| Me | H | —CH₂OH | H | 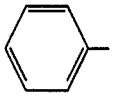 | O |

TABLE 24-continued

| R¹ | R² | R³ | R⁴ | R⁵ | Z |
|---|---|---|---|---|---|
| Me | H | —NCOOEt<br>H | H | phenyl | O |
| Me | H | —NCOOt—Bu<br>H | H | phenyl | O |
| Me | H | —NCHO<br>H | H | phenyl | O |
| Me | H | —NAc<br>H | H | phenyl | O |
| Me | H | —NH₂ | H | phenyl | O |
| Me | H | Me | H | 2,4-difluorophenyl | O |
| Me | H | H | —CH₂OH | phenyl | O |
| Me | H | H | —CH=CH—phenyl | phenyl | O |
| Me | H | H | —CHCH₃<br>\|<br>OH | phenyl | O |
| Me | H | H | —CH₂NAc<br>H | phenyl | O |
| Me | H | H | —CH₂NH₂ | phenyl | O |

TABLE 24-continued
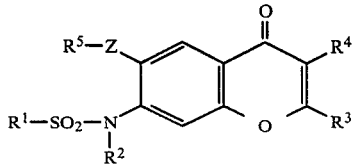
| R¹ | R² | R³ | R⁴ | R⁵ | Z |
|----|----|----|----|----|---|
| Me | H | H |  (thiazole) | 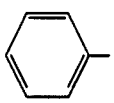 (phenyl) | O |
| Me | H | —OH | H | 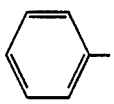 (phenyl) | O |
| Me | H | H | —N=CHN(Me)(Me) | 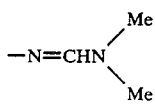 (phenyl) | O |
| Me | H | H | —NCCHCH₃ / H∥ / OOH |  (phenyl) | O |
| Me | H | H | —NCCHCH₃ / H∥ / ONH₂ | 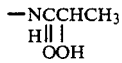 (phenyl) | O |
| Me | H | H | —NSO₂Me / H | 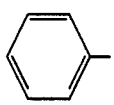 (phenyl) | O |
| Me | H |  (2,3-dimethoxyphenyl) | —OH | 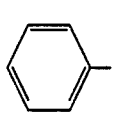 (phenyl) | O |
| Me | H | H | H | 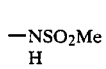 (2-COOH-phenyl) | O |
| Me | H | H | H | 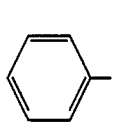 (2-NH₂-phenyl) | O |
| Me | H | H | H | 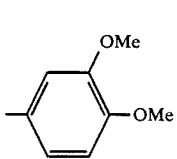 (2-NHAc-phenyl) | O |

TABLE 24-continued

Structure: chromone with R⁵-Z and R¹-SO₂-N(R²)- substituents on the benzene ring, R³ and R⁴ on the pyranone ring.

| R¹ | R² | R³ | R⁴ | R⁵ | Z |
|----|----|----|----|----|---|
| Me | H | H | H | 2-(NHCHO)-phenyl | O |
| Me | H | H | H | 2-OMe-phenyl | O |
| Me | H | H | H | 4-MeO-phenyl | O |
| Me | H | H | H | 3-Me-phenyl | O |
| Me | H | H | H | 2-OH-phenyl | O |
| Me | H | H | —NHCHO | 2-OMe-phenyl | O |
| Me | H | H | —CH=NOH | phenyl | O |
| Me | H | H | —CN | phenyl | O |
| Me | H | H | —CONH₂ | 2-F-phenyl | O |
| Me | H | H | —CONH₂ | 2,4-diF-phenyl | O |

TABLE 24-continued
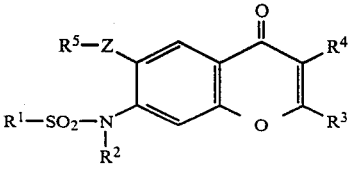
| R¹ | R² | R³ | R⁴ | R⁵ | Z |
|---|---|---|---|---|---|
| Me | H | —OH | —NO₂ | 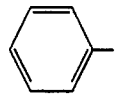 | O |
| Me | H | H | —NO₂ | 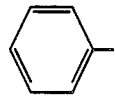 | O |
| CH₂=CH— | H | H | H | 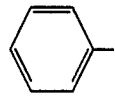 | O |
| Me | Ac | H | H | 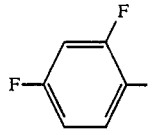 | O |
| Me | Ac | H | —NCHO<br>    H | 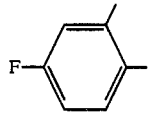 | O |
| Me | Bz | H | H | 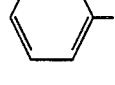 | O |
| Me | Me | H | H | 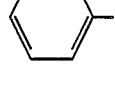 | O |
| Me | H | H | 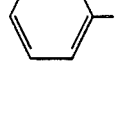 | 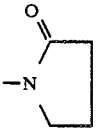 | O |
| Me | H | H | 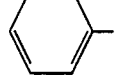 | 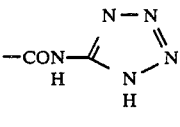 | O |
| Me | H | H | 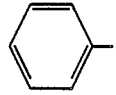 | 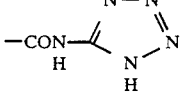 | O |
| Me | H | 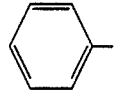 | H | 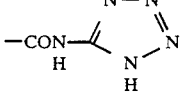 | O |

TABLE 24-continued

[Structure: R⁵-Z and R¹-SO₂-N(R²)- substituted benzopyranone with R³, R⁴ substituents]

| R¹ | R² | R³ | R⁴ | R⁵ | Z |
|---|---|---|---|---|---|
| Me | H | H | tetrazolyl (N—N/N—N with H) | phenyl | O |
| Me | H | —NH₂ | —CONH₂ | phenyl | O |
| Me | H | Me | Me | phenyl | O |

EXAMPLE 20

(1) 8.0 g of sodium hydroxide was dissolved in 240 ml of water. In this solution was dissolved 24.3 g of 3-acetylamino-4-phenoxyphenol. Thereto was added 10.9 g of 3-chloropropionic acid. The mixture was refluxed for 30 minutes. The reaction mixture was water-cooled. The resulting crystal was removed by filtration. The filtrate was adjusted to pH 9 with 4N hydrochloric acid and washed with two 50-ml portions of ethyl acetate. The aqueous layer was separated, adjusted to pH 4 with 4N hydrochloric acid, and extracted with 200 ml of ethyl acetate. The extract (the organic layer) was washed with water and a saturated aqueous sodium chloride solution in this order, and dried with anhydrous magnesium sulfate. The solvent was removed by distillation under reduced pressure. The resulting crystal was mixed with diethyl ether. The resulting crystal was collected by filtration to obtain 10.0 g (yield: 31.7%) of 3-(3-acetylamino-4-phenoxyphenoxy)propionic acid having a melting point of 138°-140° C.

IR (KBr) cm⁻¹: 3270, 1730, 1630, 1590, 1540, 1475, 1425, 1220

NMR (d₆-DMSO) δ: 2.00 (3H, s), 2.68 (2H, t, J=6Hz), 4.14 (2H, t, J=6Hz), 6.50-7.92 (7H, m), 7.67 (1H, d, J=2.4Hz), 9.22 (1H, bs)

(2) The following compound was obtained in the same manner as in Example 1 (2).

7-Acetylamino-2,3-dihydro-6-phenoxy-4H-1-benzopyran-4-one

Melting point: 214°-215° C. (recrystallized from acetonitrile-ethyl acetate)

IR (KBr) cm⁻¹: 3305, 1700, 1665, 1615, 1590, 1520, 1438, 1270, 1245, 1220

NMR (CDCl₃+d₆-DMSO) δ: 2.16 (3H, s), 2.69 (2H, t, J=6Hz), 4.49 (2H, t, J=6Hz), 6.75-7.54 (5H, m), 7.19 (1H, s), 8.06 (1H, s), 9.32 (1H, bs)

(3) The following compound was obtained in the same manner as in Example 1 (3).

7-Acetylamino-6-phenoxy-4H-1-benzopyran-4-one

Melting point: 233°-235° C. (recrystallized from chloroform-ethanol)

IR (KBr) cm⁻¹: 3250, 3060, 1695, 1635, 1510, 1435, 1303, 1245, 1210

NMR (d₆-DMSO) δ: 2.22 (3H, s), 6.24 (1H, d, J=6Hz), 7.10-7.63 (6H, m), 8.21 (1H, d, J=6Hz), 8.53 (1H, s), 9.91 (1H, bs)

(4) 2.95 g of 7-acetylamino-6-phenoxy-4H-1-benzopyran-4-one was dissolved in 30 ml of N,N-dimethylformamide. 440 mg of sodium hydride (purity: 60%) was added thereto with ice-cooling. The mixture was stirred at the same temperature until the generation of hydrogen gas stopped. Then, 1.26 g of methanesulfonyl chloride was added thereto dropwise. The mixture was stirred for 1 hour at 20°-25° C. 200 ml of water and 200 ml of ethyl acetate were added thereto. The organic layer was separated, washed with water and a saturated aqueous sodium chloride solution in this order, and dried with anhydrous magnesium sulfate. The solvent was removed by distillation under reduced pressure. The resulting crystal was recrystallized from ethanol to obtain 3.22 g (yield: 86.1%) of 7-(N-acetyl-N-methylsulfonylamino)-6-phenoxy-4H-1-benzopyran-4-one having a melting point of 166°-169° C.

IR (KBr) cm⁻¹: 1700, 1640, 1620, 1480, 1445, 1360, 1295, 1155

NMR (CDCl₃) δ: 2.12 (3H, s), 3.40 (3H, s), 6.30 (1H, d, J=6Hz), 7.11-7.63 (7H, m), 7.86 (1H, d, J=6Hz)

EXAMPLE 21

2.95 g of 7-acetylamino-6-phenoxy-4H-1-benzopyran-4-one was dissolved in 30 ml of N,N-dimethylformamide. 1.35 g of potassium tert-butoxide was added with ice-cooling. The mixture was stirred for 30 minutes at the same temperature. Then, 1.55 g of ethanesulfonyl chloride was added thereto dropwise. The mixture was stirred for 1 hour at 20°-25° C. 200 ml of water and 200 ml of ethyl acetate were added. The organic layer was separated. The solvent was removed by distillation under reduced pressure. The resulting crystal was mixed with 20 ml of a 1N aqueous sodium hydroxide solution and 10 ml of ethanol. The mixture was refluxed for 2 hours. 100 ml of water and 100 ml of ethyl acetate were added thereto. The mixture was adjusted to pH 4 with 4N hydrochloric acid. The organic layer was separated. The layer was washed with water and a saturated aqueous NaCl solution in this order, and dried with anhydrous magnesium sulfate. The solvent was removed by distillation under reduced pressure. The residue was purified by a column chromatography (eluant: a mixture of 5:1 toluene and ethyl acetate) to obtain 0.75 g (yield: 21.7%) of 7-ethylsulfonylamino-6-phenoxy-4H-1-benzopyran-4-one.

Melting point: 216°–218° C. (recrystallized from ethanol)

IR (KBr) cm$^{-1}$: 3070, 1620, 1582, 1490, 1455, 1335, 1200, 1155, 1138

NMR (CDCl$_3$+d$_6$-DMSO) δ: 1.37 (3H, t, J=7.2Hz), 3.25 (2H, q, J=7.2Hz), 6.22 (1H, d, J=6Hz), 7.01–7.47 (5H, m), 7.68 (1H, s), 7.76 (1H, s), 7.93 (1H, d, J=6Hz), 9.21 (1H, bs)

EXAMPLE 22

(1) There were mixed 29.7 g of 7-acetylamino-2,3-dihydro-6-phenoxy-4H-1-benzopyran-4-one, 30 ml of ethanol and 300 ml of 6N hydrochloric acid. The mixture was refluxed for 1 hour. The reaction mixture was introduced into 3 liters of ice water. The resulting crystal was collected by filtration and recrystallized from ethanol to obtain 23.5 g (yield: 92.2%) of 7-amino-2,3-dihydro-6-phenoxy-4H-1-benzopyran-4-one having a melting point of 154°–155° C.

IR (KBr) cm$^{-1}$: 3470, 3330, 1655, 1610, 1570, 1500, 1460, 1320, 1300, 1255

(2) In 200 ml of pyridine was dissolved 25.5 g of 7-amino-2,3-dihydro-6-phenoxy-4H-1-benzopyran-4-one. To the solution being maintained at 20°–25° C. was dropwise added 12.6 g of methanesulfonyl chloride. The mixture was subjected to reaction for 12 hours at the same temperature. The solvent was removed by distillation under reduced pressure. The residue was dissolved in 200 ml of ethyl acetate. The solution was extracted with two 500-ml portions of a 1N aqueous sodium hydroxide solution. The extracts (the aqueous layers) were combined, adjusted to pH 4 with 4N hydrochloric acid, and extracted with two 300-ml portions of ethyl acetate. The extracts (the organic layers) were combined, washed with water and a saturated aqueous sodium chloride solution in this order, and dried with anhydrous magnesium sulfate. The solvent was removed by distillation under reduced pressure. The resulting crystal was recrystallized from methanol to obtain 27.0 g (yield: 81.1%) of 2,3-dihydro-7-methylsulfonylamino-6-phenoxy-4H-1-benzopyran-4-one.

The properties (melting point and IR) of this compound agreed with those of the compound obtained in Example 1 (2).

The compounds shown in Tables 25 and 26 were obtained in the same manner.

TABLE 25

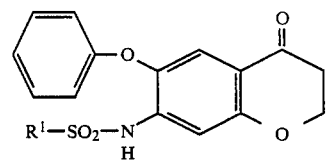

| R$^1$ | Melting point (°C.) | IR (KBr) cm$^{-1}$: |
|---|---|---|
| ClCH$_2$— | 158–160 [IPA] | 3150, 1660, 1610, 1480, 1440, 1255, 1190, 1160, 1140 |
| Et | 174–175 [Ethanol] | 3020, 1665, 1620, 1500, 1450, 1330, 1270 |
| *CH$_2$=CH— | 132–136 (dec.) [Ethyl acetate-IPE] | 3050, 1660, 1605, 1485, 1325, 1265, 1220, 1135 |

Note:
*2-Chloroethansulfonyl chloride was used in place of the methansulfonyl chloride.

TABLE 26

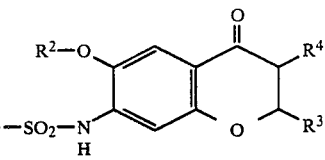

| R$^1$ | R$^3$ | R$^4$ | R$^5$ | Melting point (°C.) | IR (KBr) cm$^{-1}$ |
|---|---|---|---|---|---|
| Me | H | H | (2-F-phenyl) | 131–132 [Ethanol] | 3240, 1670, 1610, 1490, 1440, 1325, 1255 |
| Me | H | H | (3-F-phenyl) | 146–174 [Ethanol] | 3100, 1670, 1490, 1325, 1270, 1145 |

TABLE 26-continued
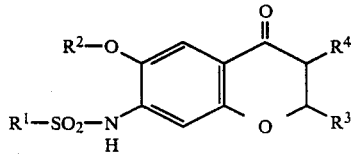
| $R^1$ | $R^3$ | $R^4$ | $R^5$ | Melting point (°C.) | IR (KBr) cm$^{-1}$ |
|---|---|---|---|---|---|
| Me | H | H | 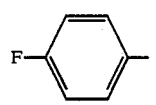 | 167-168 [Ethanol] | 3175, 1670, 1615, 1490, 1440, 1340, 1260 |
| Me | H | H | 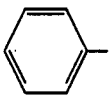 | 143-144 [Methanol] | 3120, 1665, 1610, 1485, 1440, 1320, 1265, 1215, 1160, 1135, |
| —CF$_3$ | H | H | 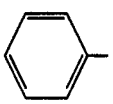 | 128-130 [IPE] | 3140, 1680, 1610, 1480, 1440, 1370, 1260, 1230, 1210, 1200, 1135 |
| Me | Me | H | 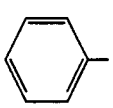 | 144-145 [Ethanol] | 1665, 1610, 1495, 1440, 1320, 1260, 1215, 1135 |
| Me | H | H | 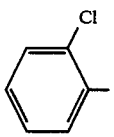 | 130-131 [Ethanol] | 3230, 1680, 1610, 1470, 1440, 1320, 1255, 1160 |
| Me | H | H | 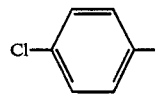 | 144-146 [Ethanol] | 3250, 1670, 1610, 1480, 1440, 1320, 1255, 1160 |
| Me | H | H | 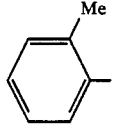 | 157-159 [Toluene] | 3230, 1690, 1610, 1480, 1440, 1340, 1260, 1160 |
| Me | H | H | 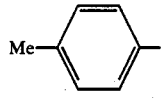 | 120-121 [Toluene] | 3250, 1680, 1615, 1490, 1440, 1340, 1320, 1260, 1135 |
| Me | H | H | 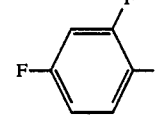 | 163.5-165 [Ethanol] | 3220, 1665, 1605, 1575, 1495, 1420 |
| Me | H | Br | 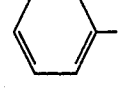 | 137-140 [Toluene] | 3250, 1680, 1610, 1485, 1325, 1260, 1205 |
| Me | H | —OMe | 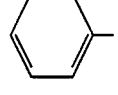 | 139-141 [Ethanol] | 3230, 1680, 1610, 1490, 1450, 1330, 1260, 1210, 1150 |

TABLE 26-continued

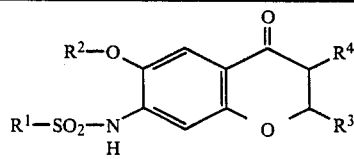

| R¹ | R³ | R⁴ | R⁵ | Melting point (°C.) | IR (KBr) cm⁻¹ |
|---|---|---|---|---|---|
| Me | H | —SMe | 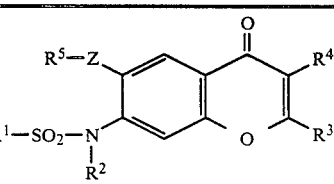 | 126–128 [Ethanol] | 3250, 1690, 1610, 1480, 1440, 1340, 1260, 1220, 1160, 1140 |

EXAMPLE 23

The compounds shown in Table 27 were obtained in the same manner as in Example 20, 21 or 23.

The physical properties of these compounds were identical with those of the compounds in Examples 1 to 4.

TABLE 27

| R¹ | R² | R³ | R⁴ | R⁵ | Z |
|---|---|---|---|---|---|
| Me | H | H | H |  | O |
| Me | H | H | —OMe |  | O |
| Me | H | H | —SMe |  | O |
| Me | H | H | $\underset{-\text{SMe}}{\overset{O}{\uparrow}}$ |  | O |
| Me | H | H | $\underset{\underset{O}{\overset{\|}{\text{S}}\text{Me}}}{\overset{O}{\|}}$ |  | O |
| Et | H | H | H | 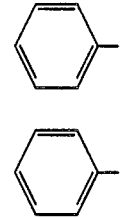 | O |
| —CF₃ | H | H | H |  | O |
| Me | H | Me | H |  | O |

TABLE 27-continued
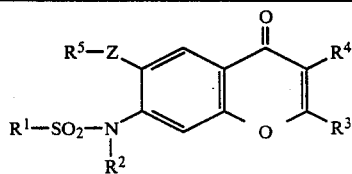
| R¹ | R² | R³ | R⁴ | R⁵ | Z |
|----|----|----|----|----|---|
| Me | H | H | H | 2-pyridyl | O |
| Me | H | phenyl | H | phenyl | O |
| Me | H | H | H | phenyl | HN |
| Me | H | H | H | 3-CF₃-phenyl | O |
| Me | H | H | H | 3-pyridyl | O |
| Me | H | H | H | 2-F-phenyl | O |
| Me | H | H | H | 3-F-phenyl | O |
| Me | H | H | H | 4-F-phenyl | O |
| Me | H | H | H | 2-Cl-phenyl | O |
| Me | H | H | H | 4-Cl-phenyl | O |
| Me | H | H | H | 2-Me-phenyl | O |

TABLE 27-continued
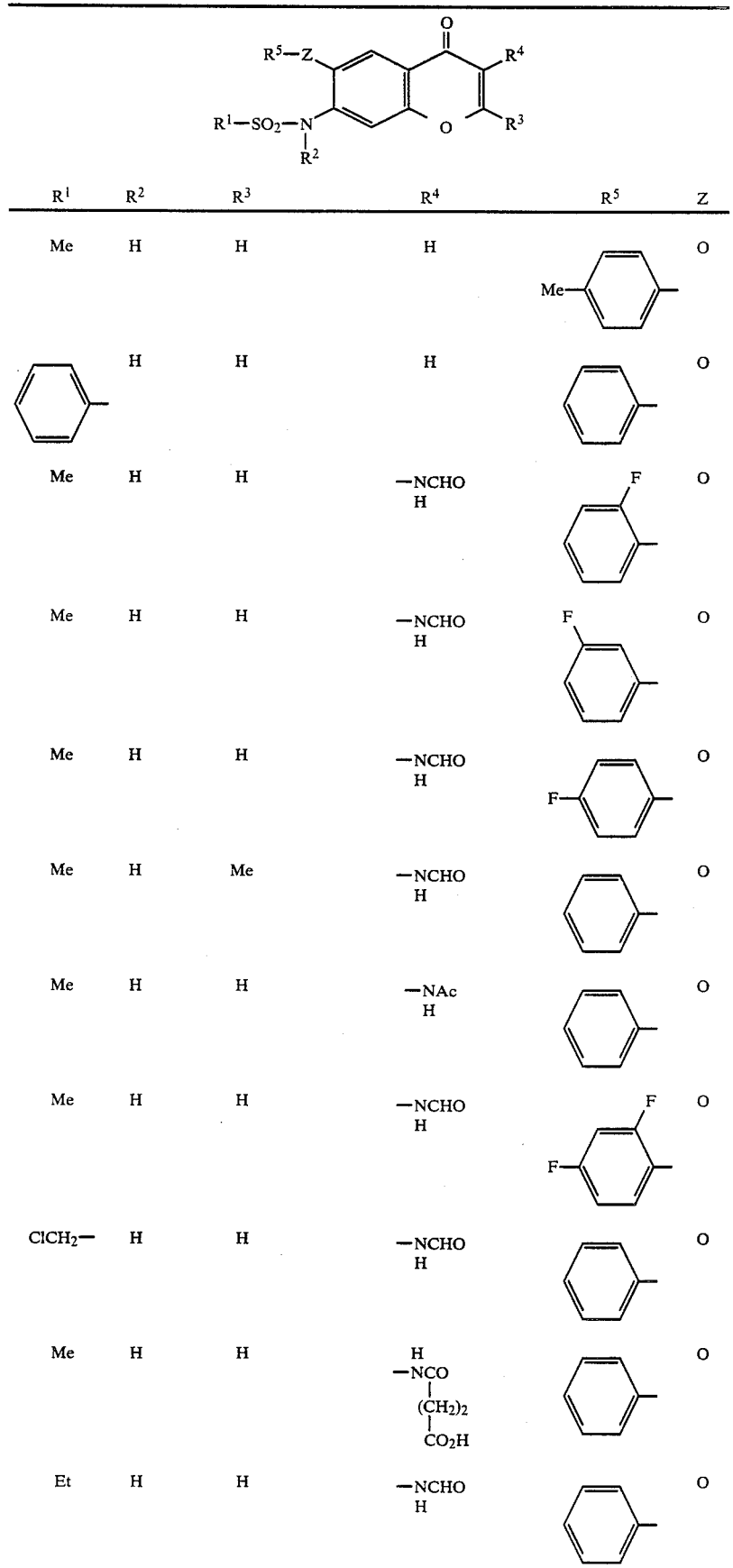
| R¹ | R² | R³ | R⁴ | R⁵ | Z |
|---|---|---|---|---|---|
| Me | H | H | H | 4-Me-phenyl | O |
| phenyl | H | H | H | phenyl | O |
| Me | H | H | —NCHO / H | 2-F-phenyl | O |
| Me | H | H | —NCHO / H | 3-F-phenyl | O |
| Me | H | H | —NCHO / H | 4-F-phenyl | O |
| Me | H | Me | —NCHO / H | phenyl | O |
| Me | H | H | —NAc / H | phenyl | O |
| Me | H | H | —NCHO / H | 2,4-F₂-phenyl | O |
| ClCH₂— | H | H | —NCHO / H | phenyl | O |
| Me | H | H | H / —NCO / (CH₂)₂ / CO₂H | phenyl | O |
| Et | H | H | —NCHO / H | phenyl | O |

TABLE 27-continued

Structure:

R⁵—Z substituent and R¹—SO₂—N(R²)— substituent on a benzene ring bearing a —C(=O)—C(R⁴)=C(R³)—O— fused ring (chromone-like).

| R¹ | R² | R³ | R⁴ | R⁵ | Z |
|---|---|---|---|---|---|
| —CF₃ | H | H | —NCHO<br>H | phenyl | O |
| Me | H | H | —NCHO<br>H | 2-Cl-phenyl | O |
| Me | H | H | —NCHO<br>H | 4-Cl-phenyl | O |
| Me | H | H | —NCHO<br>H | 2-Me-phenyl | O |
| Me | H | H | —NCHO<br>H | 4-Me-phenyl | O |
| Me | H | H | Me<br>—NCHO | 2-F-phenyl | O |
| Me | H | H | Me<br>—NCHO | 4-F-phenyl | O |
| Me | H | H | Et<br>—NCHO | phenyl | O |
| Me | H | H | Me<br>—NAc | phenyl | O |
| Me | H | H | —NCHO<br>  \|<br>  CH₂<br>  \|<br>  CO₂Me | phenyl | O |
| Me | H | H | —NCHO<br>  \|<br>  (CH₂)₃<br>  \|<br>  CO₂Et | phenyl | O |

TABLE 27-continued
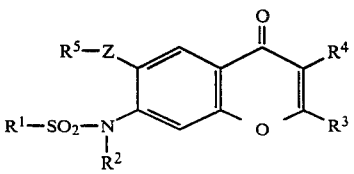
| R¹ | R² | R³ | R⁴ | R⁵ | Z |
|---|---|---|---|---|---|
| Me | H | H | 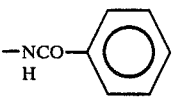 | 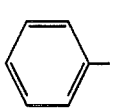 | O |
| Me | H | H |  | 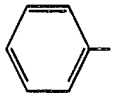 | O |
| Me | H | H |  | 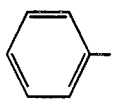 | O |
| Me | H | H |  | 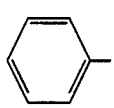 | O |
| Me | H | H | —NHOH |  | O |
| Me | H | H | —CHO | 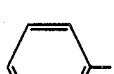 | O |
| Me | H | H | —CHO |  | O |
| Me | H | Me | —CONH₂ | 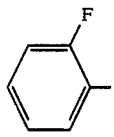 | O |
| Me | H | H | —CONMeH |  | O |
| Me | H | H | 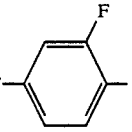 |  | O |
| Me | H | H | 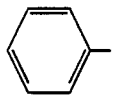 |  | O |

TABLE 27-continued
| R¹ | R² | R³ | R⁴ | R⁵ | Z |
|---|---|---|---|---|---|
| Me | H | H | —CONHOMe | 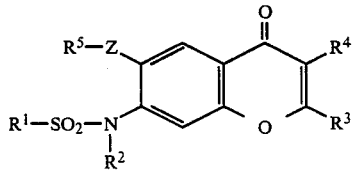 | O |
| Me | H | H | —CON(Me)Me | 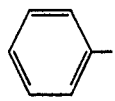 | O |
| Me | H | H | —CON(piperidine) | 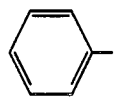 | O |
| Me | H | H | —CONH-(2-pyridyl) | 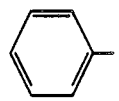 | O |
| Me | H | —CF₃ | H | 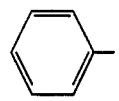 | O |
| Me | H | Et | H | 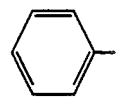 | O |
| Me | H | -i-Pr | H | 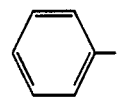 | O |
| Me | H | cyclopropyl | H |  | O |
| Me | H | H | H |  | O |
| Me | H | H | H | 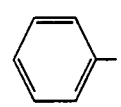 | O |
| Me | H | H | H | 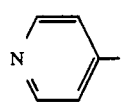 | O |
| Me | H | H | H | 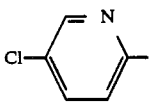 | O |

TABLE 27-continued $R^5-Z$ substituted chromone structure with $R^1-SO_2-N(R^2)-$ group

| $R^1$ | $R^2$ | $R^3$ | $R^4$ | $R^5$ | Z |
|---|---|---|---|---|---|
| Me | H | H | H | 2-CONH$_2$-phenyl | O |
| Me | H | H | H | 2-(i-Pr)-phenyl | O |
| Me | H | H | H | 2,3-diMe-phenyl | O |
| Me | H | H | H | 3-Me-4-F-phenyl | O |
| Me | H | H | H | phenyl | S |
| Me | H | H | —CH$_2$-phenyl | phenyl | O |
| Me | H | H | Et | phenyl | O |
| Me | H | H | phenyl | phenyl | O |
| Me | H | H | -i-Pr | phenyl | O |
| Me | H | H | —NHCHO | 3-Me-phenyl | O |

TABLE 27-continued
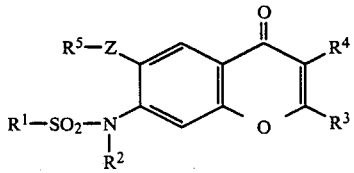
| R¹ | R² | R³ | R⁴ | R⁵ | Z |
|---|---|---|---|---|---|
| Me | H | H | —NCHO<br>H | 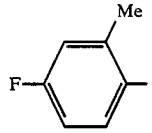 2-Me, 4-F | O |
| Me | H | H | —NCHO<br>H | 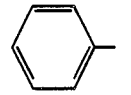 | S |
| Me | H | H | —NAc<br>H | 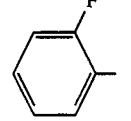 2-F | O |
| Me | H | H | —CN | 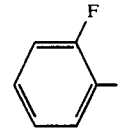 2-F | O |
| Me | H | H | —CN | 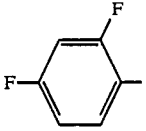 2,4-F | O |
| Me | H | H | H | 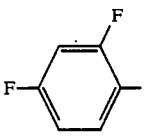 2,4-F | O |
| Me | H | Me | Me | 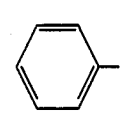 | O |
| Me | H | H | —NCHO<br>H | 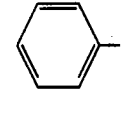 | O |
| Me | H | H | Me<br>—NCHO | 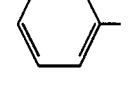 | O |
| Me | H | H | —NCO₂Me<br>H | 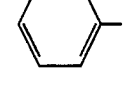 | O |
| Me | H | H | Br | 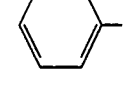 | O |

TABLE 27-continued
[Structure diagram: R⁵—Z— attached to benzene ring with R¹—SO₂—N(R²)— substituent; benzene fused to pyranone ring with C=O, R⁴, R³ substituents]
| R¹ | R² | R³ | R⁴ | R⁵ | Z |
|----|----|----|----|----|----|
| Me | H | H | Cl | 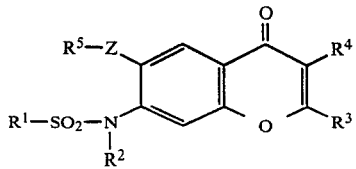 | O |
| Me | H | H | —N(H)CONH₂ | 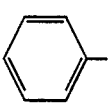 | O |
| Me | H | H | —N(Me)CONH₂ | 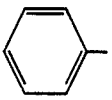 | O |
| Me | Ac | H | 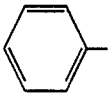 (succinimido, —N(C=O)CH₂CH₂(C=O)) | 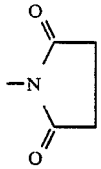 | O |
| Me | H | H | —N(CH₂CO₂H)CHO | 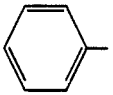 | O |
| Me | H | Br | —N(H)CHO | 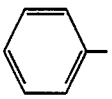 | O |
| Me | H | —OMe | —N(H)CHO | 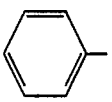 | O |
| Me | H | —OH | —N(H)CHO | 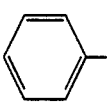 | O |
| Me | H | —CN | —N(H)CHO | 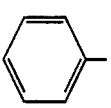 | O |
| Me | H | H | —N(pyrrolyl) | 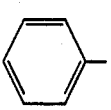 | O |
| Me | H | H | —N(H)Ph | 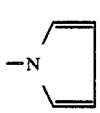 | O |

TABLE 27-continued

| R¹ | R² | R³ | R⁴ | R⁵ | Z |
|---|---|---|---|---|---|
| Me | H | H | —CHO | Ph | O |
| Me | H | H | —COOEt | Ph | O |
| Me | H | H | —COOH | Ph | O |
| Me | Ac | Me | —COOEt | Ph | O |
| Me | H | Me | —COOH | Ph | O |
| Me | H | H | —CONH₂ | Ph | O |
| Me | H | H | Ac | Ph | O |
| Me | H | —COOEt | H | Ph | O |
| Me | H | —COOH | H | Ph | O |
| Me | H | —CONH₂ | H | Ph | O |
| Me | H | —NCOOEt H | H | Ph | O |
| Me | H | —NCOOt-Bu H | H | Ph | O |

TABLE 27-continued
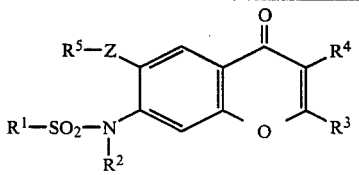
| R¹ | R² | R³ | R⁴ | R⁵ | Z |
|---|---|---|---|---|---|
| Me | H | —NCHO<br>H | H | 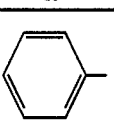 | O |
| Me | H | —NAc<br>H | H | 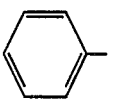 | O |
| Me | H | Me | H | 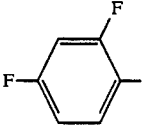 (2,5-F₂) | O |
| Me | H | H | —CH=CH—Ph | 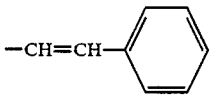 | O |
| Me | H | H | —CH₂NAc<br>H | 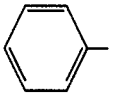 | O |
| Me | H | H | 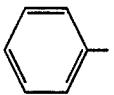 (thiazole) |  | O |
| Me | H | H | —N=CHN(Me)₂ | 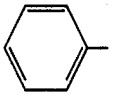 | O |
| Me | H | H | —NSO₂Me<br>H | 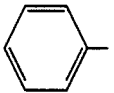 | O |
| Me | H | H | H | 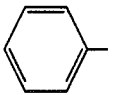 (2-COOH) | O |
| Me | H | H | H | 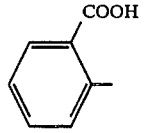 (2-NHAc) | O |
| Me | H | H | H | 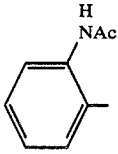 (2-NHCHO) | O |

TABLE 27-continued
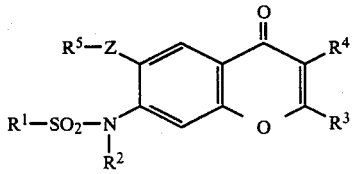
| $R^1$ | $R^2$ | $R^3$ | $R^4$ | $R^5$ | Z |
|---|---|---|---|---|---|
| Me | H | H | H | 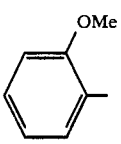 2-OMe-phenyl | O |
| Me | H | H | H | 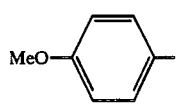 4-MeO-phenyl | O |
| Me | H | H | H | 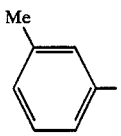 3-Me-phenyl | O |
| Me | H | H | —NCHO<br>H | 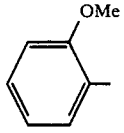 2-OMe-phenyl | O |
| Me | H | H | —CN | 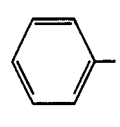 phenyl | O |
| Me | H | H | —CONH$_2$ | 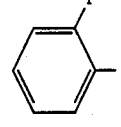 2-F-phenyl | O |
| Me | H | H | —CONH$_2$ | 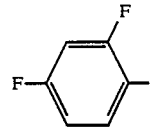 2,4-diF-phenyl | O |
| Me | H | H | —NO$_2$ | 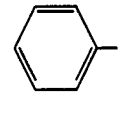 phenyl | O |
| CH$_2$=CH— | H | H | H | 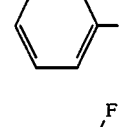 phenyl | O |
| Me | Ac | H | H | 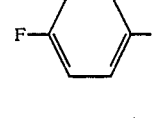 2,4-diF-phenyl | O |

TABLE 27-continued

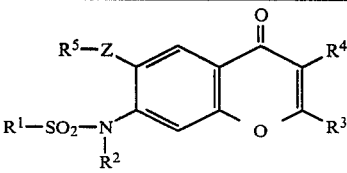

| R¹ | R² | R³ | R⁴ | R⁵ | Z |
|----|----|----|----|----|----|
| Me | Ac | H | —NCHO<br>H | 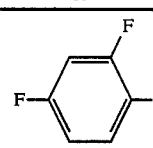 | O |
| Me | Bz | H | H | 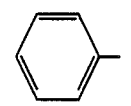 | O |
| Me | Me | H | H | 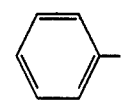 | O |
| Me | H | H | —NH<br>\|<br>CO<br>\|<br>(CH₂)₂<br>\|<br>CH₂Cl | 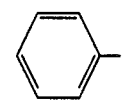 | O |
| Me | H | H | 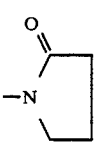 | 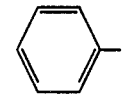 | O |
| Me | H | H | 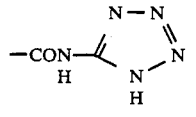 | 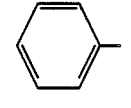 | O |
| Me | H | 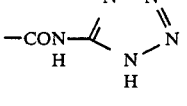 | H | 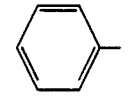 | O |
| Me | H | H | 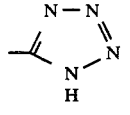 | 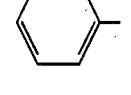 | O |
| Me | H | H | Me |  | O |

EXAMPLE 24

(1) 6.7 g of 4-methoxy-2-methylsulfonylaminophenol was dissolved in 60 ml of methylene chloride. Thereto was added 7.3 g of acetyl chloride. The mixture was cooled to 5° C. Thereto was added 16.5 g of aluminum chloride in portions in 30 minutes at 5°–10° C. The mixture was stirred for 1 hour at 5°–10° C. and for a further 1 hour at 20°–25° C. The reaction mixture was introduced into 200 ml of ice water. The resulting crystal was collected by filtration and then recrystallized from acetonitrile to obtain 3.6 g (yield: 41%) of methyl 5-acetoxy-2-hydroxy-4-methylsulfonylaminophenyl ketone having a melting point of 205°–206.5° C.

IR (KBr) cm⁻¹: 3250, 1760, 1635, 1580, 1495, 1365, 1320, 1190

(2) 2.0 g of methyl 5-acetoxy-2-hydroxy-4-methylsulfonylaminophenyl ketone was suspended in 14 ml of ethyl orthoformate. Thereto was dropwise added 2.0 g of 70% (w/w) perchloric acid in 10 minutes with ice-cooling. The mixture was stirred for 1.5 hours at 20°–25° C. The reaction mixture was mixed with 20 ml of diisopropyl ether. The resulting crystal was collected by filtration and mixed with 20 ml of water. The mixture was refluxed for 5 minutes and then cooled. 50 ml of ethyl acetate was added thereto. The organic layer was separated, washed with water and a saturated aqueous sodium chloride solution in this order, and dried with anhydrous magnesium sulfate. The solvent was removed by distillation under reduced pressure. The residue was dissolved in 14 ml of a 1N aqueous sodium hydroxide solution. The mixture was stirred for 30 minutes at 20°–25° C. The reaction mixture was adjusted to pH 2 with 6N hydrochloric acid. The resulting crystal was collected by filtration and recrystallized from a mixed solvent of N,N-dimethylformamide and water to obtain 1.0 g (yield: 59%) of 6-hydroxy-7-methylsulfonylamino-4H-1-benzopyran-4-one having a melting point of >250° C.

IR (KBr) cm$^{-1}$: 3300, 3250, 1620, 1595, 1460, 1425, 1400, 1330, 1300, 1255

(3) 200 mg of 6-hydroxy-7-methylsulfonylamino-4H-1-benzopyran-4-one was dissolved in 2 ml of N,N-dimethylformamide. Thereto were added 390 mg of bromobenzene, 113 mg of potassium carbonate and 52 mg of a copper powder. The mixture was stirred for 1.5 hours at 150° C. The reaction mixture was introduced into 10 ml of ice water. The mixture was adjusted to pH 2 with 4N hydrochloric acid. Thereto was added 10 ml of ethyl acetate. The organic layer was separated, washed with water and a saturated aqueous sodium chloride solution in this order, and dried with anhydrous magnesium sulfate. The solvent was removed by distillation under reduced pressure. The residue was recrystallized from acetonitrile to obtain 210 mg (yield: 80%) of 7-methylsulfonylamino-6-phenoxy4H-1-benzopyran-4-one. The properties (melting point, IR and NMR) of this compound agreed with those of the compound obtained in Example 1 (3).

EXAMPLE 25

The compounds shown in Table 28 were obtained in the same manner as in Example 24 (3).

The physical properties of these compounds were identical with those of the compounds in Examples 1 to 4.

TABLE 28

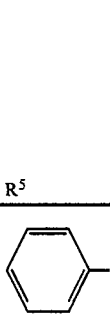

| $R^1$ | $R^2$ | $R^3$ | $R^4$ | $R^5$ | Z |
|---|---|---|---|---|---|
| Me | H | H | —OMe | 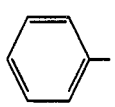 | O |
| Me | H | H | —OH | | O |
| Me | H | H | —SMe | | O |
| Me | H | H | O↑—SMe | 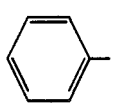 | O |
| Me | H | H | O‖—SMe‖O | 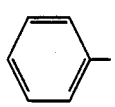 | O |
| Et | H | H | H | 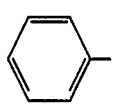 | O |

TABLE 28-continued

Structure: R⁵—Z and R¹—SO₂—N(R²) substituents on benzene ring fused to chromone with R³, R⁴

| R¹ | R² | R³ | R⁴ | R⁵ | Z |
|---|---|---|---|---|---|
| —CF₃ | H | H | H | phenyl | O |
| Me | H | Me | H | phenyl | O |
| Me | H | H | H | 2-pyridyl | O |
| Me | H | phenyl | H | phenyl | O |
| Me | H | H | H | phenyl | HN |
| Me | H | H | H | 3-(CF₃)phenyl | O |
| Me | H | H | H | 3-pyridyl | O |
| Me | H | H | H | 2-F-phenyl | O |
| Me | H | H | H | 3-F-phenyl | O |
| Me | H | H | H | 4-F-phenyl | O |
| Me | H | H | H | 2-Cl-phenyl | O |

TABLE 28-continued
[Structure: R⁵—Z substituted benzene with R¹—SO₂—N(R²)— group, connected to chromone system with R³, R⁴ substituents]
| R¹ | R² | R³ | R⁴ | R⁵ | Z |
|---|---|---|---|---|---|
| Me | H | H | H | 4-Cl-C₆H₄— 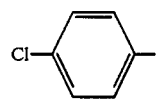 | O |
| Me | H | H | H | 2-Me-C₆H₄— 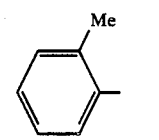 | O |
| Me | H | H | H | 4-Me-C₆H₄— 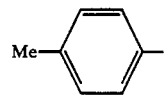 | O |
| C₆H₅— | H | H | H | C₆H₅— 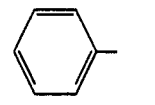 | O |
| Me | H | H | —NH₂ | 2-F-C₆H₄— 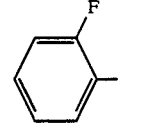 | O |
| Me | H | H | —NH₂ | 3-F-C₆H₄— 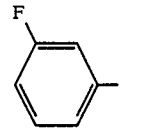 | O |
| Me | H | H | —NH₂ | 4-F-C₆H₄— 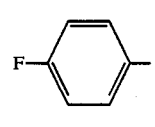 | O |
| Me | H | H | —NH₂ | 2,4-F₂-C₆H₃— 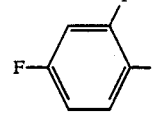 | O |
| Me | H | Me | —NH₂ | C₆H₅— 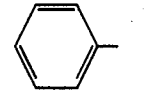 | O |
| ClCH₂— | H | H | —NH₂ | C₆H₅— 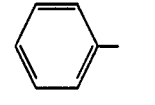 | O |
| Et | H | H | —NH₂ | C₆H₅— 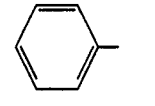 | O |

TABLE 28-continued
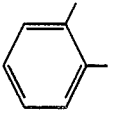
| R¹ | R² | R³ | R⁴ | R⁵ | Z |
|---|---|---|---|---|---|
| Me | H | H | —NH₂ | 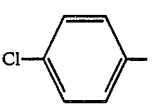 2-Cl-phenyl | O |
| Me | H | H | —NH₂ | 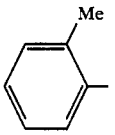 4-Cl-phenyl | O |
| Me | H | H | —NH₂ | 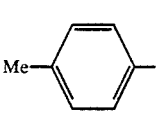 2-Me-phenyl | O |
| Me | H | H | —NH₂ | 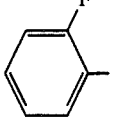 4-Me-phenyl | O |
| Me | H | H | —NCHO H | 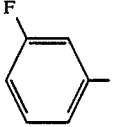 2-F-phenyl | O |
| Me | H | H | —NCHO H | 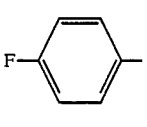 3-F-phenyl | O |
| Me | H | H | —NCHO H | 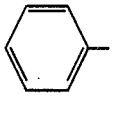 4-F-phenyl | O |
| Me | H | Me | —NCHO H | 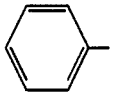 phenyl | O |
| Me | H | H | —NAc H | 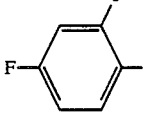 phenyl | O |
| Me | H | H | —NCHO H | 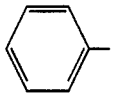 2,4-diF-phenyl | O |
| ClCH₂— | H | H | —NCHO H |  phenyl | O |

TABLE 28-continued
| R¹ | R² | R³ | R⁴ | R⁵ | Z |
|---|---|---|---|---|---|
| Me | H | H | H<br>—N—CO<br>    (CH₂)₂<br>    CO₂H | 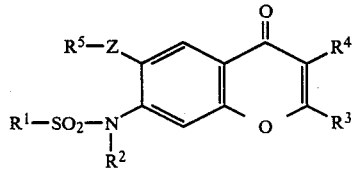 | O |
| Et | H | H | —NCHO<br> H | 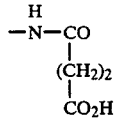 | O |
| —CF₃ | H | H | —NCHO<br> H | 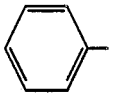 | O |
| Me | H | H | —NCHO<br> H |  (Cl) | O |
| Me | H | H | —NCHO<br> H |  (Cl) | O |
| Me | H | H | —NCHO<br> H |  (Me) | O |
| Me | H | H | —NCHO<br> H |  (Me) | O |
| Me | H | H | Me<br>—NCHO | 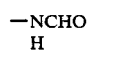 (F) | O |
| Me | H | H | Me<br>—NCHO | 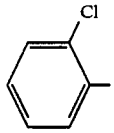 (F) | O |
| Me | H | H | Et<br>—NCHO | 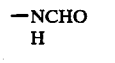 | O |
| Me | H | H | Me<br>—NAc | 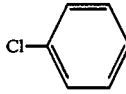 | O |

TABLE 28-continued
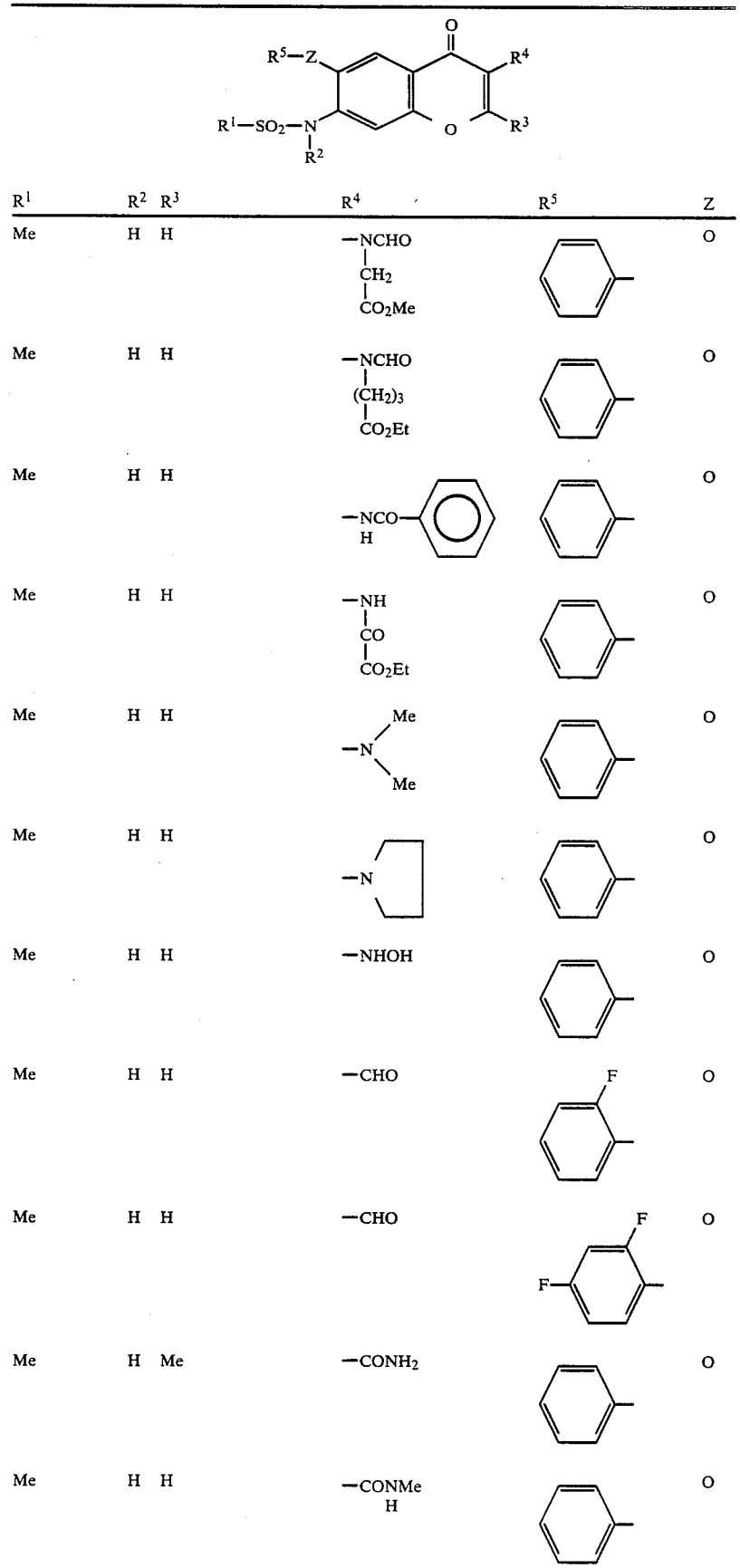
| R¹ | R² | R³ | R⁴ | R⁵ | Z |
|---|---|---|---|---|---|
| Me | H | H | —N(CHO)—CH₂—CO₂Me | Ph | O |
| Me | H | H | —N(CHO)—(CH₂)₃—CO₂Et | Ph | O |
| Me | H | H | —N(H)CO—Ph | Ph | O |
| Me | H | H | —NH—CO—CO₂Et | Ph | O |
| Me | H | H | —N(Me)₂ | Ph | O |
| Me | H | H | —N(piperidine) | Ph | O |
| Me | H | H | —NHOH | Ph | O |
| Me | H | H | —CHO | 2-F-C₆H₄ | O |
| Me | H | H | —CHO | 2,4-F₂-C₆H₃ | O |
| Me | H | Me | —CONH₂ | Ph | O |
| Me | H | H | —CONMeH | Ph | O |

TABLE 28-continued
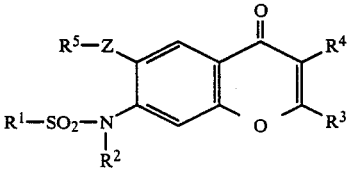
| R¹ | R² | R³ | R⁴ | R⁵ | Z |
|---|---|---|---|---|---|
| Me | H | H | —CONH—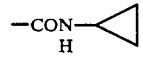 |  | O |
| Me | H | H | —CONH—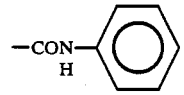 |  | O |
| Me | H | H | —CONHOMe |  | O |
| Me | H | H | —CON(Me)Me |  | O |
| Me | H | H | —CON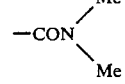 |  | O |
| Me | H | H | —CONH— |  | O |
| Me | H | —CF₃ | H | 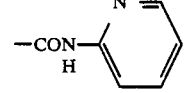 | O |
| Me | H | Et | H |  | O |
| Me | H | -i-Pr | H |  | O |
| Me | H |  | H |  | O |
| Me | H | H | H |  | O |
| Me | H | H | H |  | O |

TABLE 28-continued
| R¹ | R² | R³ | R⁴ | R⁵ | Z |
|---|---|---|---|---|---|
| Me | H | H | H | 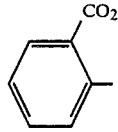 | O |
| Me | H | H | H | 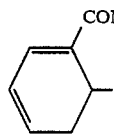 CO₂Me | O |
| Me | H | H | H | 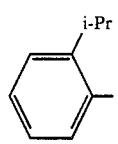 CONH₂ | O |
| Me | H | H | H | 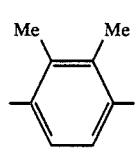 i-Pr | O |
| Me | H | H | H | 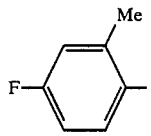 Me Me | O |
| Me | H | H | H | 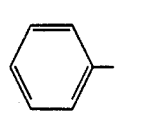 F Me | O |
| Me | H | H | H | 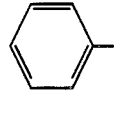 | S |
| Me | H | H | —CH₂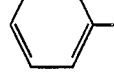 | 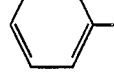 | O |
| Me | H | H | Et | 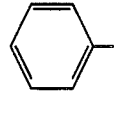 | O |
| Me | H | H | 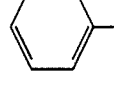 | 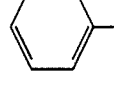 | O |
| Me | H | H | -i-Pr | 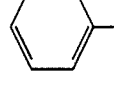 | O |

TABLE 28-continued

[Structure: R⁵—Z on benzene ring fused to chromone with R⁴ (alpha to C=O) and R³ (alpha to O); R¹—SO₂—N(R²) substituent]

| R¹ | R² | R³ | R⁴ | R⁵ | Z |
|---|---|---|---|---|---|
| Me | H | H | —NCHO / H | 3-Me-phenyl | O |
| Me | H | H | —NCHO / H | 4-F-2-Me-phenyl | O |
| Me | H | H | —NCHO / H | phenyl | S |
| Me | H | H | —NAc / H | 2-F-phenyl | O |
| Me | H | H | —C=NOH / H | 2-F-phenyl | O |
| Me | H | H | —C=NOH / H | 2,4-diF-phenyl | O |
| Me | H | H | —CN | 2-F-phenyl | O |
| Me | H | H | —CN | 2,4-diF-phenyl | O |
| Me | H | H | H | 2,4-diF-phenyl | O |
| Me | H | Me | Me | phenyl | O |

TABLE 28-continued

| R¹ | R² | R³ | R⁴ | R⁵ | Z |
|---|---|---|---|---|---|
| Me | Ac | H | H | Ph | O |
| Me | H | H | Me | Ph | O |
| Me | H | H | —NH₂ | Ph | O |
| Me | H | H | —N(H)CHO | Ph | O |
| Me | H | H | —N(Me)CHO | Ph | O |
| Me | H | H | —N(H)Me | Ph | O |
| Me | H | H | —N(H)Et | Ph | O |
| Me | H | H | —N(H)CO₂Me | Ph | O |
| Me | H | H | Br | Ph | O |
| Me | H | H | Cl | Ph | O |
| Me | H | H | —N(H)CONH₂ | Ph | O |
| Me | H | H | —N(Me)CONH₂ | Ph | O |

TABLE 28-continued
| R¹ | R² | R³ | R⁴ | R⁵ | Z |
|---|---|---|---|---|---|
| Me | Ac | H | 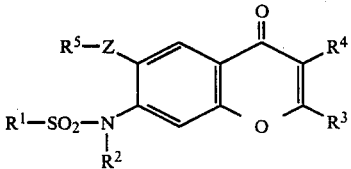 | 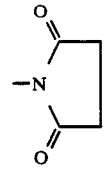 | O |
| Me | H | H | —NCHO<br>CH₂<br>CO₂H | 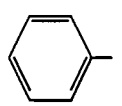 | O |
| Me | H | Br | —NH₂<br>(hydrobromic acid salt form) | 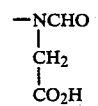 | O |
| Me | H | Br | —NCHO<br>H | 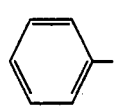 | O |
| Me | H | —OMe | —NCHO<br>H | 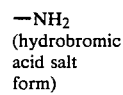 | O |
| Me | H | —OH | —NCHO<br>H | 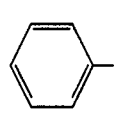 | O |
| Me | H | —CN | —NCHO<br>H |  | O |
| Me | H | H | 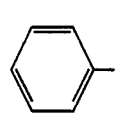 |  | O |
| Me | H | H | 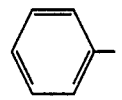 |  | O |
| Me | H | H | —CHO | 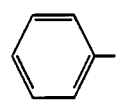 | O |
| Me | H | H | —COOEt |  | O |

TABLE 28-continued
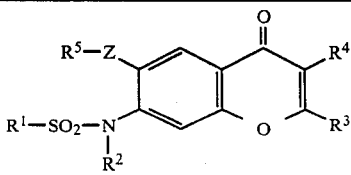
| R¹ | R² | R³ | R⁴ | R⁵ | Z |
|----|----|----|----|----|---|
| Me | H | H | —COOH | 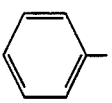 | O |
| Me | Ac | Me | —COOEt | 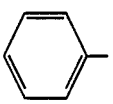 | O |
| Me | H | Me | —COOH | 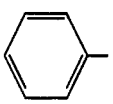 | O |
| Me | H | H | —CONH₂ | 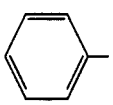 | O |
| Me | H | H | Ac | 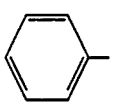 | O |
| Me | H | —COOEt | H | 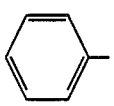 | O |
| Me | H | —COOH | H | 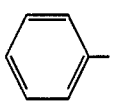 | O |
| Me | H | —CONH₂ | H | 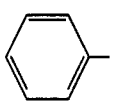 | O |
| Me | H | —CH₂OH | H |  | O |
| Me | H | —NCOOEt H | H | 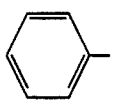 | O |
| Me | H | —NCOOt-Bu H | H | 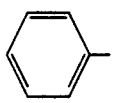 | O |
| Me | H | —NCHO H | H |  | O |

TABLE 28-continued

| $R^1$ | $R^2$ | $R^3$ | $R^4$ | $R^5$ | Z |
|---|---|---|---|---|---|
| Me | H | —NHAc | H | phenyl | O |
| Me | H | —NH$_2$ | H | phenyl | O |
| Me | H | Me | H | 2,4-difluorophenyl | O |
| Me | H | H | —CH$_2$OH | phenyl | O |
| Me | H | H | —CH=CH—phenyl | phenyl | O |
| Me | H | H | —CH(OH)CH$_3$ | phenyl | O |
| Me | H | H | —CH$_2$NHAc | phenyl | O |
| Me | H | H | —CH$_2$NH$_2$ | phenyl | O |
| Me | H | H | thiazolyl | phenyl | O |
| Me | H | —OH | H | phenyl | O |
| Me | H | H | —N=CHN(Me)$_2$ | phenyl | O |

TABLE 28-continued

[Structure: R⁵—Z group and R¹—SO₂—N(R²)— group on benzene ring fused to chromone with R³ and R⁴ substituents]

| R¹ | R² | R³ | R⁴ | R⁵ | Z |
|----|----|----|----|----|---|
| Me | H | H | —NCCHCH₃ with H, ‖, OOH | phenyl | O |
| Me | H | H | —NCCHCH₃ with H, ‖, ONH₂ | phenyl | O |
| Me | H | H | —NSO₂Me, H | phenyl | O |
| Me | H | 2,3-(OMe)₂-phenyl | —OH | phenyl | O |
| Me | H | H | H | 2-COOH-phenyl | O |
| Me | H | H | H | 2-NH₂-phenyl | O |
| Me | H | H | H | 2-NHAc-phenyl | O |
| Me | H | H | H | 2-NHCHO-phenyl | O |
| Me | H | H | H | 2-OMe-phenyl | O |
| Me | H | H | H | 4-OMe-phenyl | O |

TABLE 28-continued

[Structure: R⁵—Z substituted on benzene ring fused to chromone system with R¹—SO₂—N(R²)— group, R³ and R⁴ on pyranone ring]

| R¹ | R² | R³ | R⁴ | R⁵ | Z |
|---|---|---|---|---|---|
| Me | H | H | H | 3-Me-phenyl | O |
| Me | H | H | H | 2-OH-phenyl | O |
| Me | H | H | —NCHO<br>H | 2-OMe-phenyl | O |
| Me | H | H | —C=NOH<br>H | phenyl | O |
| Me | H | H | —CN | phenyl | O |
| Me | H | H | —CONH₂ | 2-F-phenyl | O |
| Me | H | H | —CONH₂ | 2,4-diF-phenyl | O |
| Me | H | —OH | —NO₂ | phenyl | O |
| Me | H | H | —NO₂ | phenyl | O |
| CH₂=CH— | H | H | H | phenyl | O |

TABLE 28-continued

Structure: R⁵—Z and R¹—SO₂—N(R²)— substituents on a 4H-1-benzopyran-4-one with R³ at 2-position and R⁴ at 3-position.

| R¹ | R² | R³ | R⁴ | R⁵ | Z |
|---|---|---|---|---|---|
| Me | Ac | H | H | 2,4-difluorophenyl | O |
| Me | Ac | H | —NCHO / H | 2,4-difluorophenyl | O |
| Me | Bz | H | H | phenyl | O |
| Me | Me | H | H | phenyl | O |
| Me | H | H | —NH—CO—(CH₂)₂—CH₂Cl | phenyl | O |
| Me | H | H | 2-oxopiperidin-1-yl (—N, pyrrolidinone/piperidinone) | phenyl | O |
| Me | H | H | —CONH-(1H-tetrazol-5-yl) | phenyl | O |
| Me | H | —CONH-(1H-tetrazol-5-yl) | H | phenyl | O |
| Me | H | H | (1H-tetrazol-5-yl) | phenyl | O |
| Me | H | —NH₂ | —CONH₂ | phenyl | O |

EXAMPLE 26

(1) 27.6 g of formic acid was added to 30.6 g of acetic anhydride. The mixture was stirred for 1.5 hours at 40°–45° C. The reaction mixture was dropwise added to a solution of 34.6 g of 3-amino-7-methylsulfonylamino-6-phenoxy-4H-1-benzopyran-4-one dissolved in 400 ml of methylene chloride. The mixture was stirred for 1 hour at 20°-25° C. 400 ml of diisopropyl ether was added thereto. The resulting crystal was collected by filtration and recrystallized from acetonitrile to obtain 27.3 g (yield: 73%) of 3-formylamino-7-methylsulfonylamino-6-phenoxy-4H-1-benzopyran-4-one having a melting point of 236°-238° C.

IR (KBr) cm$^{-1}$: 3340, 3260, 1680, 1615, 1600, 1485, 1460, 1340, 1210, 1150

NMR (d$_6$-DMSO) δ: 3.24 (3H, s), 7.09-7.62 (5H, m) 7.35 (1H, s), 7.72 (1H, s), 8.36 (1H, s), 9.28 (1H, s), 9.79 (1H, s), 10.04 (1H, s)

(2) 37.4 g of 3-formylamino-7-methylsulfonylamino-6-phenoxy-4H-1-benzopyran-4-one was dissolved in 370 ml of N,N-dimethylformamide. Thereto was added 8.8 g of sodium hydride (purity: 60%) in 30 minutes, with ice-cooling. After the completion of the addition, the reaction mixture was heated to 45° C. and stirred for 10 minutes. To the mixture being maintained at 25°-30° C. was dropwise added 15.6 g of methyl iodide. Stirring was effected for 30 minutes at the same temperature. The reaction mixture was introduced into 2 liters of water. The mixture was washed with 200 ml of diethyl ether, adjusted to pH 4 with 4N hydrochloric acid, and extracted with two 500-ml portions of ethyl acetate. The extracts (the organic layers) were combined, washed with water and a saturated aqueous sodium chloride solution in this order, and dried with anhydrous magnesium sulfate. The solvent was removed by distillation under reduced pressure and the resulting crystal was recrystallized from acetonitrile to obtain 29.1 g (yield: 75%) of 7-methylsulfonylamino-3-(N-methyl-N-formyl)amino-6-phenoxy-4H-1-benzopyran-4-one having a melting point of 185°-186° C.

IR (KBr) cm$^{-1}$: 1655, 1625, 1610, 1490, 1330, 1275, 1160

NMR (d$_6$-DMSO) δ: 3.04 (3H, s), 3.24 (3H, s), 7.09-7.62 (5H, m), 7.34 (1H, s), 7.76 (1H, s), 8.09 (1H, s), 8.63 (1H, s), 10.07 (1H, s)

The compounds shown in Table 29 were obtained in the same manner.

The physical properties of these compounds were identical with those of the compounds in Example 4.

TABLE 29

| $R^1$ | $R^2$ | $R^3$ | $R^4$ | $R^5$ | Z |
|---|---|---|---|---|---|
| Me | H | H | Me —NCHO | 2-F-phenyl | O |
| Me | H | H | Me —NCHO | 4-F-phenyl | O |

TABLE 29-continued

| $R^1$ | $R^2$ | $R^3$ | $R^4$ | $R^5$ | Z |
|---|---|---|---|---|---|
| Me | H | H | Et —NCHO | phenyl | O |
| Me | H | H | Me —NAc | phenyl | O |
| Me | H | H | —NCHO \| CH$_2$ \| CO$_2$Me | phenyl | O |
| Me | H | H | —NCHO \| (CH$_2$)$_3$ \| CO$_2$Et | phenyl | O |

(3) 3.88 g of 7-methylsulfonylamino-3-(N-formyl-N-methyl)amino-6-phenoxy-4H-1-benzopyran-4-one was suspended in 80 ml of methanol. Thereto was added 40 ml of concentrated hydrochloric acid. The mixture was stirred for 5 hours at 40°-45° C. The solvent was removed by distillation under reduced pressure. The residue was mixed with 300 ml of ethyl acetate and 200 ml of water. The mixture was adjusted to pH 4 with a saturated aqueous sodium hydrogencarbonate solution. The organic layer was separated, washed with a saturated aqueous sodium chloride solution, and dried with anhydrous magnesium sulfate. The solvent was removed by distillation under reduced pressure. The resulting crystal was recrystallized from ethanol to obtain 3.32 g (yield: 92.2%) of 3-methylamino-7-methylsulfonylamino-6-phenoxy-4H-1-benzopyran-4-one having a melting point of 192.5°-193° C.

IR (KBr) cm$^{-1}$: 3350, 3100, 1600, 1585, 1560, 1480, 1415, 1330, 1275, 1210, 1200, 1140

NMR(d$_6$-DMSO) δ: 2.62 (3H, s), 3.20 (3H, s), 4.50-5.20 (1H, br), 7.07-7.50 (5H, m), 7.34 (1H, s), 7.63 (1H, s), 7.67 (1H, s), 9.88 (1H, s)

The following compound was obtained in the same manner:

3-Ethylamino-7-methylsulfonylamino-6-phenoxy-4H-1-benzopyran-4-one.

Melting point: 221°-222° C. (recrystallized from ethanol)

IR (KBr) cm$^{-1}$: 3340, 3100, 1580, 1555, 1480, 1420, 1215, 1140

NMR(CDCl$_3$) δ: 1.29 (3H, t, J=8.0 Hz), 3.00 (2H, t, J=8.0 Hz), 3.11 (3H, s), 6.70-8.00 (7H, m), 7.35 (1H, s), 7.64 (1H, s), 7.70 (1H, s)

EXAMPLE 27

To 70 ml of methylene chloride was added 3.46 g of 3-amino-7-methylsulfonylamino-6-phenoxy-4H-1-benzopyran-4-one. Further, 870 mg of pyridine was added thereto. The mixture was ice-cooled. To this solution was dropwise added a solution of 1.04 g of methyl chlorocarbonate dissolved in 30 ml of methylene chloride, in 10 minutes. The mixture was then stirred for 30 minutes at 20°–25° C. 50 ml of water was added thereto. The resulting mixture was adjusted to pH 4 with 4N hydrochloric acid. The organic layer was separated, washed with water and a saturated aqueous sodium chloride solution in this order, and dried with anhydrous magnesium sulfate. The solvent was removed by distillation under reduced pressure. The resulting crystal was recrystallized from acetonitrile to obtain 2.95 g (yield: 73%) of 3-methoxycarbonylamino-7-methylsulfonylamino-6-phenoxy-4H-1-benzopyran-4-one having a melting point of 233°–235° C.

IR (KBr) cm$^{-1}$: 3390, 3330, 1720, 1620, 1605, 1525, 1455, 1335, 1210, 1160

NMR(d$_6$-DMSO) δ: 3.23 (3H, s), 3.66 (3H, s), 7.09–7.50 (5H, m), 7.34 (1H, s), 7.72 (1H, s), 8.34 (1H, s), 8.74 (1H, s), 10.00 (1H, s)

EXAMPLE 28

(1) In 100 ml of chloroform was dissolved 3.46 g of 3-amino-7-methylsulfonylamino-6-phenoxy-4H-1-benzopyran-4-one. Thereto was dropwise added 1.92 g of bromine at 25°–30° C. The mixture was stirred for 2 hours at the same temperature. The resulting crystal was collected by filtration to obtain 3.60 g (yield: 71.1%) of 3-amino-2-bromo-7-methylsulfonylamino-6-phenoxy-4H-1-benzopyran-4-one hydrobromide having a melting point of 165° C. (decomposed).

IR (KBr) cm$^{-1}$: 1620, 1480, 1450, 1350, 1260, 1200, 1150

(2) 3.06 g of acetic anhydride and 2.76 g of formic acid were mixed and stirred for 1.5 hours at 40°–45° C. to prepare a mixed acid anhydride. Separately, 5.06 g of 3-amino-2-bromo-7-methylsulfonylamino-6-phenoxy-4H-1-benzopyran-4-one hydrobromide was suspended in 100 ml of methylene chloride. To the suspension being ice-cooled was added 1.06 g of triethylamine, and the mixture was stirred for 30 minutes at the same temperature. Thereto was added the above mixed acid anhydride, and the resulting mixture was stirred for 1 hour at 20°–25° C. The solvent was removed by distillation under reduced pressure. The residue was mixed with 200 ml of water. The resulting crystal was collected by filtration and recrystallized from ethyl acetate-diisopropyl ether to obtain 4.15 g (yield: 97.6%) of 2-bromo-3-formylamino-7-methylsulfonylamino-6-phenoxy-4H-1-benzopyran-4-one having a melting point of 237°–238° C.

IR (KBr) cm$^{-1}$: 3170, 1670, 1635, 1610, 1475, 1440, 1325, 1260, 1200, 1150

NMR(d$_6$-DMSO) δ: 3.23 (3H, s), 7.04–7.63 (5H, m), 7.23 (1H, s), 7.73 (1H, s), 8.21 (1H, s), 9.63 (1H, s), 10.17 (1H, s)

(3) 510 mg of metallic sodium was dissolved in 60 ml of methanol. The solution was ice-cooled. Thereto was added 4.25 g of 2-bromo-3-formylamino-7-methylsulfonylamino-6-phenoxy-4H-1-benzopyran-4-one. The mixture was stirred for 2 hours at 0°–5° C. 600 ml of water was added thereto. The resulting mixture was washed with 200 ml of ethyl acetate, adjusted to pH 4 with 4N hydrochloric acid, and extracted with two 300-ml portions of ethyl acetate. The extracts (the organic layers) were combined, washed with a saturated aqueous sodium chloride solution, and dried with anhydrous magnesium sulfate. The solvent was removed by distillation under reduced pressure. The resulting crystal was recrystallized from acetonitrile to obtain 2.87 g (yield: 71%) of 3-formylamino-2-methoxy-7-methylsulfonylamino-6-phenoxy-4H-1-benzopyran-4-one having a melting point of 188° C. (decomposed).

IR (KBr) cm$^{-1}$: 1675, 1610, 1560, 1450, 1320, 1260, 1205, 1140

NMR (d$_6$-DMSO) δ: 3.19 (3H, s), 4.17 (3H, s), 7.04–7.61 (5H, m), 7.29 (1H, s), 7.77 (1H, s), 8.16 (1H, s), 9.07 (1H, s), 10.06 (1H, s)

(4) 2-Bromo-3-formylamino-7-methylsulfonylamino-6-phenoxy-4H-1-benzopyran-4-one was reacted with 1N aqueous sodium hydroxide solution to obtain 3-formylamino-2-hydroxy-7-methylsulfonylamino-6-phenoxy-4H-1-benzopyran-4-one.

Melting point: >250° C. (decomposed) (recrystallized from ethanol)

IR (KBr) cm$^{-1}$: 3350, 3280, 1695, 1670, 1620, 1565, 1370, 1340, 1145

EXAMPLE 29

(1) 3-Amino-7-methylsulfonylamino-6-phenoxy-4H-1-benzopyran-4-one was reacted with N,N-dimethylformamide dimethylacetal to obtain 3-(N,N-dimethylamino)methyleneamino-7-methylsulfonylamino-6-phenoxy-4H-1-benzopyran-4-one.

Melting point: 103°–104° C. (recrystallized from diethyl ether)

IR (KBr) cm$^{-1}$: 1630, 1580, 1470, 1430, 1330, 1190, 1140

(2) 3-Amino-7-methylsulfonylamino-6-phenoxy-4H-1-benzopyran-4-one was reacted with 2-acetoxypropionylchloride. The reaction product was treated with sodium methoxide in methanol to obtain 3-(2-hydroxypropionyl)-amino-7-methylsulfonylamino-6-phenoxy-4H-1-benzopyran-4-one.

Melting point: 219.5°–221.5° C. (recrystallized from ethanol)

IR (KBr) cm$^{-1}$: 3450, 3350, 3250, 1680, 1620, 1590, 1520, 1480, 1460, 1380, 1340, 1260, 1220, 1200, 2260

(3) 3-Amino-7-methylsulfonylamino-6-phenoxy-4H-1-benzopyran-4-one was reacted with N-tert-butoxycarbonylalanine in the presence of dicyclohexylcarbodiimide. The reaction product was treated with trifluoroacetic acid to obtain 3-(2-aminopropionyl)amino-7-methylsulfonylamino-6-phenoxy-4H-1-benzopyran-4-one.

Melting point: 111°–113° C. (recrystallized from ethanol)

IR (KBr) cm$^{-1}$: 3250, 1680, 1620, 1500, 1350, 1210, 1160

(4) 3-Amino-7-methylsulfonylamino-6-phenoxy-4H-1-benzopyran-4-one was reacted with methanesulfonyl chloride to obtain 3,7-bis(methylsulfonylamino)-6-phenoxy-4H-1-benzopyran-4-one.

Melting point: 199°–200° C. (recrystallized from ethanol)

IR (KBr) cm$^{-1}$: 3240, 1640, 1630, 1500, 1340, 1330, 1210, 1150

EXAMPLE 30

6-(2-Methoxyphenoxy)-7-methylsulfonylamino-4H-1-benzopyran-4-one was treated in the same manner as in Example 40 (1), Example 40 (2) and Example 26 to obtain 3-formylamino-6-(2-methoxyphenoxy)-7-methylsulfonylamino-4H-1-benzopyran-4-one. Melting point: 226.5°–227° C. (recrystallized from ethyl acetate)

IR (KBr) cm$^{-1}$: 3280, 1685, 1620, 1600, 1495, 1460, 1335, 1145

EXAMPLE 31

The compounds shown in Table 30 were obtained in the same manner as in Example 26 (1), 27, 28 (2) or 29.

The physical properties of these compounds were identical with those of the compounds in Example 4.

TABLE 30

| $R^1$ | $R^2$ | $R^3$ | $R^4$ | $R^5$ | Z |
|---|---|---|---|---|---|
| Me | H | H | —NCHO<br>H | 2-F-phenyl | O |
| Me | H | H | —NCHO<br>H | 3-F-phenyl | O |
| Me | H | H | —NCHO<br>H | 4-F-phenyl | O |
| Me | H | Me | —NCHO<br>H | phenyl | O |
| Me | H | H | —NAC<br>H | phenyl | O |
| Me | H | H | —NCHO<br>H | 3,4-diF-phenyl | O |
| ClCH$_2$— | H | H | —NCHO<br>H | phenyl | O |
| Me | H | H | H<br>—NCO<br>\|<br>(CH$_2$)$_2$<br>\|<br>CO$_2$H | phenyl | O |

TABLE 30-continued
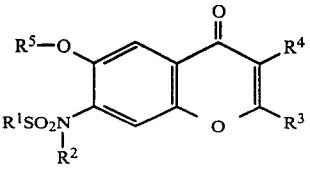
| R¹ | R² | R³ | R⁴ | R⁵ | Z |
|---|---|---|---|---|---|
| Et | H | H | —NCHO<br>H |  | O |
| —CF₃ | H | H | —NCHO<br>H |  | O |
| Me | H | H | —NCHO<br>H | 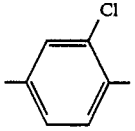 (Cl) | O |
| Me | H | H | —NCHO<br>H |  (Cl) | O |
| Me | H | H | —NCHO<br>H | 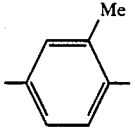 (Me) | O |
| Me | H | H | —NCHO<br>H |  (Me) | O |
| Me | H | H | —NCO<br>H<br> |  | O |
| Me | H | H | —NH<br>CO<br>CO₂Et | | O |
| Me | H | H | —NCHO<br>H | 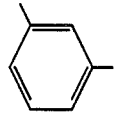 (Me) | O |
| Me | H | H | —NCHO<br>H |  (Me, F) | O |
| Me | H | H | —NCHO<br>H | 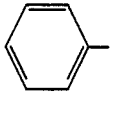 | S |

TABLE 30-continued

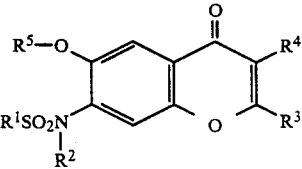

| R¹ | R² | R³ | R⁴ | R⁵ | Z |
|---|---|---|---|---|---|
| Me | H | H | —NAC<br>H | 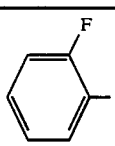 | O |
| Me | H | —CN | —NCHO<br>H | 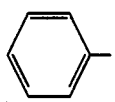 | O |
| Me | Ac | H | —NCHO<br>H | 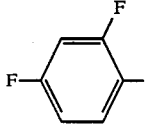 | O |
| Me | H | H | —NH<br>\|<br>CO<br>\|<br>(CH₂)₂<br>\|<br>CH₂Cl | 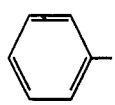 | O |

EXAMPLE 32

3.75 g of 3-carboxy-7-methylsulfonylamino-6-phenoxy-4H-1-benzopyran-4-one was suspended in 75 ml of N,N-dimethylformamide. Thereto was dropwise added 4.6 g of phosphorus oxychloride at −10° to −5° C. The mixture was stirred for 3 hours at the same temperature. The reaction mixture was dropwise added to 40 ml of a concentrated aqueous ammonia solution at 10°–20° C. The mixture was stirred for 30 minutes at the same temperature and then adjusted to pH 4 with 4N hydrochloric acid. The resulting crystal was collected by filtration, washed with water and recrystallized from acetic acid to obtain 2.81 g (yield: 75.1%) of 3-carbamoyl-7-methylsulfonylamino-6-phenoxy-4H-1-benzopyran-4-one having a melting point of >250° C.

IR (KBr) cm⁻¹: 3350, 1705, 1620, 1585, 1485, 1460, 1340, 1160

EXAMPLE 33

3-Carboxy-7-methylsulfonylamino-6-phenoxy-4H-1-benzopyran-4-one was reacted with 5-aminotetrazole in the presence of dicyclohexylcarbodiimide to obtain 7-methylsulfonylamino-6-phenoxy-3-(1,2,3,4-tetrazol-5-yl-aminocarbonyl)-4H-1-benzopyran-4-one.

Melting point: >250° C. (recrystallized from ethanol)

IR (KBr) cm⁻¹: 3350, 1680, 1620, 1580, 1495, 1465, 1310, 1220, 1170

EXAMPLE 34

The compounds shown in Table 31 were obtained in the same manner as in Example 32 or 33.

The physical properties of these compounds were identical with those of the compounds in Example 4.

TABLE 31

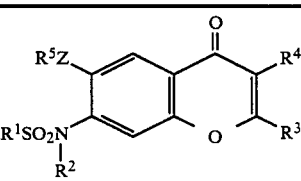

| R¹ | R² | R³ | R⁴ | R⁵ | Z |
|---|---|---|---|---|---|
| Me | H | Me | —CONH₂ | 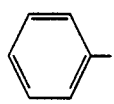 | O |

TABLE 31-continued
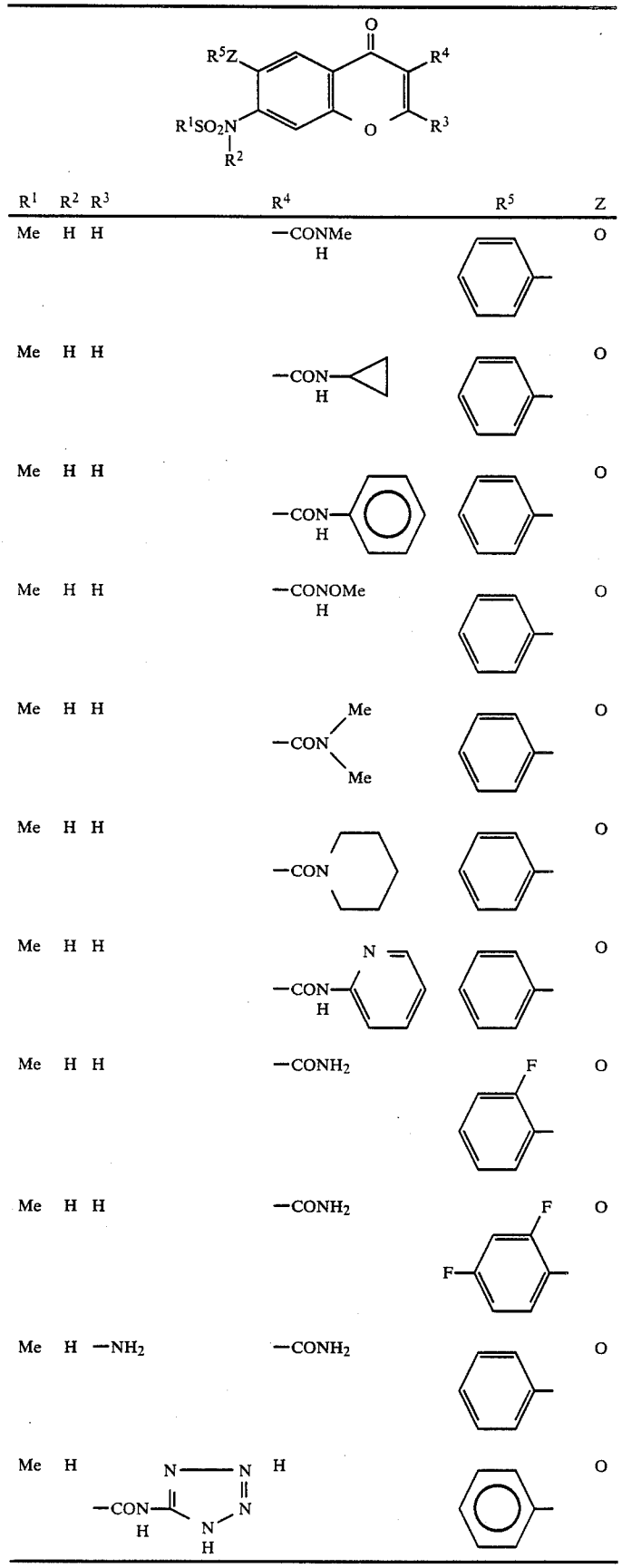
| R¹ | R² | R³ | R⁴ | R⁵ | Z |
|----|----|----|----|----|---|
| Me | H | H | —CONMe, H | phenyl | O |
| Me | H | H | —CONH-cyclopropyl | phenyl | O |
| Me | H | H | —CONH-phenyl | phenyl | O |
| Me | H | H | —CONOMe, H | phenyl | O |
| Me | H | H | —CON(Me)Me | phenyl | O |
| Me | H | H | —CON-piperidinyl | phenyl | O |
| Me | H | H | —CONH-(2-pyridyl) | phenyl | O |
| Me | H | H | —CONH₂ | 2-F-phenyl | O |
| Me | H | H | —CONH₂ | 2,4-F₂-phenyl | O |
| Me | H | —NH₂ | —CONH₂ | phenyl | O |
| Me | H | —CONH-(tetrazol-5-yl) | H | phenyl | O |

EXAMPLE 35

30 ml of concentrated hydrochloric acid and 60 ml of acetic acid were added to 3.74 g of 3-cyano-6-(2-fluorophenoxy)-7-methylsulfonylamino-4H-1-benzopyran-4-one. The mixture was refluxed for 30 minutes. After the completion of the reaction, the solvent was removed by distillation under reduced pressure. The residue was washed with water and then recrystallized from acetic acid to obtain 1.65% (yield: 42.1%) of 3-carbamoyl-6-(2-fluorophenoxy)-7-methylsulfonylamino-4H-1-benzopyran-4-one having a melting point of 249°-251° C.

IR (KBr) cm$^{-1}$: 3330, 3260, 3150, 1695, 1620, 1490, 1455, 1330, 1285, 1155

EXAMPLE 36

3.73 g of 3-cyano-6-(2-fluorophenoxy)-7-methylsulfonylamino-4H-1-benzopyran-4-one was dissolved in 100 ml of formic acid saturated with hydrogen chloride. The mixture was stirred for 24 hours at 25°-30° C. The solvent was removed by distillation under reduced pressure. The residue was mixed with 100 ml of water. The resulting crystal was collected by filtration and recrystallized from acetic acid to obtain 2.54 g (yield: 65%) of 3-carbamoyl-6-(2-fluorophenoxy)-7-methylsulfonylamino-4H-1-benzopyran-4-one. The properties (melting point and IR) of this compound agreed with those of the compound obtained in Example 4.

EXAMPLE 37

The compounds shown in Table 32 were obtained in the same manner as in Example 35 or 36.

The physical properties of these compounds were identical with those of the compounds in Example 4.

TABLE 32

| R$^1$ | R$^2$ | R$^3$ | R$^4$ | R$^5$ | Z |
|---|---|---|---|---|---|
| Me | H | Me | —CONH$_2$ |  | O |
| Me | H | H | —CONH$_2$ | 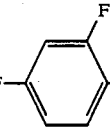 | O |
| Me | H | H | —CONH$_2$ | 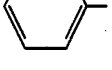 | O |

TABLE 32-continued

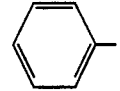

| R$^1$ | R$^2$ | R$^3$ | R$^4$ | R$^5$ | Z |
|---|---|---|---|---|---|
| Me | H | —NH$_2$ | —CONH$_2$ |  | O |

EXAMPLE 38

3.67 g of 6-(2,4-difluorophenoxy)-7-methylsulfonylamino-4H-1-benzopyran-4-one was suspended in 60 ml of acetic acid. Thereto was added 400 mg of 5% palladium-carbon. The mixture was subjected to hydrogenation at 40°-50° C. at atmospheric pressure. After the completion of the reaction, the catalyst was removed by filtration. The filtrate was concentrated. The resulting crystal was recrystallized from ethanol to obtain 3.16 g (yield: 85.6%) of 6-(2,4-difluorophenoxy)-2,3-dihydro-7-methylsulfonylamino-4H-1-benzopyran-4-one having a melting point of 163.5°-165° C.

IR (KBr) cm$^{-1}$: 3220, 1665, 1605, 1575, 1495, 1420

The compounds shown in Table 33 were obtained in the same manner.

TABLE 33

| R$^1$ | R$^3$ | R$^5$ | Melting point (°C.) | IR (KBr) cm$^{-1}$: |
|---|---|---|---|---|
| Me | H | F (2-F phenyl) | 131–132 [Ethanol] | 3240, 1670, 1610, 1490, 1440, 1325, 1255 |
| Me | H | F (3-F phenyl) | 146–147 [Ethanol] | 3100, 1670, 1490, 1325, 1270, 1145 |
| Me | H | F (4-F phenyl) | 167–168 [Ethanol] | 3175, 1670, 1615, 1490, 1440, 1340, 1260 |
| Me | H | phenyl | 143–144 [Methanol] | 3120, 1665, 1610, 1485, 1440, 1320, 1265, 1215, 1160, 1135 |

TABLE 33-continued

[Structure: R⁵—O and R¹—SO₂—NH on a benzene ring with C(=O)—CH₂—CH(R³)—O forming a chromanone]

| R¹ | R³ | R⁵ | Melting point (°C.) | IR (KBr) cm⁻¹: |
|---|---|---|---|---|
| —CF₃ | H | phenyl | 128–130 [IPE] | 3140, 1680, 1610, 1480, 1440, 1370, 1260, 1230, 1210, 1200, 1135 |
| Me | Me | phenyl | 144–145 [Ethanol] | 1665, 1610, 1495, 1440, 1320, 1260, 1215, 1135 |
| Me | H | 2-Cl-phenyl | 130–131 [Ethanol] | 3230, 1680, 1610, 1470, 1440, 1320, 1255, 1160 |
| Me | H | 4-Cl-phenyl | 144–146 [Ethanol] | 3250, 1670, 1610, 1480, 1440, 1340, 1255, 1160 |
| Me | H | 2-Me-phenyl | 157–159 [Toluene] | 3230, 1690, 1610, 1480, 1440, 1340, 1260, 1160 |
| Me | H | 4-Me-phenyl | 120–121 [Toluene] | 3250, 1680, 1615, 1490, 1440, 1340, 1320, 1260, 1135 |

EXAMPLE 39

(1) 6.5 g of 3-(3-methylsulfonylamino-4-phenoxyphenoxy)-3-methylacrylic acid was suspended in 200 ml of ethanol. Thereto was added 1.3 g of 10% palladium-carbon. The mixture was subjected to hydrogenation at 40°–50° C. at atmospheric pressure. After the completion of the reaction, the catalyst was removed by filtration and the solvent was removed by distillation under reduced pressure. The resulting crystal was recrystallized from toluene to obtain 5.69 g (yield: 87%) of 3-(3-methylsulfonylamino-4-phenoxyphenoxy)-3-methylpropionic acid having a melting point of 121°–124° C.

IR (KBr) cm⁻¹: 3350, 1710, 1500, 1335, 1215, 1155

(2) 100 g of polyphosphoric acid was added to 5.69 g of 3-(3-methylsulfonylamino-4-phenoxyphenoxy)-3-methylpropionic acid. The mixture was stirred for 1 hour at 65° C. The reaction mixture was introduced into 400 ml of ice water, and 150 ml of ethyl acetate was added thereto. The organic layer was separated and the solvent was removed by distillation under reduced pressure. The residue was dissolved in 150 ml of 1N aqueous sodium hydroxide solution. The solution was washed with diethyl ether and adjusted to pH 4 with 4N hydrochloric acid. 150 ml of ethyl acetate was added thereto. The organic layer was separated, washed with water and a saturated aqueous sodium chloride solution in this order, and dried with anhydrous magnesium sulfate. The solvent was removed by distillation under reduced pressure. The residue was purified by a column chromatography (eluant: a 25:1 mixture of toluene and ethyl acetate) and recrystallized from ethanol to obtain 2.16 g (yield: 40%) of 2,3-dihydro-2-methyl-7-methylsulfonylamino-6-phenoxy-4H-1-benzopyran-4-one.

The properties (melting point and IR) of this compound agreed with those of the compound obtained in Example 22.

Example 40

(1) In 300 ml of chloroform was dissolved 33.3 g of 2,3-dihydro-7-methylsulfonylamino-6-phenoxy-4H-1-benzopyran-4-one. To this solution being maintained at 25°–30° C. was dropwise added 16.3 g of bromine in 30 minutes. After the completion of the dropwise addition, the mixture was stirred for 30 minutes at 25°–30° C. 100 ml of water was added thereto. The organic layer was separated, washed with a 5% aqueous sodium thiosulfate solution, water and a saturated aqueous sodium chloride solution in this order, and dried with anhydrous magnesium sulfate. The solvent was removed by distillation under reduced pressure to obtain 40.1 g (yield: 97.3%) of 3-bromo-2,3-dihydro-7-methylsulfonylamino-6-phenoxy-4H-1-benzopyran-4-one.

Melting point: 137°–140° C. (recrystallized from toluene)

IR (KBr) cm⁻¹: 3250, 1680, 1610, 1485, 1325, 1260, 1205

NMR(CDCl₃)δ: 3.14 (3H, s), 4.54–4.70 (3H, m), 6.91–7.38 (8H, m)

(2) In 280 ml of N,N-dimethylformamide was dissolved 40.1 g of 3-bromo-2,3-dihydro-7-methylsulfonylamino-6-phenoxy-4H-1-benzopyran-4-one. Thereto was added 13.9 g of sodium azide. The mixture was stirred for 1 hour at 70°–75° C. The reaction mixture was introduced into a mixed solvent consisting of 1.5 liters of water and 300 ml of ethyl acetate. The mixture was adjusted to pH 0.1 with conc. hydrochloric acid. The aqueous layer was separated, washed with 200 ml of ethyl acetate, adjusted to pH 4.0 with a 10% aqueous sodium hydroxide solution, and extracted with two 500-ml portions of ethyl acetate. The extracts (the organic layers) were combined, washed with water and a saturated aqueous sodium chloride solution in this order, and dried with anhydrous magnesium sulfate. The solvent was removed by distillation under reduced pressure. The crystal was recrystallized from ethanol to obtain 2.84 g (yield: 82.1%) of 3-amino-7-methylsulfonylamino-6-phenoxy-4H-1-benzopyran-4-one having a melting point of 162°–163° C.

IR (KBr) cm⁻¹: 3440, 3330, 3180, 1600, 1580, 1550, 1480, 1465, 1330, 1205, 1150

NMR(d₆-DMSO)δ: 3.19 (3H, s), 5.50–7.00 (2H, br), 7.04–7.49 (5H, m), 7.35 (1H, s), 7.62 (1H, s), 7.94 (1H, s)

EXAMPLE 41

The compounds shown in Table 34 were obtained in the same manner as in Example 40 (1) and (2).

The physical properties of the compounds were identical with those of the compounds in Example 4.

TABLE 34

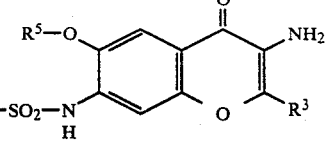

| R¹ | R³ | R⁵ |
|---|---|---|
| Me | H | 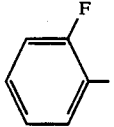 |
| Me | H | 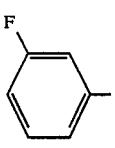 |
| Me | H | 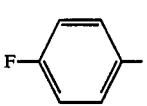 |
| Me | H | 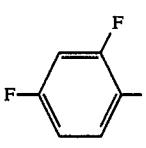 |
| Me | Me | 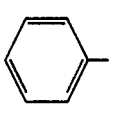 |
| ClCH₂— | H | 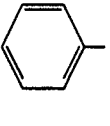 |
| Et | H | 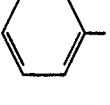 |
| Me | H | 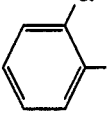 |
| Me | H | 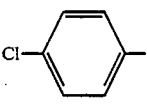 |

TABLE 34-continued

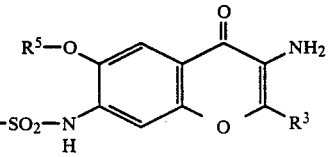

| R¹ | R³ | R⁵ |
|---|---|---|
| Me | H | 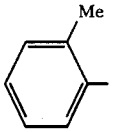 |
| Me | H | 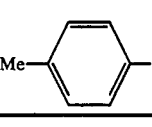 |

EXAMPLE 42

(1) In 50 ml of chloroform was dissolved 3.33 g of 2,3-dihydro-7-methylsulfonylamino-6-phenoxy-4H-1-benzopyran-4-one. Thereto was dropwise added 3.36 g of bromine at 35°–40° C. in 20 minutes. The mixture was stirred for 30 minutes at the same temperature and then introduced into 50 ml of water. The organic layer was separated, washed with a 5% aqueous sodium thiosulfate solution, water and a saturated aqueous sodium chloride solution in this order, and dried with anhydrous magnesium sulfate. The solvent was removed by distillation under reduced pressure to obtain 4.81 g (yield: 98%) of 3,3-dibromo-2,3-dihydro-7-methylsulfonylamino-6-phenoxy-4H-1-benzopyran-4-one.

Melting point: 169°–170° C. (recrystallized from acetonitrile)

IR (KBr) cm⁻¹: 3330, 1690, 1610, 1485, 1325, 1255

NMR(CDCl₃)δ: 3.15 (3H, s), 4.70 (2H, s), 6.91–7.57 (6H, m), 7.32 (1H, s), 7.40 (1H, s)

(2) In 20 ml of pyridine was dissolved 4.81 g of 3,3-dibromo-2,3-dihydro-7-methylsulfonylamino-6phenoxy-4H-1-benzopyran-4-one. The solution was refluxed for 20 minutes. The reaction mixture was introduced into 200 ml of water. The mixture was adjusted to pH 4 with concentrated hydrochloric acid and then extracted with two 100-ml portions of ethyl acetate. The extracts (the organic layers) were combined, washed with water and a saturated aqueous sodium chloride solution in this order, and dried with anhydrous magnesium sulfate. The solvent was removed by distillation under reduced pressure. The resulting crystal was recrystallized from acetonitrile to obtain 3.30 g (yield: 82%) of 3-bromo-7-methylsulfonylamino-6-phenoxy-4H-1-benzopyran-4-one having a melting point of 215°–216° C.

IR (KBr) cm⁻¹: 3100, 3080, 1635, 1620, 1485, 1455, 1335, 1155

NMR(d₆-DMSO)δ: 3.23 (3H, s), 7.06–7.66 (5H, m), 7.30 (1H, s), 7.72 (1H, s), 8.81 (1H, s), 10.07 (1H, s)

The following compound was obtained in the same manner as in Example 42 (1) and (2):

3-Chloro-7-methylsulfonylamino-6-phenoxy-4H-1-benzopyran-4-one

Melting point: 200°–201° C. (recrystallized from ethyl acetate-diisopropyl ether)

IR (KBr) cm$^{-1}$: 3220, 3050, 1645, 1600, 1560, 1480, 1450

(3) 50 ml of a 25% aqueous methylamine solution was ice-cooled. Thereto was added 4.1 g of 3-bromo-7-methylsulfonylamino-6-phenoxy-4H-1-benzopyran-4-one. The mixture was stirred for 2 hours at 0°–5° C. 100 ml of water was added thereto. The mixture was adjusted to pH 4 with 4N hydrochloric acid and then extracted with 100 ml of ethyl acetate. The extract was washed with a saturated aqueous sodium chloride solution and dried with anhydrous magnesium sulfate. The solvent was removed by distillation under reduced pressure. The residue was purified by a column chromatography (eluant: a 5:1 mixture of toluene and ethyl acetate) and then recrystallized from ethanol to obtain 400 mg (yield: 11.1%) of 3-methylamino-7-methylsulfonylamino-6-phenoxy-4H-1-benzopyran-4-one.

The properties (melting point, IR and NMR) of this compound agreed with those of the compound obtained in Example 4.

The compounds shown in Table 35 were obtained in the same manner.

The physical properties of these compounds were identical with those of the compounds in Example 4.

TABLE 35

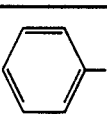

| R$^5$ | R$^6$ | R$^7$ |
|---|---|---|
| 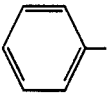 | Me | Me |
| 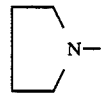 | \multicolumn{2}{c}{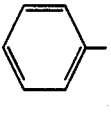} |
| 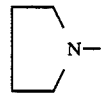 | H | OH |
|  | H | Et |

(4) 340 mg of acetic anhydride and 310 mg of formic acid were mixed. The mixture was stirred for 1.5 hours at 40°–45° C. Thereto was added 10 ml of methylene chloride. There was further added 400 mg of 7-methylsulfonylamino-3-methylamino-6-phenoxy-4H-1-benzopyran-4-one. The resulting mixture was stirred for 1 hour at 25°–30° C. 10 ml of diisopropyl ether was added thereto. The resulting crystal was collected by filtration and then recrystallized from acetonitrile to obtain 330 mg (yield: 76.7%) of 7-methylsulfonylamino-3-(N-formyl-N-methylamino)-6-phenoxy-4H-1-benzopyran-4-one.

The properties (melting point, IR and NMR) of this compound agreed with those of the compound obtained in Example 4.

EXAMPLE 43

500 mg of 3-amino-7-methylsulfonylamino-6-phenoxy-4H-1-benzopyran-4-one was dissolved in 20 ml of acetic acid and 10 ml of water. The solution was heated to 35° C. Thereto was dropwise added a solution of 190 mg of sodium cyanate dissolved in 5 ml of water, in 5 minutes. The mixture was stirred for 30 minutes at the same temperature. 20 ml of water was added thereto. The resulting crystal was collected by filtration and recrystallized from acetic acid to obtain 350 mg (yield: 62.3%) of 7-methylsulfonylamino-6-phenoxy-3-ureido-4H-1-benzopyran-4-one having a melting point of >250° C.

IR (KBr) cm$^{-1}$: 3495, 3340, 3300, 1680, 1620, 1590

NMR(d$_6$-DMSO)δ: 3.21 (3H, s), 6.34 (2H, s), 7.02–7.55 (6H, m), 7.69 (1H, s), 8.02 (1H, s), 9.09 (1H, s), 9.90 (1H, bs)

EXAMPLE 44

In 10 ml of methylene chloride was dissolved 500 mg of 3-methylamino-7-methylsulfonylamino-6-phenoxy-4H-1-benzopyran-4-one. Thereto was dropwise added 220 mg of chlorosulfonyl isocyanate at 0°–5° C. The mixture was stirred for 10 minutes at the same temperature. 20 ml of water was added thereto. The organic layer was separated. The solvent was removed by distillation under reduced pressure. The residue was mixed with 5 ml of methanol and 5 ml of 2N hydrochloric acid. The mixture was stirred for 1 hour at 20°–25° C. To the reaction mixture were added 20 ml of methylene chloride and 20 ml of water. The organic layer were separated, washed with water and a saturated aqueous sodium chloride solution in this order, and dried with anhydrous magnesium sulfate. The solvent was removed by distillation under reduced pressure. The residue was purified by a column chromatography (eluant: a 1:1 mixture of toluene and ethyl acetate) to obtain 220 mg (yield: 35.1%) of 7-methylsulfonylamino-3-(1-methylureido)-6-phenoxy-4H-1-benzopyran-4-one.

Melting point: 145°–145.5° C. (recrystallized from ethanol)

IR (KBr) cm$^{-1}$: 3450, 3350, 1640, 1620, 1480, 1450

NMR(d$_6$-DMSO)δ: 2.95 (3H, s), 3.20 (3H, s), 5.85 (2H, bs), 7.06–7.50 (6H, m), 7.70 (1H, s), 8.43 (1H, s), 10.00 (1H, bs)

EXAMPLE 45

4 ml of acetic anhydride and 200 mg of sodium acetate were added to 400 mg of 3-[N-(3-carboxypropionyl)-amino]-7-methylsulfonylamino-6-phenoxy-4H-1-benzopyran-4-one. The mixture was stirred for 30 minutes at 90°–100° C. and then cooled to room temperature. 30 ml of water and 30 ml of ethyl acetate were added thereto. The organic layer was separated, washed with water and a saturated aqueous sodium chloride solution in this order, and dried with anhydrous magnesium sulfate. The solvent was removed by distillation under reduced pressure. The residue was recrystallized from ethyl acetate to obtain 300 mg (yield: 79%) of 7-(N-acetyl-N-methylsulfonylamino)-6-phenoxy-3-(1-succinimino)-4H-1-benzopyran-4-one having a melting point of 220°–221° C.

IR (KBr) cm$^{-1}$: 3050, 1780, 1720, 1650, 1620, 1575

NMR(d$_6$-DMSO)δ: 2.13 (3H, s), 2.88 (4H, s), 3.59 (3H, s), 7.17–7.56 (6H, m), 8.27 (1H, s), 8.63 (1H, s)

EXAMPLE 46

In 45 ml of a 1N aqueous sodium hydroxide solution was dissolved 4.46 g of 7-methylsulfonylamino- 3-(N-formyl-N-methoxycarbonylmethylamino)-6-phenoxy-4H-1-benzopyran-4-one. The solution was stirred for 1.5 hours at 25°–30° C. The solution was then adjusted to pH 3 with 4N hydrochloric acid and extracted with two 50-ml portions of ethyl acetate. The extracts (the organic layers) were combined, washed with water and a saturated aqueous sodium chloride solution in this order, and dried with anhydrous magnesium sulfate. The solvent was removed by distillation under reduced pressure. The residue was mixed with diethyl ether. The resulting crystal was collected by filtration to obtain 3.57 g (yield: 82.6%) of 7-methylsulfonylamino-3-(N-carboxymethyl-N-formylamino)-6-phenoxy-4H-1-benzopyran-4-one having a melting point of 98°–100° C.

IR (KBr) cm$^{-1}$: 3220, 1730, 1665, 1610, 1490, 1445, 1335, 1205, 1160

NMR(d$_6$-DMSO)δ: 3.22 (3H, s), 4.25 (2H, s), 7.07–7.65 (5H, m), 7.32 (1H, s), 7.76 (1H, s), 8.19 (1H, s), 8.56 (1H, s), 10.00 (1H, bs)

EXAMPLE 47

4.25 g of 2-bromo-3-formylamino-7-methylsulfonylamino-6-phenoxy-4H-1-benzopyran-4-one was dissolved in 50 ml of N,N-dimethylformamide. 1.97 g of cuprous cyanide was added thereto, and the resulting mixture was stirred for 2 hours at 85°–90° C. The reaction mixture was introduced into 300 ml of water, adjusted to pH 4 with 4N hydrochloric acid, and extracted with two 200-ml portions of ethyl acetate. The extracts (the organic layers) were combined, washed with water and a saturated aqueous sodium chloride solution in this order, and dried with anhydrous sodium sulfate. The solvent was removed by distillation under reduced pressure. The resulting residue was recrystallized from acetonitrile to obtain 2.05 g (yield: 55.3%) of 2-cyano-3-formylamino-7-methylsulfonylamino-6-phenoxy-4H-1-benzopyran-4-one having a melting point of 229°–230° C.

IR (KBr) cm$^{-1}$: 3260, 2225, 1715, 1610, 1485, 1460, 1330, 1215, 1150

NMR(d$_6$-DMSO)δ: 3.28 (3H, s), 7.07–7.62 (5H, m), 7.27 (1H, s), 7.76 (1H, s), 8.37 (1H, d, J=3.0 Hz), 10.22 (1H, d, J=3.0 Hz), 10.22 (1H, s)

EXAMPLE 48

In 5 ml of acetic acid were dissolved 500 mg of 3-amino-7-methylsulfonylamino-6-phenoxy-4H-1-benzopyran-4-one and 250 mg of 2,5-dimethoxytetrahydrofuran. The mixture was stirred for 30 minutes at 70°–80° C. and then cooled to room temperature. 50 ml of water was added thereto. The resulting crystal was collected by filtration and recrystallized from ethyl acetate-diisopropyl ether to obtain 250 mg (yield: 43.7%) of 7-methylsulfonylamino-6-phenoxy-3-(1-pyrrolyl)-4H-1-benzopyran-4-one having a melting point of 238.5°–240° C.

IR (KBr) cm$^{-1}$: 1640, 1615, 1575, 1475, 1440, 1425, 1410

EXAMPLE 49

3.46 g of 3-amino-7-methylsulfonylamino-6-phenoxy-4H-1-benzopyran-4-one was dissolved in 35 ml of N,N-dimethylformamide. Thereto were added 7 ml of bromobenzene, 1.66 g of potassium iodide, 1.38 g of potassium carbonate and 0.64 g of a copper powder. The mixture was refluxed for 6 hours. The reaction mixture was introduced into a mixture consisting of 300 ml of water and 200 ml of ethyl acetate. The insolubles were removed by filtration, and the filtrate was adjusted to pH 4 with 4N hydrochloric acid. The organic layer was separated, washed with water and a saturated aqueous sodium chloride solution in this order, and dried with anhydrous magnesium sulfate. The solvent was removed by distillation under reduced pressure. The residue was purified by a column chromatography (eluant: a 20:1 mixture of toluene and ethyl acetate) and then recrystallized from acetonitrile to obtain 430 mg (yield: 10.2%) of 7-methylsulfonylamino-3-phenylamino-6-phenoxy-4H-1-benzopyran-4-one having a melting point of 212°–213° C.

IR (KBr) cm$^{-1}$: 3240, 1645, 1620, 1580, 1485, 1455, 1340, 1265, 1160

NMR(d$_6$-DMSO)δ: 3.22 (3H, s), 6.92–7.59 (12H, m), 7.76 (1H, s), 8.58 (1H, s), 10.01 (1H, bs)

EXAMPLE 50

(1) 3.5 g of 2-ethoxycarbonyl-7-methylsulfonylamino-6-phenoxy-4H-1-benzopyran-4-one was suspended in 30 ml of acetic acid. Thereto was added 20 ml of concentrated hydrochloric acid. The mixture was refluxed for 1 hour. To the reaction mixture was added 100 ml of water. The resulting crystal was collected by filtration and then recrystallized from ethanol to obtain 3.0 g (yield: 91%) of 2-carboxy-7-methylsulfonylamino-6-phenoxy-4H-1-benzopyran-4-one having a melting point of >250° C.

IR (KBr) cm$^{-1}$: 3245, 1730, 1625, 1590, 1460, 1335, 1220, 1160

(2) 3.0 g of 2-carboxy-7-methylsulfonylamino-6-phenoxy-4H-1-benzopyran-4-one was suspended in 30 ml of methylene chloride. Thereto were added 3.8 g of thionyl chloride and 0.1 ml of N,N-dimethylformamide. The mixture was refluxed for 1.5 hours. After the completion of the reaction, the solvent was removed by distillation under reduced pressure to obtain 3.1 g (yield: 98.4%) of 7-methylsulfonylamino-6-phenoxy-4H-1-benzopyran-4-one-2-carboxylic acid chloride.

IR (neat) cm$^{-1}$: 1760

(3) 7-Methylsulfonylamino-6-phenoxy-4H-1-benzopyran-4-one-2-carboxylic acid chloride was reacted with ammonia to obtain 2-carbamoyl-7-methylsulfonylamino-6-phenoxy-4H-1-benzopyran-4-one.

Melting point: >250° C. (recrystallised from methanol)

IR (KBr) cm$^{-1}$: 3425, 1700, 1645, 1625, 1450, 1325, 1210, 1135

(4) 7-Methylsulfonylamino-6-phenoxy-4H-1-benzopyran-4-one-2-carboxylic acid chloride was reduced by sodium boron hydride to obtain 2-hydroxymethyl-7-methylsulfonylamino-6-phenoxy-4H-1-benzopyran-4-one.

Melting point: 210°-215° C. (decomposed) (recrystallized from ethyl acetate)

IR (KBr) cm$^{-1}$: 3375, 3240, 1630, 1585, 1480, 1455, 1395, 1370, 1325, 1260, 1210

(5) 3.1 g of 7-methylsulfonylamino-6-phenoxy-4H-1-benzopyran-4-one-2-carboxylic acid chloride was dissolved in 80 ml of anhydrous tetrahydrofuran. This solution was dropwise added to 10 ml of an aqueous solution containing 1.26 g of sodium azide in 10 minutes at 5°-10° C. The mixture was stirred for 1.5 hours at 10°-20° C. The resulting crystal was collected by filtration to obtain 1.45 g (yield: 46%) of 7-methylsulfonylamino-6-phenoxy-4H-1-benzopyran-4-one-2-carboxylic acid azide having a melting point of 146°-149° C. (decomposed).

IR (KBr) cm$^{-1}$: 3200, 2125, 1700, 1640, 1610, 1480, 1440, 1320, 1200, 1130

(6) 7-Methylsulfonylamino-6-phenoxy-4H-1-benzopyran-4-one-2-carboxylic acid azide was reacted with ethanol with heating to obtain 2-ethoxycarbonylamino-7-methylsulfonylamino-6-phenoxy-4H-1-benzopyran-4-one.

Melting point: 207°-209° C. (recrystallized from ethanol)

IR (KBr) cm$^{-1}$: 3230, 1740, 1620, 1535, 1480, 1450, 1325, 1210, 1140

(7) 7-Methylsulfonylamino-6-phenoxy-4H-1-benzopyran-4-one-2-carboxylic acid azide was reacted with tertbutanol with heating to obtain 2-tert-butoxycarbonylamino-7-methylsulfonylamino-6-phenoxy-4H-1-benzopyran-4-one.

Melting point: 147°-150° C. (recrystallized from benzene)

IR (KBr) cm$^{-1}$: 3250, 1745, 1620, 1525, 1490, 1450, 1360, 1330, 1230, 1140

(8) 7-Methylsulfonylamino-6-phenoxy-4H-1-benzopyran-4-one-2-carboxylic acid azide was reacted with formic acid with heating to obtain 2-formylamino-7-methylsulfonylamino-6-phenoxy-4H-1-benzopyran-4-one.

Melting point: 214°-216° C. (recrystallized from acetonitrile)

IR (KBr) cm$^{-1}$: 3225, 3120, 1710, 1625, 1610, 1555, 1450, 1215, 1150, 1145

(9) 7-Methylsulfonylamino-6-phenoxy-4H-1-benzopyran-4-one-2-carboxylic acid azide was reacted with acetic acid with heating to obtain 2-acetylamino-7-methylsulfonylamino-6-phenoxy-4H-1-benzopyran-4-one.

Melting point: 236°-238° C. (recrystallized from ethanol)

IR (KBr) cm$^{-1}$: 3170, 1700, 1620, 1600, 1525, 1450, 1350, 1250, 1240, 1220, 1145

(10) 2-tert-Butoxycarbonylamino-7-methylsulfonylamino-6-phenoxy-4H-1-benzopyran-4-one was reacted with trifluoroacetic acid to obtain 2-amino-7-methylsulfonylamino-6-phenoxy-4H-1-benzopyran-4-one.

Melting point: 223°-225° C. (recrystallized from ethanol)

IR (KBr) cm$^{-1}$: 3225, 1660, 1615, 1550, 1480, 1200, 1145

EXAMPLE 51

(1) 3-Formyl-7-methylsulfonylamino-6-phenoxy-4H-1-benzopyran-4-one was reduced by sodium boron hydride to obtain 3-hydroxymethyl-7-methylsulfonylamino-6-phenoxy-4H-1-benzopyran-4-one.

Melting point: 165°-166.5° C. (recrystallized from ethyl acetate-diethyl ether)

IR (KBr) cm$^{-1}$: 3450, 3250, 1635, 1605, 1485, 1460, 1325, 1210, 1150

(2) 3-Formyl-7-methylsulfonylamino-6-phenoxy-4H-1-benzopyran-4-one was reacted with sodium hypochlorite to obtain 3-chloro-7-methylsulfonylamino-6-phenoxy-4H-1-benzopyran-4-one.

The properties (melting point and IR) of this compound agreed with those of the compound obtained in Example 4.

(3) 3-Formyl-7-methylsulfonylamino-6-phenoxy-4H-1-benzopyran-4-one was reacted with benzyltriphenylphosphonium bromide in the presence of potassium tertbutoxide to obtain 3-(2-phenylvinyl)-7-methylsulfonylamino-6-phenoxy-4H-1-benzopyran-4-one.

Melting point: 174°-175° C. (recrystallized from ethanol)

IR (KBr) cm$^{-1}$: 3400, 1630, 1620, 1480, 1450, 1330, 1200, 1155

(4) 3-Formyl-7-methylsulfonylamino-6-phenoxy-4H-1-benzopyran-4-one was reacted with methylmagnesium iodide to obtain 3-(1-hydroxyethyl)-7-methylsulfonylamino-6-phenoxy-4H-1-benzopyran-4-one.

Melting point: 136°-138° C. (recrystallized from ethyl acetate)

IR (KBr) cm$^{-1}$: 3325, 3225, 1615, 1590, 1480, 1445, 1325, 1205, 1145

(5) 3-Formyl-7-methylsulfonylamino-6-phenoxy-4H-1-benzopyran-4-one was reacted with 2,4-dimethoxybenzylamine. The reaction product was reduced by sodium boron hydride to obtain 3-(2,4-dimethoxybenzylamino)-methyl-7-methylsulfonylamino-6-phenoxy-4H-1-benzopyran-4-one.

This compound was then reacted with acetic anhydride in methanol. The reaction product was treated with trifluoroacetic acid to obtain 3-acetylaminomethyl-7-methylsulfonylamino-6-phenoxy-4H-1-benzopyran-4-one.

Melting point: 240°-242° C. (recrystallized from isopropyl alcohol)

IR (KBr) cm⁻¹: 3350, 3250, 1680, 1640, 1600, 1460, 1340, 1215, 1150

(6) 3-Acetylaminomethyl-7-methylsulfonylamino-6-phenoxy-4H-1-benzopyran-4-one was treated with 6N hydrochloric acid to obtain 3-aminomethyl-7-methylsulfonylamino- 6-phenoxy-4H-1-benzopyran-4-one.

Melting point: 190°-195° C. (decomposed) (recrystallized from ethyl acetate)

IR (KBr) cm⁻¹: 3450, 3070, 1635, 1580, 1480, 1455, 1385, 1320, 1275

EXAMPLE 52

3-Acetyl-7-methylsulfonylamino-6-phenoxy-4H-1-benzopyran-4-one was reacted with bromine to obtain 3-(2-bromoacetyl)-7-methylsulfonylamino-6-phenoxy-4H-1-benzopyran-4-one. It was reacted with thioformamide to obtain 7-methylsulfonylamino-6-phenoxy-3-(thiazol-4-yl)-4H-1-benzopyran-4-one.

Melting point: >250° C. (recrystallized from acetonitrile)

IR (KBr) cm⁻¹: 3260, 1635, 1620, 1480, 1450, 1315, 1200, 1150

EXAMPLE 53

(1) 6-(2-Methoxycarbonylphenoxy)-7-methylsulfonyl-amino-4H-1-benzopyran-4-one was treated in the same manner as in Example 5 (2) to obtain 6-(2-carboxyphenoxy)-7-methylsulfonylamino-4H-1-benzopyran-4-one.

Melting point: 243°-246° C. (recrystallized from acetonitrile)

IR (KBr) cm⁻¹: 3150, 1720, 1670, 1640, 1605, 1480, 1360, 1330, 1260, 1220, 1160

(2) 6-(2-Carboxyphenoxy)-7-methylsulfonylamino-4H-1-benzopyran-4-one was treated in the same manner as in Example 50 (2), Example 50 (5), Example 50 (7) and Example 50 (10) to obtain 6-(2-aminophenoxy)-7-methylsulfonylamino-4H-1-benzopyran-4-one.

Melting point: 238°-240° C. (recrystallized from acetonitrile)

IR (KBr) cm¹: 3415, 3300, 3200, 1635, 1620, 1455, 1330, 1290, 1155

(3) 6-(2-Aminophenoxy)-7-methylsulfonylamino-4H-1-benzopyran-4-one was treated in the same manner as in Reference Example 2 to obtain 6-(2-acetylaminophenoxy)-7-methylsulfonylamino-4H-1-benzopyran-4-one.

Melting point: 130°-132° C. (recrystallized for ethanol)

IR (KBr) cm⁻¹: 3250, 1620, 1480, 1450, 1325, 1290, 1150

(4) 6-(2-Aminophenoxy)-7-methylsulfonylamino-4H-1-benzopyran-4-one was treated in the same manner as in Example 26 (1) to obtain 6-(2-formylaminophenoxy)-7-methylsulfonylamino-4H-1-benzopyran-4-one.

Melting point: 203°-204° C. (recrystallized from acetonitrile)

IR (KBr) cm⁻¹: 3220, 1665, 1620, 1490, 1450, 1320, 1295, 1150

EXAMPLE 54

6-(2-Methoxyphenoxy)-7-methylsulfonylamino-4H-1-benzopyran-4-one was treated in the same manner as in Reference Example 8 (2) to obtain 6-(2-hydroxyphenoxy)-7-methylsulfonylamino-4H-1-benzopyran-4-one.

Melting point: 186.5°-187° C. (recrystallized from isopropyl alcohol)

IR (KBr) cm⁻¹: 3250, 1620, 1585, 1480, 1450, 1320, 1290, 1160, 1140

EXAMPLE 55

(1) 4 g of 3-formyl-7-methylsulfonylamino-6-phenoxy-4H-1-benzopyran-4-one was dissolved in 20 ml of N,N-dimethylformamide. Thereto was added 850 mg of hydroxylamine hydrochloride. The mixture was stirred for 1 hour at 20°-25° C. The reaction mixture was mixed with 50 ml of ethyl acetate and 100 ml of water. The organic layer was separated, washed with water and a saturated aqueous sodium chloride solution in this order, and dried with anhydrous magnesium sulfate. The solvent was removed by distillation under reduced pressure. The resulting crystal was recrystallized from ethanol to obtain 3.0 g (yield: 72.3%) of 3-hydroxyiminomethyl-7-methylsulfonylamino-6-phenoxy-4H-1-benzopyran-4-one having a melting point of 199°-200° C.

IR (KBr) cm⁻¹: 3250, 1620, 1495, 1330, 1210, 1160

The compounds shown in Table 36 were obtained in the same manner.

TABLE 36

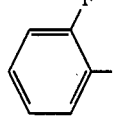

| R⁵ | Melting point (°C.) | IR (KBr) cm⁻¹: |
|---|---|---|
| 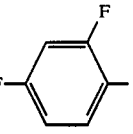 (2-F-phenyl) | 206-207 [Acetonitrile] | 3240, 1620, 1490, 1455, 1335, 1260, 1160 |
| (2,4-diF-phenyl) | 226-227 [Acetonitrile] | 3260, 3220, 1620, 1615, 1490, 1460, 1340, 1160 |

(2) 3.0 g of 3-hydroxyiminomethyl-7-methylsulfonylamino-6-phenoxy-4H-1-benzopyran-4-one was suspended in 30 ml of acetic acid. Thereto was added 900 mg of sodium acetate. The mixture was refluxed for 3 hours. After the completion of the reaction, the solvent was removed by distillation under reduced pressure. The residue was mixed with 50 ml of ethyl acetate and 50 ml of water. The organic layer was separated, washed with water and a saturated aqueous sodium chloride solution in this order, and dried with anhydrous magnesium sulfate. The solvent was removed by distillation under reduced pressure. The resulting crystal was recrystallized from a mixed solvent of ethyl acetate and ethanol to obtain 2.4 g (yield: 83.9%) of 3-cyano-7-methylsulfonylamino-6-phenoxy-4H-1-benzopyran-4-one having a melting point of 219.5°-220.5° C.

IR (KBr) cm$^{-1}$: 3140, 2240, 1650, 1620, 1485, 1445, 1330, 1155

The compounds shown in Table 37 were obtained in the same manner.

TABLE 37

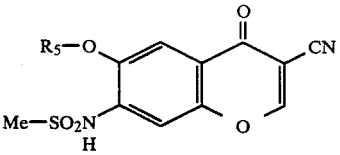

| $R^5$ | Melting point (°C.) | IR (KBr) cm$^{-1}$: |
|---|---|---|
| 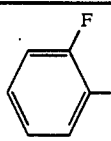 | 244–246 [Acetonitrile] | 3140, 3070, 2240, 1655, 1620, 1490, 1460, 1330, 1320, 1270, 1150 |
| 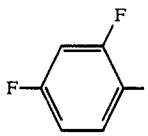 | 247–279 [Acetonitrile] | 3120, 3070, 1645, 1620, 1480, 1450, 1330, 1150 |

EXAMPLE 56

3-Carbamoyl-7-methylsulfonylamino-6-phenoxy-4H-1-benzopyran-4-one was reacted with thionyl chloride in N,N-dimethylformamide to obtain 3-cyano-7-methylsulfonylamino-6-phenoxy-4H-1-benzopyran-4-one. The properties (melting point and IR) of this compound were identical with those of the compound obtained in Example 4.

EXAMPLE 57

(1) 6-(2,4-Difluorophenoxy)-7-methylsulfonylamino-4H-1-benzopyran-4-one was treated in the same manner as in Reference Example 2 to obtain 6-(2,4-difluorophenoxy)-7-(N-acetyl-N-methylsulfonylamino)-4H-1-benzopyran-4-one.

Melting point: 176°-178° C. (recrystallized from isopropyl alcohol)

IR (KBr) cm$^{-1}$: 1705, 1640, 1620, 1440, 1335, 1295, 1245, 1165

The following compound was obtained in the same manner:

6-(2,4-Difluorophenoxy)-3-formylamino-7-(N-acetyl-N-methylsulfonylamino)-4H-1-benzopyran-4-one Melting point: 237°-239° C. (recrystallized from acetonitrile)

IR (KBr) cm$^{-1}$: 3320, 1705, 1685, 1610, 1520, 1485, 1440, 1345, 1240, 1215, 1190, 1160

(2) 7-Methylsulfonylamino-6-phenoxy-4H-1-benzopyran-4-one was reacted with benzoyl chloride in the presence of aluminum chloride to obtain 7-(N-benzoyl-N-methylsulfonylamino)-6-phenoxy-4H-1-benzopyran-4-one.

Melting point: 164°-165.5° C. (recrystallized from ethyl acetate)

IR (KBr) cm$^{-1}$: 1685, 1650, 1610, 1475, 1435, 1360, 1285, 1260, 1200, 1160

(3) 7-Methylsulfonylamino-6-phenoxy-4H-1-benzopyran-4-one was reacted with methyl iodide in the presence of sodium hydride to obtain 7-(N-methyl-N-methylsulfonylamino)-6-phenoxy-4H-1-benzopyran-4-one.

Melting point: 187°-189° C. (recrystallized from ethanol)

IR (KBr) cm$^{-1}$: 1630, 1610, 1480, 1440, 1340, 1150

EXAMPLE 58

3-(4-Chlorobutyrylamino)-7-methylsulfonylamino-6-phenoxy-4H-1-benzopyran-4-one was reacted with sodium hydride in N,N-dimethylformamide to obtain 7-methylsulfonylamino-3-(2-oxopyrrolidin-1-yl)-6-phenoxy-4H-1-benzopyran-4-one.

Melting point: 192°-193° C. (recrystallized from ethanol)

IR (KBr) cm$^{-1}$: 1680, 1635, 1610, 1485, 1335, 1280, 1160

EXAMPLE 59

2-Carboxy-7-methylsulfonylamino-6-phenoxy-4H-1-benzopyran-4-one was reacted with 5-aminotetrazole in the presence of dicyclohexylcarbodiimide to obtain-7-methylsulfonyl-6-phenoxy-2-[(1,2,3,4-tetrazol-5-yl)-aminocarbonyl]-4H-1-benzopyran-4-one.

Melting point: >250° C. (recrystallized from ethylene glycol monomethyl ether)

IR (KBr) cm$^{-1}$: 3120, 1690, 1630, 1590, 1570, 1450, 1370, 1325, 1200, 1140

EXAMPLE 60

3-Cyano-7-methylsulfonylamino-6-phenoxy-4H-1-benzopyran-4-one was reacted with sodium azide in the presence of aluminum chloride to obtain 7-methylsulfonyl-amino-6-phenoxy-3-(1,2,3,4-tetrazol-5-yl)-4H-1-benzopyran-4-one.

Melting point: >250° C. (recrystallized from dioxane-diisopropyl ether)

IR (KBr) cm$^{-1}$: 3370, 3170, 1630, 1480, 1460, 1340, 1295, 1160

EXAMPLE 61

3.56 g of 3-cyano-7-methylsulfonylamino-6-phenoxy-4H-1-benzopyran-4-one, 970 mg of hydroxylamine hydrochloride, 1.5 ml of water, 7 ml of N,N-dimethylformamide and 150 ml of ethanol were mixed, and subjected to refluxing for 3 hours. The reaction mixture was cooled, and thereafter, the precipitated crystals were collected by filtration and then recrystallized from acetonitrile to obtain 2.8 g (yield: 72%) of 2-amino-3-carbamoyl-7-methylsulfonylamino-6-phenoxy-4H-1-benzopyran-4-one having a melting point of >250° C.

IR (KBr) cm$^{-1}$: 3460, 3380, 3125, 1640, 1570, 1545, 1475, 1320, 1220, 1150

EXAMPLE 62

In 10 ml of a mixture of anhydrous tetrahydrofuran-hexamethylphosphoric acid triamide (7:3) was dissolved 1.00 g of 2,3-dihydro-7-methylsulfonylamino-6-phenoxy-4H-1-benzopyran-4-one. To the resulting solution was added 10 ml of a tetrahydrofuran solution of 1,1,1,3,3,3-hexamethylsilazane lithium salt consisting of 1.17 g of 1,1,1,3,3,3-hexamethylsilazane and 6.6 millimoles of n-butyllithium at −78° C., and the resulting mixture was stirred for 40 minutes, after which 500 mg of methyl methanethiolsulfate was added at the same temperature and the mixture was stirred for 15 minutes. Subsequently, the temperature of the reaction mixture was elevated to room temperature. The reaction mixture was introduced into 80 ml of 2N hydrochloric acid with ice-cooling and the resulting mixture was extracted with two 40-ml portions of ethyl acetate. The extracts were combined and washed with water and saturated aqueous sodium chloride solution in this order and then dried over anhydrous magnesium sulfate. The solvent was removed by distillation under reduced pressure and the oily product obtained was purified by a column chromatography (eluant: toluene:ethyl acetate=50:1) to obtain 480 mg (yield: 39.6%) of 2,3-dihydro-7-methylsulfonylamino-3-methylthio-6-phenoxy-4H-1-benzopyran-4-one.

The physical properties (IR and melting point) of this product were identical with those of the compound obtained in Example 22 (2).

PREPARATION EXAMPLE 1

Hard gelatin capsules were prepared using the following components:

| | |
|---|---|
| 6-(2-Fluorophenoxy)-3-formylamino-7-methylsulfonylamino-4H-1-benzopyran-4-one | 50 mg |
| Lactose | 114.5 mg |
| Corn starch | 20 mg |
| Hydroxypropyl cellulose | 2 mg |
| Light silicic acid anhydride | 1.5 mg |
| Carboxymethyl cellulose calcium (ECG 505) | 10 mg |
| Magnesium stearate | 2 mg |
| Total | 200 mg |

The above components of the above amounts were filled in one hard capsule according to an ordinary method.

PREPARATION EXAMPLE 2

Tablets were prepared using the following components:

| | |
|---|---|
| 3-Formylamino-7-methylsulfonylamino-6-phenoxy-4H-1-benzopyran-4-one | 25 mg |
| Lactose | 49 mg |
| Microcrystalline cellulose | 36 mg |
| Hydroxypropyl cellulose | 1 mg |
| Carboxymethyl cellulose calcium (ECG 505) | 6.6 mg |
| Magnesium stearate | 1.2 mg |
| Talc | 1.2 mg |
| Total | 100 mg |

The above components of the above amounts were made into one tablet according to an ordinary method.

PREPARATION EXAMPLE 3

Tablets were prepared using the following components:

| | |
|---|---|
| 3-Formylamino-7-methylsulfonylamino-6-phenoxy-4H-1-benzopyran-4-one | 50 mg |
| Lactose | 74 mg |
| Microcrystalline cellulose | 55 mg |
| Hydroxypropyl cellulose | 2 mg |
| Carboxymethyl cellulose calcium (ECG 505) | 15 mg |
| Magnesium stearate | 2 mg |
| Talc | 2 mg |
| Total | 200 mg |

The above components of the above amounts were made into one tablet according to an ordinary method.

PREPARATION EXAMPLE 4

Tablets were prepared using the following components:

| | |
|---|---|
| 3-Formylamino-7-methylsulfonylamino-6-phenoxy-4H-1-benzopyran-4-one | 100 mg |
| Lactose | 49 mg |
| Microcrystalline cellulose | 55 mg |
| Hydroxypropyl cellulose | 2 mg |
| Carboxymethyl cellulose calium (ECG 505) | 15 mg |
| Magnesium stearate | 2 mg |
| Talc | 2 mg |
| Total | 225 mg |

The above components of the above amounts were made into one tablet according to an ordinary method.

PREPARATION EXAMPLE 5

Tablets were prepared using the following components:

| | |
|---|---|
| 3-Carbamoyl-6-phenoxy-7-methylsulfonylamino-4H-1-benzopyran-4-one | 200 mg |
| Microcrystalline cellulose | 100 mg |
| Sodium starch glycolate (NF) | 30 mg |
| Magnesium stearate | 3 mg |
| Total | 333 mg |

The above components of the above amounts were made into one tablet according to an ordinary method.

What is claimed is:

1. A 4H-1-benzopyran-4-one derivative represented by the following formula or a pharmaceutically acceptable salt thereof:

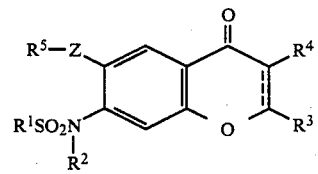

wherein $R^1$ represents an unsubstituted or halogen-substituted lower alkyl, lower alkenyl or aryl group; $R^2$ represents a hydrogen atom or an alkyl or alkanoyl group; $R^3$ represents a hydrogen or halogen atom, a cyano, azido, carboxyl, hydroxyl, formyl or alkoxycarbonyl group or a substituted or unsubstituted alkyl, alkoxy, phenoxy, cycloalkyl, carbamoyl, amino or phenyl group; $R^4$ represents a hydrogen or halogen atom, a nitro, cyano, carboxyl, alkanoyl, hydroxyl or alkoxycarbonyl group, a substituted or unsubstituted alkyl, alkoxy, alkylthio, phenylthio, lower alkynyl, lower alkenyl, sulfamoyl, alkylsulfinyl, alkylsulfonyl, amidino, phenyl or heterocyclic group or a group of the formula

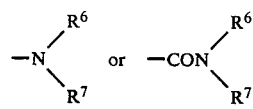

($R^6$ is a hydrogen atom, a hydroxyl, cyano or alkoxycarbonyl group or a substituted or unsubstituted alkyl, cycloalkyl, phenyl, amino, alkanoyl, benzoyl, carbamoyl, alkylsulfonyl, imino-methyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a substituted or unsubstituted azetidin-1-yl, pyrrolidin-1-yl, piperidin-1-yl or pyrrol-1-yl group); $R^5$ represents a substituted or unsubstituted phenyl, thienyl, furyl or pyridyl group; Z represents an oxygen or sulfur atom or an imino group and the broken line means a single or double bond;

the alkyl, alkoxy, cycloalkyl, phenoxy, amino, carbamoyl and phenyl groups for $R^3$, the alkyl, alkoxy, alkylthio, phenylthio, amidino, lower alkenyl, lower alkynyl, sulfamoyl, alkylsulfinyl, alkylsulfonyl, phenyl and heterocyclic groups for $R^4$, the alkyl, cycloalkyl, phenyl, amino, alkanoyl, benzoyl, carbamoyl, alkylsulfonyl, iminomethyl and amidino groups for $R^6$, the alkyl, alkoxy, cycloalkyl, phenyl and heterocyclic groups for $R^7$, the azetidin-1-yl, pyrrolidin-1-yl, piperidin-1-yl or pyrrol-1-yl group which $R^6$ and $R^7$ form with the nitrogen atom to which the two are bonded and the phenyl, thienyl, furyl and pyridyl groups for $R^5$ may each be substituted by at least one substituent selected from the group consisting of halogen atoms and alkoxy, alkylthio, phenoxy, carboxyl, alkanoyl, alkoxycarbonyl, carbamoyl, sulfamoyl, cyano, alkylsulfonyl, hydroxyl, mercapto, alkanoylamino, alkylamino, dialkylamino, alkyl, cycloalkyl, oxo, nitro, haloalkyl, amino, phenyl, alkoxy-carbonylamino, hydroxyimino and heterocyclic groups; and the term "heterocyclic group" mentioned for $R^4$, $R^7$ and above substituent represents thienyl, furyl, pyrrolyl, oxazolyl, isoxazolyl, thiazolyl, isothiazolyl, imidazolyl, benzimidazolyl, benzthiazolyl, 1,2,3-thiadiazolyl, 1,2,4-thiadiazolyl, 1,3,4-thiadiazolyl, 1,3,4-oxadiazolyl, 1,2,3-triazolyl, 1,2,4-triazolyl, tetrazolyl, pyridyl, quinolyl, isoquinolyl, pyrimidinyl, piperazinyl, pyrazinyl, pyridazinyl, 1,2,3,4-tetrahydroquinoyl, 1,2,4-triazinyl, imidazo[1,2-b][1,2,4]triazinyl, pyrrolidinyl, morpholinyl or quinuclidinyl group.

2. A 4H-1-benzopyran-4-one derivative or a pharmaceutically acceptable salt thereof according to claim 1, wherein Z represents an oxygen or sulfur atom; $R^5$ represents a substituted or unsubstituted phenyl or pyridyl group; $R^1$ represents an unsubstituted or halogen-substituted lower alkyl or lower alkenyl group; $R^2$ represents a hydrogen atom or an alkanoyl group; $R^3$ and $R^4$, which may be the same or different, represent hydrogen atoms, carbamoyl, carboxyl, formyl, hydroxyl or alkoxycarbonyl groups or substituted or unsubstituted alkyl, alkoxy or phenyl groups and the broken line means a double bond.

3. A 4H-1-benzopyran-4-one derivative or a pharmaceutically acceptable salt thereof according to claim 1, wherein $R^5$ represents a substituted or unsubstituted phenyl or pyridyl group; Z represents an oxygen or sulfur atom; $R^1$ represents an unsubstituted or halogen-substituted lower alkyl or lower alkenyl group; $R^2$ represents a hydrogen atom or an alkanoyl group; $R^4$ represents a group of the formula

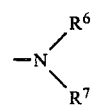

($R^6$ is a hydrogen atom; a hydroxyl, cyano or alkoxycarbonyl group or a substituted or unsubstituted alkyl, cycloalkyl, phenyl, amino, alkanoyl, benzoyl, carbamoyl, iminomethyl or amidino group and $R^7$ is a hydrogen atom or a substituted or unsubstituted alkyl or cycloalkyl group, or $R^6$ and $R^7$, when taken together with the nitrogen atom to which the two are bonded, form a azetidin-1-yl, pyrrolidin-1-yl, piperidin-1-yl or pyrrol-1-yl group); $R^3$ represents a hydrogen or halogen atom, a cyano, azido, carbamoyl, carboxyl, hydroxyl or alkoxycarbonyl group or a substituted or unsubstituted alkyl, alkoxy, amino or phenyl group and the broken line means a double bond.

4. A 4H-1-benzopyran-4-one derivative or a pharmaceutically acceptable salt thereof according to claim 1, wherein Z represents an oxygen atom.

5. A 4H-benzopyran-4-one derivative or a pharmaceutically acceptable salt thereof according to claim 1, wherein $R^1$ represents a lower alkyl group.

6. A 4H-1-benzopyran-4-one derivative or a pharmaceutically acceptable salt thereof according to claim 1, wherein $R^2$ represents a hydrogen atom.

7. A 4H-1-benzopyran-4-one derivative or a pharmaceutically acceptable salt thereof according to claim 1, wherein $R^3$ represents a hydrogen atom or an alkyl group.

8. A 4H-1-benzopyran-4-one derivative or a pharmaceutically acceptable salt thereof according to claim 1, wherein $R^4$ represents a substituted or unsubstituted alkylthio, phenylthio, alkylsulfinyl or alkylsulfonyl group or a group of the formula

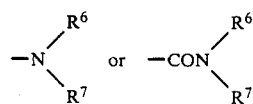

($R^6$ and $R^7$ have the same meanings as defined above).

9. A 4H-1-benzopyran-4-one derivative or a pharmaceutically acceptable salt thereof according to claim 1, wherein $R^4$ represents an alkylthio, formylamino or carbamoyl group.

10. A 4H-1-benzopyran-4-one derivative or a pharmaceutically acceptable salt thereof according to claim 9, wherein $R^5$ represents a substituted or unsubstituted phenyl group.

11. A 4H-1-benzopyran-4-one derivative or a pharmaceutically acceptable salt thereof according to claim 10, wherein $R^5$ represents a phenyl group which may be substituted by at least one substituent selected from the group consisting of halogen atoms, hydroxyl group, amino group, carboxyl group, haloalkyl groups, alkyl groups, alkoxy groups, alkoxycarbonyl groups, alkanoylamino groups and carbamoyl group.

12. A pharmaceutical composition comprising an effective amount of a 4H-1-benzopyran-4-one derivative represented by the following formula or a pharmaceutically acceptable salt thereof:

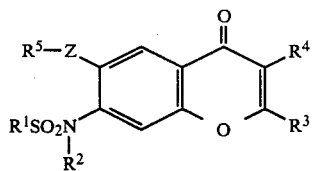

wherein $R^1$ represents an unsubstituted or halogen-substituted lower alkyl, lower alkenyl or aryl group; $R^2$ represents a hydrogen atom or an alkyl or alkanoyl group; $R^3$ represents a hydrogen or halogen atom, a cyano, azido, carboxyl, hydroxyl, formyl or alkoxycarbonyl group or a substituted or unsubstituted alkyo, alkoxy, phenoxy, cycloalkyl, carbamoyl, amino or phenyl group; $R^4$ represents a hydrogen or halogen atom, a nitro, cyano, carboxyl, alkanoyl, hydroxyl or alkoxycarbonyl group, a substituted or unsubstituted alkyl, alkoxy alkylthio, phenylthio, lower alkynyl, lower alkenyl, sulfamoyl, alkylsulfinyl, alkylsulfonyl, amidino, phenyl or heterocyclic group or a group of the formula

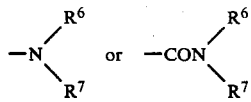

($R^6$ is a hydrogen atom, a hydroxyl, cyano or alkoxycarbonyl group or a substituted or unsubstituted alkyl, cycloalkyl, phenyl, amino, alkanoyl, benzoyl, carbamoyl, alkylsulfonyl, iminomethyl or amidino group and $R^7$ is a hydrogen atom or a substituted or unsubstituted alkyl, alkoxy, phenyl, cycloalkyl or heterocyclic group, or $R^6$ and $R^7$, when taken together with the nitrogen atom to which the two are bonded, form a substituted or unsubstituted azetidin-1-yl, pyrrolidin-1-yl, piperidine-1-yl or pyrrol-1-yl group); $R^5$ represents a substituted or unsubstituted phenyl, thienyl, furyl or pyridyl group; and Z represents an oxygen or sulfur atom or an imino group;

the alkyl, alkoxy, cycloalkyl, phenoxy, amino, carbamoyl and phenyl groups for $R^3$, the alkyl, alkoxy, alkylthio, phenylthio, amidino, lower alkenyl, lower alkynyl, sulfamoyl, alkylsulfinyl, alkylsulfonyl, phenyl and heterocyclic groups for $R^4$, the alkyl, cycloalkyl, phenyl, amino, alkanoyl, benzoyl, carbamoyl, alkylsulfonyl, iminomethyl and amidino groups for $R^6$, the alkyl, alkoxy, cycloalkyl, phenyl and heterocyclic groups for $R^7$, the 4- to 6-membered heterocyclic groups which $R^6$ and $R^7$ form with the nitrogen atom to which the two are bonded and the phenyl, thienyl, furyl and pyridyl groups for $R^5$ may each be substituted by at least one substituent selected from the group consisting of halogen atoms and alkoxy, alkylthio, phenoxy, carboxyl, alkanoyl, alkoxycarbonyl, carbamoyl, sulfamoyl, cyano, alkylsulfonyl, hydroxyl, mercapto, alkanoylamino, alkylamino, dialkylamino, alkyl, cycloalkyl, oxo, nitro, haloalkyl, amino, phenyl, alkoxy-carbonylamino, hydroxyimino and heterocyclic groups; and the term "heterocyclic group" mentioned for $R^4$, $R^7$ and above substituent represents thienyl, furyl, pyrrolyl, oxazolyl, isoxazolyl, thiazolyl, isothiazolyl, imidazolyl, benzimidazolyl, benzthiazolyl, 1,2,3-thiadiazolyl, 1,2,4-thiadiazolyl, 1,3,4-thiadiazolyl, 1,3,4-oxadiazolyl, 1,2,3-triazolyl, 1,2,4-triazolyl, tetrazolyl, pyridyl, quinolyl, isoquinolyl, pyrimidinyl, piperazinyl, pyrazinyl, pyridazinyl, 1,2,3,4-tetrahydroquinoyl, 1,2,4-triazinyl, imidazo [1,2-b] [1,2,4] triazinyl, pyrrolidinyl, morpholinyl or quinuclidinyl group.

13. A pharmaceutical composition according to claim 12, wherein Z represents an oxygen or sulfur atom; $R^5$ represents a substituted or unsubstituted phenyl or pyridyl group; $R^1$ represents an unsubstituted or halogen substituted lower alkyl or lower alkenyl group; $R^2$ represents a hydrogen atom or an alkanoyl group and $R^3$ and $R^4$, which may be the same or different, represent hydrogen atoms, carbamoyl, carboxyl, formyl, hydroxyl or alkoxycarbonyl groups or substituted or unsubstituted alkyl, alkoxy or phenyl groups.

14. A pharmaceutical composition according to claim 12, wherein $R^5$ represents a substituted or unsubstituted phenyl or pyridyl group; Z represents an oxygen or sulfur atom; $R^1$ represents an unsubstituted or halogen-substituted lower alkyl or lower alkenyl group; $R^2$ represents a hydrogen atom or an alkanoyl group; $R^4$ represents a group of the formula

($R^6$ is a hydrogen atom, a hydroxyl, cyano or alkoxycarbonyl group or a substituted or unsubstituted alkyl, cycloalkyl, phenyl, amino, alkanoyl, benzoyl, carbamoyl, iminomethyl or amidino group and $R^7$ is a hydrogen atom or a substituted or unsubstituted alkyl or cycloalkyl group, or $R^6$ and $R^7$, when taken together with the nitrogen atom to which the two are bonded, from azetidin-1-yl, pyrrolidin-1-yl, piperidin-1-yl or pyrrol-1-yl group); and $R^3$ represents a hydrogen or halogen atom, a cyano, azido, carbamoyl, carboxyl, hydroxyl or alkoxycarbonyl group or a substituted or unsubstituted alkyl, alkoxy, amino or phenyl group.

15. A pharmaceutical composition according to claim 12, wherein Z represents an oxygen atom.

16. A pharmaceutical composition according to claim 12, wherein $R^1$ represents a lower alkyl group.

17. A pharmaceutical composition according to claim 12, wherein $R^2$ represents a hydrogen atom.

18. A pharmaceutical composition according to claim 12, wherein $R^3$ represents a hydrogen atom or an alkyl group.

19. A pharmaceutical composition according to claim 12, wherein $R^4$ represents a substituted or unsubstituted alkylthio, alkylsulfinyl or alkylsulfonyl group or a group of the formula

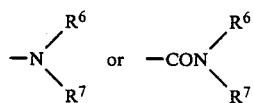

$R^6$ and $R^7$ have the same meanings as defined above).

20. A pharmaceutical composition according to claim 19, wherein $R^4$ represents an alkylthio, formylamino or carbamoyl group.

21. A pharmaceutical composition according to claim 20, wherein $R^5$ represents a substituted or unsubstituted phenyl group.

22. A pharmaceutical composition according to claim 21, wherein $R^5$ represents a phenyl group which may be substituted by at least one substituent selected from the group consisting of halogen atoms, hydroxyl group, amino group, carboxyl group, haloalkyl groups, alkyl groups, alkoxy groups, alkoxycarbonyl groups, alkanoylamino groups and carbamoyl group.

23. A method for treating inflammatory, pyretic, analgesic or rheumatic diseases in a host mammal which comprises an effective amount of the compound in claim 1, in combination with a pharmaceutically acceptable inert excipient, diluent or carrier.

24. The 4H-1-benzopyran-4-one derivative of claim 1, which is 6-(2-fluorophenoxy)-3-formylamino-7-methylsulfonylamino-4H-1-benzopyran-4-one or a pharmaceutically acceptable salt thereof.

25. The 4H-1-benzopyran-4-one derivative of claim 1, which is 3-carbamoyl-2-methyl-7-methylsulfonylamino-6-phenoxy-4H-1-benzopyran-4-one or a pharmaceutically acceptable salt thereof.

26. The 4H-1-benzopyran-4-one derivative of claim 1, which is 3-formylamino-7-methylsulfonylamino-6-phenoxy-4H-1-benzopyran-4-one or a pharmaceutically acceptable salt thereof.

27. The 4H-1-benzopyran-4-one derivative of claim 1, which is 3-carbamoyl-7-methylsulfonylamino-6-phenoxy-4H-1-benzopyran-4-one or a pharmaceutically acceptable salt thereof.

* * * * *